US009844593B2

(12) United States Patent
Andre et al.

(10) Patent No.: US 9,844,593 B2
(45) Date of Patent: Dec. 19, 2017

(54) METHODS FOR TREATMENT OF RECURRENT HEMATOLOGICAL MALIGNANCIES

(75) Inventors: Pascale Andre, Marseilles (FR); Renaud Buffet, Vanves (FR); Marcel Rozencweig, Marseilles (FR); Jerome Tiollier, Marseilles (FR)

(73) Assignee: INNATE PHARMA SA, Marseille (FR)

( * ) Notice: Subject to any disclaimer, the term of this patent is extended or adjusted under 35 U.S.C. 154(b) by 0 days.

(21) Appl. No.: 13/988,954

(22) PCT Filed: Nov. 22, 2011

(86) PCT No.: PCT/US2011/061840
§ 371 (c)(1),
(2), (4) Date: May 22, 2013

(87) PCT Pub. No.: WO2012/071411
PCT Pub. Date: May 31, 2012

(65) Prior Publication Data
US 2013/0251711 A1    Sep. 26, 2013

Related U.S. Application Data

(60) Provisional application No. 61/415,973, filed on Nov. 22, 2010.

(51) Int. Cl.
*A61K 39/395*    (2006.01)
*C07K 16/28*    (2006.01)
*A61K 39/00*    (2006.01)

(52) U.S. Cl.
CPC ...... *A61K 39/3955* (2013.01); *C07K 16/2803* (2013.01); *A61K 2039/505* (2013.01)

(58) Field of Classification Search
None
See application file for complete search history.

(56) References Cited

U.S. PATENT DOCUMENTS

| 8,119,775 B2 * | 2/2012 | Moretta ............. C07K 16/2803 530/388.15 |
| 2006/0194952 A1 | 8/2006 | Gillies et al. |
| 2008/0317708 A1 | 12/2008 | Zeldis |
| 2009/0075340 A1 | 3/2009 | Padkaer et al. |
| 2009/0196850 A1 | 8/2009 | Romagne et al. |
| 2010/0189723 A1 | 7/2010 | Wagtmann et al. |

FOREIGN PATENT DOCUMENTS

| JP | 2008-526813 | 7/2008 | |
| JP | 2010-013482 | 1/2010 | |
| JP | 2010-515709 | 5/2010 | |
| WO | 2005/003168 | 1/2005 | |
| WO | 2005/003172 | 1/2005 | |
| WO | 2006/003179 | 1/2006 | |
| WO | WO2006/072625 | * 7/2006 | |
| WO | WO2006/072626 | * 7/2006 | ............. C07K 16/28 |
| WO | WO2008/084106 | * 7/2008 | ............. A61K 39/395 |
| WO | WO 2010/045354 | 4/2010 | |

OTHER PUBLICATIONS

Kyle et al., Prognostic factors and predictors of outcome of immunoglobulin M monoclonal gammopathy of undetermined significance. Clyn. Lymphoma, 5, 257-260, 2005.*
Ohno et al., Polyclonal proliferation of plasma cells associated with marked hypergammaglobulinemia in an elderly patient. Int. J. Hematol.81, 62-65, 2005.*
Noel et al., Plasma cell leukemia: an evaluation of response to therapy. Am. J. Medicine 83, 1062-1068, 1987.*
Hussein et al. A phase II clinical study of arsenic trioxide (ATO) in patients (pts) with relapsed or refractory multiple myeloma (MM); a preliminary report. Blood, 98 (11), Part1, pp. 378a, 2001.*
Kyle et al., Clinical course and prognosis of smoldering (asymptomatic) Waldenstrom's macroglobulinemia. Blood, 112 (11), pp. 936-937, 2008.*
Suzuki et al. Clinical characteristics and prognostic implications of NPM1 mutations in acute myeloid leukemia, Blood, 106, 2854-2861, 2005.*
Berger et al. Loss of the NPM1 gene in myeloid disorders with chromosome 5 rearrangements, Leukemia, 20, 319-321, 2006.*
Weiss, et al., "A monoclonal gammopathy precedes multiple myeloma in most patients," Blood. May 28, 2009;113(22):5418-22.
Döhner H, et al. "Diagnosis and management of acute myeloid leukemia in adults: recommendations from an international expert panel, on behalf of the European LeukemiaNet." Blood. Jan. 21, 2010;115(3):453-74.
The Journal of Therapy, 2005, vol. 87, No. 4, pp. 1537-1542.
The Journal of the Japanese Society of Internal Medicine, 2006, vol. 95, No. 3, pp. 122-125.
Farag, et al. "An Open-label, Dose-escalation Safety and Tolerability Trial Assessing Anti-KIR (1-7F9) in Subjects With Multiple Myeloma," In: ClinicalTrials.gov A service of the U.S. National Institutes of Health, First received: May 21, 2007. ClinicalTrials.gov Identifier: NCT00552396. Available from: https://clinicaltrials.gov/ct2/show/NCT00552396?term=1-7F9&rank=2.
Attal, et al. "Evaluation of Activity, Safety and Pharmacology of IPH2101 a Human Monoclonal Antibody in Patients With Multiple Myeloma (REMYKIR)" In: ClinicalTrials.gov A service of the U.S. National Institutes of Health, First received: Oct. 21, 2009. ClinicalTrials.gov Identifier: NCT00999830. Available from: https://clinicaltrials.gov/ct2/show/NCT00999830?term=1-7F9&rank=3.
Mrozek, et al. "Clinical relevance of mutations and gene-expression changes in adult acute myeloid leukemia with normal cytogenetics: are we ready for a prognostically prioritized molecular classification?" Blood. Jan. 15, 2007;109 (2):431-48.
"(2) Acute Lymphocytic Leukemia," The Journal of Therapy, 2005, vol. 87, No. 4, pp. 1537-1542. Translation and original attached.

(Continued)

*Primary Examiner* — Elly-Gerald Stoica
(74) *Attorney, Agent, or Firm* — Robin L. Teskin; LeClairRyan, A Professional Corporation

(57) ABSTRACT

Compositions comprising compounds that neutralize NK cell inhibitory receptors and methods of using such compositions in the treatment of hematological malignancies are provided.

10 Claims, 6 Drawing Sheets

(56) References Cited

OTHER PUBLICATIONS

"1. Acute Leukemia," The Journal of the Japanese Society of Internal Medicine, 2006, vol. 95, No. 3, pp. 122-125. Translation and original attached.
Vey N, et al. "A phase 1 trial of the anti-inhibitory KIR mAb IPH2101 for AML in complete remission," Blood. Nov. 22, 2012;120(22):4317-23.
Unknown, The journal of therapy, Oct. 2010, vol. 92, No. 10, pp. 2373-2379 [partial translation included].
Unknown, Pathology and clinical medicine, 2001, vol. 19, No. 11, pp. 1172-1177 [partial translation included].
Ma W, et al. "Detection of nucleophosmin gene mutations in plasma from patients with acute myeloid leukemia: clinical significance and implications," Cancer Biomark. 2009;5(1):51-8.
Döhner K, et al. "Mutant nucleophosmin (NPM1) predicts favorable prognosis in younger adults with acute myeloid leukemia and normal cytogenetics: interaction with other gene mutations," Blood. Dec. 1, 2005;106(12):3740-6.

* cited by examiner

A

```
                           1                                                  50
DF-200 LIGHT VARIABLE   (1) M--ESQTLVFISILLWLYGNDGKIVMTQSPKSMSMSVGERVTLTCKASEN
PAN2D-LIGHT-VARIABLE    (1) MDFQVQIPSFLLISASVIMSRGQIVLTQSPASMSAELGERVTMTCTASSS
CONSENSUS               (1)        Q  FI I   L  A GNIVLTQSP SNS SLGERVTLTC AS 51                                                 100
DF-200 LIGHT VARIABLE  (49) VVL-YVSWYQQKPEQSPKLLTYGASNRYLGVPDRPTGSGSATDFTLFISS
PAN2D-LIGHT-VARIABLE   (51) VSSSYLYWYQQKPGSSDKLWTYSTSNLASGVPARPSGSGSSTSYSLFISS
CONSENSUS              (51) V S YL WYDQKP SPKL IY  SK  SGVP RPSGSGSAT FSLFISS 101              131
DF-200 LIGHT VARIABLE  (98) VQAKDLADYKCGQGTSYPYTFGGGTKLEIKR
PAN2D-LIGHT-VARIABLE  (101) XEAEDAATYYCHQYERSPPTFGGGTKLEIKR
CONSENSUS             (101) M AND A YNC Q H  P TFGGGIKLEIKR
```

B

```
DF-200 LIGHT VARIABLE  (44) KASENVVT-YVS    (SEQ ID NO.3)
PAN2D-LIGHT-VARIABLE   (46) TASSSVSSSYLY    (SEQ ID NO.4)
CONSENSUS                   AS   V S YL
```

C

```
DF-200 LIGHT VARIABLE  (70) GASNRYT    (SEQ ID NO.5)
PAN2D-LIGHT-VARIABLE   (73) STSNLAS    (SEQ ID NO.6)
CONSENSUS                      SN  S
```

D

```
DF-200 LIGHT VARIABLE  (109) GQGYSYPYT   (SEQ ID NO.7)
PAN2D-LIGHT-VARIABLE   (112) HQYHRSPPT   (SEQ ID NO.8)
CONSENSUS                     Q H  P T
```

MAVLGLLFCLVTFPSCVLS

QVQLEQSGPGLVQPSQSLSITCTVSGFSFTPYGVHWVRQSPGKGLEWLGVIWSGGNTDY
NAAFISRLSINKDNSKSQVFFKMNSLQVNDTAIYYCARNPRPGNYPYGMDYWGQGTSVT
VSS (SEQ ID NO:9)

B

GFSFTPYGVH (SEQ ID NO:10)

C

VIWSGGNTDYNAAFIS (SEQ ID NO:11)

D

NPRPGNYPYGMDY (SEQ ID NO:12)

FIG. 3

1-7F9 VL AND VH

A

EIVLTQSPVTLSLSPGERATLSCRASQSVSSYLAWYQQKPGQAPRLLIYDASNRATGIPARFSGSGSG
TDFTLTISSLEPEDFAVYYCQQRSNWMYTFGQGTKLEIKRT (SEQ ID NO:15)

B gaaattgtgttgacacagtctccagtcaccctgtctttgtctccaggggaaagagccaccctctcctg
cagggccagtcagagtgttagcagctacttagcctggtaccaacagaaacctggccaggctcccaggc
tcctcatctatgatgcatccaacagggccactggcatcccagccaggttcagtggcagtgggtctggg
acagacttcactctcaccatcagcagcctagagcctgaagattttgcagtttattattgtcagcagcg
tagcaactggatgtacacttttggccaggggaccaagctggagatcaaacgaact (SEQ ID
NO:16)

C

QVQLVQSGAEVKKPGSSVKVSCKASGGTFSFYAISWVRQAPGQGLEWMGGFIPIFGAANYAQKFQGRV
TITADESTSTAYMELSSLRSDDTAVYYCARIPSGSYYYDYDMDVWGQGTTVTVSS (SEQ ID
NO:17)

D caggtccagctggtgcagtctggggctgaggtgaagaagcctgggtcctcggtgaaggtctcctgcaa
ggcttctggaggcaccttcagtttctatgctatcagctgggtgcgacaggcccctggacaagggcttg
agtggatgggagggttcatccctatctttggtgcagcaaactacgcacagaagttccagggcagagtc
acgattaccgcggacgaatccacgagcacagcctacatggaactgagcagcctgagatctgacgacac
ggccgtgtattactgtgcgagaatccctagtgggagctactactacgactacgatatggacgtctggg
gccaagggaccacggtcaccgtctcctca (SEQ ID NO:18)

FIG. 4

```
  1  HEGVHRKPSL LAHPGRLVKS EETVILQCWS DVMFEHPLLH REGMANDTLR
 51  LIGEHHDGVS KANPSISRMT QDLAGTYRCS GSVTHSPYQV SAPSDPLDIV
101  IIGLYEKPSL SAQLGPTVLA GENVTLSCSS RSSYDMYHLS REGEAHERRL
151  PAGPKVNGTF QADFPLGPAT HGGTYRCFGS FHDSPYEWSK SSDPLLVSVT
201  GNPSNSWPSP TEPSSKTGNP RHLH
```

FIG. 6

SEQUENCE LISTING

<160> NUMBER OF SEQ ID NOS: 58

<210> SEQ ID NO 1
<211> LENGTH: 128
<212> TYPE: PRT
<213> ORGANISM: Mus musculus

<400> SEQUENCE: 1

Met Glu Ser Gln Thr Leu Val Phe Ile Ser Ile Leu Leu Trp Leu Tyr
1               5                   10                  15

Gly Ala Asp Gly Asn Ile Val Met Thr Gln Ser Pro Lys Ser Met Ser
            20                  25                  30

Met Ser Val Gly Glu Arg Val Thr Leu Thr Cys Lys Ala Ser Glu Asn
        35                  40                  45

Val Val Thr Tyr Val Ser Trp Tyr Gln Gln Lys Pro Glu Gln Ser Pro
    50                  55                  60

Lys Leu Leu Ile Tyr Gly Ala Ser Asn Arg Tyr Thr Gly Val Pro Asp
65                  70                  75                  80

Arg Phe Thr Gly Ser Gly Ser Ala Thr Asp Phe Thr Leu Thr Ile Ser
                85                  90                  95

Ser Val Gln Ala Glu Asp Leu Ala Asp Tyr His Cys Gly Gln Gly Tyr
            100                 105                 110

Ser Tyr Pro Tyr Thr Phe Gly Gly Gly Thr Lys Leu Glu Ile Lys Arg
        115                 120                 125

<210> SEQ ID NO 2
<211> LENGTH: 131
<212> TYPE: PRT
<213> ORGANISM: Mus musculus

<400> SEQUENCE: 2

Met Asp Phe Gln Val Gln Ile Phe Ser Phe Leu Leu Ile Ser Ala Ser
1               5                   10                  15

Val Ile Met Ser Arg Gly Gln Ile Val Leu Thr Gln Ser Pro Ala Ser
            20                  25                  30

Met Ser Ala Ser Leu Gly Glu Arg Val Thr Met Thr Cys Thr Ala Ser
        35                  40                  45

Ser Ser Val Ser Ser Tyr Leu Tyr Trp Tyr Gln Gln Lys Pro Gly
    50                  55                  60

Ser Ser Pro Lys Leu Trp Ile Tyr Ser Thr Ser Asn Leu Ala Ser Gly
65                  70                  75                  80

Val Pro Ala Arg Phe Ser Gly Ser Gly Ser Gly Thr Ser Tyr Ser Leu
                85                  90                  95

Thr Ile Ser Ser Met Glu Ala Glu Asp Ala Ala Thr Tyr Tyr Cys His
            100                 105                 110

Gln Tyr His Arg Ser Pro Pro Thr Phe Gly Gly Gly Thr Lys Leu Glu
        115                 120                 125

Ile Lys Arg
    130

<210> SEQ ID NO 3
<211> LENGTH: 11
<212> TYPE: PRT
<213> ORGANISM: Mus musculus

<400> SEQUENCE: 3

Lys Ala Ser Glu Asn Val Val Thr Tyr Val Ser
1               5                   10

<210> SEQ ID NO 4
<211> LENGTH: 12
<212> TYPE: PRT
<213> ORGANISM: Mus musculus

<400> SEQUENCE: 4

Thr Ala Ser Ser Ser Val Ser Ser Ser Tyr Leu Tyr
1               5                   10

<210> SEQ ID NO 5
<211> LENGTH: 6
<212> TYPE: PRT
<213> ORGANISM: Mus musculus

<400> SEQUENCE: 5

Gly Ala Ser Asn Arg Tyr
1               5

<210> SEQ ID NO 6
<211> LENGTH: 7
<212> TYPE: PRT
<213> ORGANISM: Mus musculus

<400> SEQUENCE: 6

Ser Thr Ser Asn Leu Ala Ser
1               5

<210> SEQ ID NO 7
<211> LENGTH: 9
<212> TYPE: PRT
<213> ORGANISM: Mus musculus

<400> SEQUENCE: 7

Gly Gln Gly Tyr Ser Tyr Pro Tyr Thr
1               5

<210> SEQ ID NO 8
<211> LENGTH: 9
<212> TYPE: PRT
<213> ORGANISM: Mus musculus

<400> SEQUENCE: 8

His Gln Tyr His Arg Ser Pro Pro Thr
1               5

<210> SEQ ID NO 9
<211> LENGTH: 140
<212> TYPE: PRT
<213> ORGANISM: Mus musculus

<400> SEQUENCE: 9

Met Ala Val Leu Gly Leu Leu Phe Cys Leu Val Thr Phe Pro Ser Cys
1               5                   10                  15

Val Leu Ser Gln Val Gln Leu Glu Gln Ser Gly Pro Gly Leu Val Gln
            20                  25                  30

Pro Ser Gln Ser Leu Ser Ile Thr Cys Thr Val Ser Gly Phe Ser Phe
        35                  40                  45

Thr Pro Tyr Gly Val His Trp Val Arg Gln Ser Pro Gly Lys Gly Leu
    50                  55                  60

Glu Trp Leu Gly Val Ile Trp Ser Gly Gly Asn Thr Asp Tyr Asn Ala
65                  70                  75                  80

Ala Phe Ile Ser Arg Leu Ser Ile Asn Lys Asp Asn Ser Lys Ser Gln
                85                  90                  95

```
Val Phe Phe Lys Met Asn Ser Leu Gln Val Asn Asp Thr Ala Ile Tyr
                100                 105                 110

Tyr Cys Ala Arg Asn Pro Arg Pro Gly Asn Tyr Phe Tyr Gly Met Asp
        115                 120                 125

Tyr Trp Gly Gln Gly Thr Ser Val Thr Val Ser Ser
    130                 135                 140

<210> SEQ ID NO 10
<211> LENGTH: 10
<212> TYPE: PRT
<213> ORGANISM: Mus musculus

<400> SEQUENCE: 10

Gly Phe Ser Phe Thr Pro Tyr Gly Val His
1               5                   10

<210> SEQ ID NO 11
<211> LENGTH: 14
<212> TYPE: PRT
<213> ORGANISM: Mus musculus

<400> SEQUENCE: 11

Trp Ser Gly Gly Asn Thr Asp Tyr Asn Ala Ala Phe Ile Ser
1               5                   10

<210> SEQ ID NO 12
<211> LENGTH: 13
<212> TYPE: PRT
<213> ORGANISM: Mus musculus

<400> SEQUENCE: 12

Asn Pro Arg Pro Gly Asn Tyr Pro Tyr Gly Met Asp Tyr
1               5                   10

<210> SEQ ID NO 13
<211> LENGTH: 42
<212> TYPE: DNA
<213> ORGANISM: Artificial Sequence
<220> FEATURE:
<223> OTHER INFORMATION: Primer

<400> SEQUENCE: 13
ggaattccag gaggaattta aaatgcatga gggagtccac ag                          42

<210> SEQ ID NO 14
<211> LENGTH: 26
<212> TYPE: DNA
<213> ORGANISM: Artificial Sequence
<220> FEATURE:
<223> OTHER INFORMATION: Primer

<400> SEQUENCE: 14
cgggatccca ggtgtctggg gttacc                                            26

<210> SEQ ID NO 15
<211> LENGTH: 109
<212> TYPE: PRT
<213> ORGANISM: Homo sapiens

<400> SEQUENCE: 15

Glu Ile Val Leu Thr Gln Ser Pro Val Thr Leu Ser Leu Ser Pro Gly
1               5                   10                  15

Glu Arg Ala Thr Leu Ser Cys Arg Ala Ser Gln Ser Val Ser Ser Tyr
            20                  25                  30
```

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Met Tyr
                 85                  90                  95

Thr Phe Gly Gln Gly Thr Lys Leu Glu Ile Lys Arg Thr
            100                 105

<210> SEQ ID NO 16
<211> LENGTH: 327
<212> TYPE: DNA
<213> ORGANISM: Homo sapiens

<400> SEQUENCE: 16
gaaattgtgt tgacacagtc tccagtcacc ctgtctttgt ctccagggga aagagccacc      60
ctctcctgca gggccagtca gagtgttagc agctacttag cctggtacca acagaaacct     120
ggccaggctc ccaggctcct catctatgat gcatccaaca gggccactgg catcccagcc     180
aggttcagtg gcagtgggtc tgggacagac ttcactctca ccatcagcag cctagagcct     240
gaagattttg cagtttatta ttgtcagcag cgtagcaact ggatgtacac ttttggccag     300
gggaccaagc tggagatcaa acgaact                                         327

<210> SEQ ID NO 17
<211> LENGTH: 123
<212> TYPE: PRT
<213> ORGANISM: Homo sapiens

<400> SEQUENCE: 17

Gln Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Phe Tyr
                 20                  25                  30

Ala Ile Ser Trp Val Arg Gln Ala Pro Gly Gln Gly Leu Glu Trp Met
            35                  40                  45

Gly Gly Phe Ile Pro Ile Phe Gly Ala Ala Asn Tyr Ala Gln Lys Phe
 50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Asp Asp Thr Ala Val Tyr Tyr Cys
                 85                  90                  95

Ala Arg Ile Pro Ser Gly Ser Tyr Tyr Tyr Asp Tyr Asp Met Asp Val
            100                 105                 110

Trp Gly Gln Gly Thr Thr Val Thr Val Ser Ser
            115                 120

<210> SEQ ID NO 18
<211> LENGTH: 369
<212> TYPE: DNA
<213> ORGANISM: Homo sapiens

<400> SEQUENCE: 18
caggtccagc tggtgcagtc tggggctgag gtgaagaagc ctgggtcctc ggtgaaggtc      60
tcctgcaagg cttctggagg caccttcagt ttctatgcta tcagctgggt gcgacaggcc     120

```
cctggacaag ggcttgagtg gatgggaggg ttcatccta tctttggtgc agcaaactac    180
gcacagaagt tccagggcag agtcacgatt accgcggacg aatccacgag cacagcctac   240
atggaactga gcagcctgag atctgacgac acggccgtgt attactgtgc gagaatccct   300
agtgggagct actactacga ctacgatatg gacgtctggg gccaagggac cacggtcacc   360
gtctcctca                                                           369
```

<210> SEQ ID NO 19
<211> LENGTH: 121
<212> TYPE: PRT
<213> ORGANISM: Mus musculus

<400> SEQUENCE: 19

```
Gln Val Gln Leu Glu Gln Ser Gly Pro Gly Leu Val Gln Pro Ser Gln
1               5                   10                  15

Ser Leu Ser Ile Thr Cys Thr Val Ser Gly Phe Ser Phe Thr Pro Tyr
            20                  25                  30

Gly Val His Trp Val Arg Gln Ser Pro Gly Lys Gly Leu Gly Trp Leu
        35                  40                  45

Gly Val Ile Trp Ser Gly Gly Asn Thr Asp Tyr Asn Ala Ala Phe Ile
    50                  55                  60

Ser Arg Leu Ser Ile Asn Lys Asp Asn Ser Lys Ser Gln Val Phe Phe
65                  70                  75                  80

Lys Met Asn Ser Leu Gln Val Asn Asp Thr Ala Ile Tyr Tyr Cys Ala
                85                  90                  95

Arg Asn Pro Arg Pro Gly Asn Tyr Pro Tyr Gly Met Asp Tyr Trp Gly
            100                 105                 110

Gln Gly Thr Ser Val Thr Val Ser Ser
        115                 120
```

<210> SEQ ID NO 20
<211> LENGTH: 121
<212> TYPE: PRT
<213> ORGANISM: Mus musculus

<400> SEQUENCE: 20

```
Glu Val Gln Leu Gln Gln Ser Gly Thr Val Leu Ala Arg Pro Gly Ala
1               5                   10                  15

Ser Val Lys Met Ser Cys Lys Ala Ser Gly Tyr Thr Phe Thr Ser Tyr
            20                  25                  30

Trp Met His Trp Met Lys Gln Arg Pro Gly Gln Gly Leu Glu Trp Ile
        35                  40                  45

Gly Thr Ile Tyr Pro Gly Asn Ser Asp Thr Asn Tyr Asn Gln Lys Phe
    50                  55                  60

Lys Gly Lys Ala Lys Leu Thr Ala Val Thr Ser Thr Asn Thr Ala Tyr
65                  70                  75                  80

Met Ala Leu Ser Ser Leu Thr Asn Glu Asp Ser Ala Val Tyr Tyr Cys
                85                  90                  95

Ser Arg Pro Thr Thr Ala Thr Arg Ser Ser Ala Met Asp Tyr Trp Gly
            100                 105                 110

Gln Gly Thr Ser Val Thr Val Ser Ser
        115                 120
```

<210> SEQ ID NO 21
<211> LENGTH: 108
<212> TYPE: PRT
<213> ORGANISM: Mus musculus

<400> SEQUENCE: 21

Asn Ile Val Met Thr Gln Ser Pro Lys Ser Met Ser Met Ser Val Gly
1               5                   10                  15

Glu Arg Val Thr Leu Thr Cys Lys Ala Ser Glu Asn Val Val Thr Tyr
            20                  25                  30

Val Ser Trp Tyr Gln Gln Lys Pro Glu Gln Ser Pro Lys Leu Leu Ile
        35                  40                  45

Tyr Gly Ala Ser Asn Arg Tyr Thr Gly Val Pro Asp Arg Phe Thr Gly
    50                  55                  60

Ser Gly Ser Ala Thr Asp Phe Thr Leu Thr Ile Ser Ser Val Gln Ala
65                  70                  75                  80

Glu Asp Leu Ala Asp Tyr His Cys Gly Gln Gly Tyr Ser Tyr Pro Tyr
                85                  90                  95

Thr Phe Gly Gly Gly Thr Lys Leu Glu Ile Lys Arg
            100                 105

<210> SEQ ID NO 22
<211> LENGTH: 109
<212> TYPE: PRT
<213> ORGANISM: Mus musculus

<400> SEQUENCE: 22

Gln Ile Val Leu Thr Gln Ser Pro Ala Ser Met Ser Ala Ser Leu Gly
1               5                   10                  15

Glu Arg Val Thr Met Thr Cys Thr Ala Ser Ser Ser Val Ser Ser Ser
            20                  25                  30

Tyr Leu Tyr Trp Tyr Gln Gln Lys Pro Gly Ser Ser Pro Lys Leu Trp
        35                  40                  45

Ile Tyr Ser Thr Ser Asn Leu Ala Ser Gly Val Pro Ala Arg Phe Ser
    50                  55                  60

Gly Ser Gly Ser Gly Thr Ser Tyr Ser Leu Thr Ile Ser Ser Met Glu
65                  70                  75                  80

Ala Glu Asp Ala Ala Thr Tyr Tyr Cys His Gln Tyr His Arg Ser Pro
                85                  90                  95

Pro Thr Phe Gly Gly Gly Thr Lys Leu Glu Ile Lys Arg
            100                 105

<210> SEQ ID NO 23
<211> LENGTH: 224
<212> TYPE: PRT
<213> ORGANISM: Homo sapiens
<220> FEATURE:
<221> NAME/KEY: Xaa
<222> LOCATION: (16)..(16)
<223> OTHER INFORMATION: Xaa is Pro or Leu
<220> FEATURE:
<221> NAME/KEY: Xaa
<222> LOCATION: (16)..(16)
<223> OTHER INFORMATION: Xaa is Pro or Arg
<220> FEATURE:
<221> NAME/KEY: Xaa
<222> LOCATION: (114)..(114)
<223> OTHER INFORMATION: Xaa is Pro or Leu

<400> SEQUENCE: 23

His Glu Gly Val His Arg Lys Pro Ser Leu Leu Ala His Pro Gly Xaa
1               5                   10                  15

Leu Val Lys Ser Glu Glu Thr Val Ile Leu Gln Cys Trp Ser Asp Val
            20                  25                  30

```
Met Phe Glu His Phe Leu Leu His Arg Glu Met Phe Asn Asp Thr
         35                  40                  45

Leu Arg Leu Ile Gly Glu His His Asp Gly Val Ser Lys Ala Asn Phe
 50                  55                  60

Ser Ile Ser Arg Met Thr Gln Asp Leu Ala Gly Thr Tyr Arg Cys Tyr
 65                  70                  75                  80

Gly Ser Val Thr His Ser Pro Tyr Gln Val Ser Ala Pro Ser Asp Pro
                 85                  90                  95

Leu Asp Ile Val Ile Ile Gly Leu Tyr Glu Lys Pro Ser Leu Ser Ala
                100                 105                 110

Gln Xaa Gly Pro Thr Val Leu Ala Gly Glu Asn Val Thr Leu Ser Cys
            115                 120                 125

Ser Ser Arg Ser Ser Tyr Asp Met Tyr His Leu Ser Arg Glu Gly Glu
130                 135                 140

Ala His Glu Arg Arg Leu Pro Ala Gly Pro Lys Val Asn Gly Thr Phe
145                 150                 155                 160

Gln Ala Asp Phe Pro Leu Gly Pro Ala Thr His Gly Gly Thr Tyr Arg
                165                 170                 175

Cys Phe Gly Ser Phe His Asp Ser Pro Tyr Glu Trp Ser Lys Ser Ser
                180                 185                 190

Asp Pro Leu Leu Val Ser Val Thr Gly Asn Pro Ser Asn Ser Trp Pro
            195                 200                 205

Ser Pro Thr Glu Pro Ser Ser Lys Thr Gly Asn Pro Arg His Leu His
210                 215                 220

<210> SEQ ID NO 24
<211> LENGTH: 224
<212> TYPE: PRT
<213> ORGANISM: Homo sapiens

<400> SEQUENCE: 24

His Glu Gly Val His Arg Lys Pro Ser Leu Leu Ala His Pro Gly Arg
 1               5                  10                  15

Leu Val Lys Ser Glu Glu Thr Val Ile Leu Gln Cys Trp Ser Asp Val
                 20                  25                  30

Arg Phe Glu His Phe Leu Leu His Arg Glu Gly Lys Phe Lys Asp Thr
             35                  40                  45

Leu His Leu Ile Gly Glu His His Asp Gly Val Ser Lys Ala Asn Phe
 50                  55                  60

Ser Ile Gly Pro Met Met Gln Asp Leu Ala Gly Thr Tyr Arg Cys Tyr
 65                  70                  75                  80

Gly Ser Val Thr His Ser Pro Tyr Gln Leu Ser Ala Pro Ser Asp Pro
                 85                  90                  95

Leu Asp Ile Val Ile Thr Gly Leu Tyr Glu Lys Pro Ser Leu Ser Ala
                100                 105                 110

Gln Pro Gly Pro Thr Val Leu Ala Gly Glu Ser Val Thr Leu Ser Cys
            115                 120                 125

Ser Ser Arg Ser Ser Tyr Asp Met Tyr His Leu Ser Arg Glu Gly Glu
130                 135                 140

Ala His Glu Cys Arg Phe Ser Ala Gly Pro Lys Val Asn Gly Thr Phe
145                 150                 155                 160

Gln Ala Asp Phe Pro Leu Gly Pro Ala Thr His Gly Gly Tyr Tyr Arg
                165                 170                 175

Cys Phe Gly Ser Phe Arg Asp Ser Pro Tyr Glu Trp Ser Asn Ser Ser
                180                 185                 190
```

Asp Pro Leu Leu Val Ser Val Ile Gly Asn Pro Ser Asn Ser Trp Pro
            195                 200                 205

Ser Pro Thr Glu Pro Ser Ser Lys Thr Gly Asn Pro Arg His Leu His
            210                 215                 220

<210> SEQ ID NO 25
<211> LENGTH: 224
<212> TYPE: PRT
<213> ORGANISM: Homo sapiens

<400> SEQUENCE: 25

His Gly Gly Val His Arg Lys Pro Ser Leu Leu Ala His Pro Gly Pro
1               5                   10                  15

Leu Val Lys Ser Glu Glu Thr Val Ile Leu Gln Cys Trp Ser Asp Val
            20                  25                  30

Arg Phe Gln His Phe Leu Leu His Arg Glu Gly Lys Phe Lys Asp Thr
        35                  40                  45

Leu His Leu Ile Gly Glu His His Asp Gly Val Ser Lys Ala Asn Phe
    50                  55                  60

Ser Ile Gly Pro Met Met Gln Asp Leu Ala Gly Thr Tyr Arg Cys Tyr
65                  70                  75                  80

Gly Ser Val Thr His Ser Pro Tyr Gln Leu Ser Ala Pro Ser Asp Pro
                85                  90                  95

Leu Asp Ile Val Ile Thr Gly Leu Tyr Glu Lys Pro Ser Leu Ser Ala
            100                 105                 110

Gln Pro Gly Pro Thr Val Leu Ala Gly Glu Ser Val Thr Leu Ser Cys
        115                 120                 125

Ser Ser Arg Ser Ser Tyr Asp Met Tyr His Leu Ser Arg Glu Gly Glu
    130                 135                 140

Ala His Glu Arg Arg Phe Ser Ala Gly Pro Lys Val Asn Gly Thr Phe
145                 150                 155                 160

Gln Ala Asp Phe Pro Leu Gly Pro Ala Thr His Gly Gly Thr Tyr Arg
                165                 170                 175

Cys Phe Gly Ser Phe Arg Asp Ser Pro Tyr Glu Trp Ser Asn Ser Ser
            180                 185                 190

Asp Pro Leu Leu Val Ser Val Thr Gly Asn Pro Ser Asn Ser Trp Pro
        195                 200                 205

Ser Pro Thr Glu Pro Ser Ser Glu Thr Gly Asn Pro Arg His Leu His
    210                 215                 220

<210> SEQ ID NO 26
<211> LENGTH: 45
<212> TYPE: DNA
<213> ORGANISM: Artificial Sequence
<220> FEATURE:
<223> OTHER INFORMATION: Primer

<400> SEQUENCE: 26
ctaatacgac tcactatagg gcaagcagtg gtatcaacgc agagt          45

<210> SEQ ID NO 27
<211> LENGTH: 21
<212> TYPE: DNA
<213> ORGANISM: Artificial Sequence
<220> FEATURE:
<223> OTHER INFORMATION: Primer

<400> SEQUENCE: 27
ctaatacgac tcactatagg g          21

<210> SEQ ID NO 28
<211> LENGTH: 32
<212> TYPE: DNA
<213> ORGANISM: Artificial Sequence
<220> FEATURE:
<223> OTHER INFORMATION: Primer

<400> SEQUENCE: 28
gcaggcacac aacagaggca gttccagatt tc                                32

<210> SEQ ID NO 29
<211> LENGTH: 45
<212> TYPE: DNA
<213> ORGANISM: Artificial Sequence
<220> FEATURE:
<223> OTHER INFORMATION: Primer

<400> SEQUENCE: 29
ctaatacgac tcactatagg gcaagcagtg gtatcaacgc agagt                  45

<210> SEQ ID NO 30
<211> LENGTH: 21
<212> TYPE: DNA
<213> ORGANISM: Artificial Sequence
<220> FEATURE:
<223> OTHER INFORMATION: Primer

<400> SEQUENCE: 30
ctaatacgac tcactatagg g                                            21

<210> SEQ ID NO 31
<211> LENGTH: 23
<212> TYPE: DNA
<213> ORGANISM: Artificial Sequence
<220> FEATURE:
<223> OTHER INFORMATION: Primer

<400> SEQUENCE: 31
gtgccagggg gaagaccgat ggg                                          23

<210> SEQ ID NO 32
<211> LENGTH: 16
<212> TYPE: DNA
<213> ORGANISM: Artificial Sequence
<220> FEATURE:
<223> OTHER INFORMATION: Primer

<400> SEQUENCE: 32
gtaaaacgac ggccag                                                  16

<210> SEQ ID NO 33
<211> LENGTH: 17
<212> TYPE: DNA
<213> ORGANISM: Artificial Sequence
<220> FEATURE:
<223> OTHER INFORMATION: Primer

<400> SEQUENCE: 33
caggaaacag ctatgac                                                 17

<210> SEQ ID NO 34
<211> LENGTH: 108
<212> TYPE: PRT
<213> ORGANISM: Homo sapiens -continued

<400> SEQUENCE: 34

Val Val Met Thr Gln Ser Pro Ser Thr Leu Ser Ala Ser Val Gly Asp
1               5                   10                  15

Thr Ile Thr Ile Thr Cys Arg Ala Ser Gln Ser Ile Glu Thr Trp Leu
            20                  25                  30

Ala Trp Tyr Gln Gln Lys Pro Gly Lys Ala Pro Lys Leu Leu Ile Tyr
        35                  40                  45

Lys Ala Ser Thr Leu Lys Thr Gly Val Pro Ser Arg Phe Ser Gly Ser
    50                  55                  60

Gly Ser Gly Thr Glu Phe Thr Leu Thr Ile Ser Gly Leu Gln Phe Asp
65                  70                  75                  80

Asp Phe Ala Thr Tyr His Cys Gln His Tyr Ala Gly Tyr Ser Ala Thr
                85                  90                  95

Phe Gly Gln Gly Thr Arg Val Glu Ile Lys Arg Thr
            100                 105

<210> SEQ ID NO 35
<211> LENGTH: 119
<212> TYPE: PRT
<213> ORGANISM: Homo sapiens

<400> SEQUENCE: 35

Gly Val Gln Leu Val Glu Ser Gly Gly Leu Val Lys Ala Gly Gly
1               5                   10                  15

Ser Leu Ile Leu Ser Cys Gly Val Ser Asn Phe Arg Ile Ser Ala His
            20                  25                  30

Thr Met Asn Trp Val Arg Arg Val Pro Gly Gly Gly Leu Glu Trp Val
        35                  40                  45

Ala Ser Ile Ser Thr Ser Ser Thr Tyr Arg Asp Tyr Ala Asp Ala Val
    50                  55                  60

Lys Gly Arg Phe Thr Val Ser Arg Asp Leu Glu Asp Phe Val Tyr
65                  70                  75                  80

Leu Gln Met His Lys Met Arg Val Glu Asp Thr Ala Ile Tyr Tyr Cys
                85                  90                  95

Ala Arg Lys Gly Ser Asp Arg Leu Ser Asp Asn Asp Pro Phe Asp Ala
            100                 105                 110

Trp Gly Pro Gly Thr Val Val
        115

<210> SEQ ID NO 36
<211> LENGTH: 214
<212> TYPE: PRT
<213> ORGANISM: Homo sapiens

<400> SEQUENCE: 36

Glu Ile Val Leu Thr Gln Ser Pro Val Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

```
Glu Asp Phe Ala Val Tyr Tyr Cys Gln Gln Arg Ser Asn Trp Met Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
            210

<210> SEQ ID NO 37
<211> LENGTH: 450
<212> TYPE: PRT
<213> ORGANISM: Homo sapiens

<400> SEQUENCE: 37

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Phe Tyr
            20                  25                  30

Ala Ile Ser Trp Val Arg Gln Ala Pro Gly Gln Gly Leu Glu Trp Met
        35                  40                  45

Gly Gly Phe Ile Pro Ile Phe Gly Ala Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Asp Asp Thr Ala Val Tyr Tyr Cys
                85                  90                  95

Ala Arg Ile Pro Ser Gly Ser Tyr Tyr Tyr Asp Tyr Asp Met Asp Val
            100                 105                 110

Trp Gly Gln Gly Thr Thr Val Thr Val Ser Ser Ala Ser Thr Lys Gly
            115                 120                 125

Pro Ser Val Phe Pro Leu Ala Pro Cys Ser Arg Ser Thr Ser Glu Ser
130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
            195                 200                 205

Asp His Lys Pro Ser Asn Thr Lys Val Asp Lys Arg Val Glu Ser Lys
            210                 215                 220

Tyr Gly Pro Pro Cys Pro Ser Cys Pro Ala Pro Glu Phe Leu Gly Gly
225                 230                 235                 240
```

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser Gln Glu
        260                 265                 270

Asp Pro Glu Val Gln Phe Asn Trp Tyr Val Asp Gly Val Glu Val His
    275                 280                 285

Asn Ala Lys Thr Lys Pro Arg Glu Gln Gln Phe Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
            325                 330                 335

Lys Thr Ile Ser Lys Ala Lys Gly Gln Pro Arg Glu Pro Gln Val Tyr
        340                 345                 350

Thr Leu Pro Pro Ser Gln Glu Glu Met Thr Lys Asn Gln Val Ser Leu
    355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
            405                 410                 415

Lys Ser Arg Trp Gln Glu Gly Asn Val Phe Ser Cys Ser Val Met His
        420                 425                 430

Glu Ala Leu His Asn His Tyr Thr Gln Lys Ser Leu Ser Leu Ser Leu
    435                 440                 445

Gly Lys
    450

<210> SEQ ID NO 38
<211> LENGTH: 100
<212> TYPE: PRT
<213> ORGANISM: Homo sapiens

<400> SEQUENCE: 38

Gln Gly Gly Val His Arg Lys Pro Ser Phe Leu Ala Leu Pro Gly His
1               5                   10                  15

Leu Val Lys Ser Glu Glu Thr Val Ile Leu Gln Cys Trp Ser Asp Val
            20                  25                  30

Met Phe Glu His Phe Leu Leu His Arg Glu Gly Lys Phe Asn Asn Thr
        35                  40                  45

Leu His Leu Ile Gly Glu His His Asp Gly Val Ser Lys Ala Asn Phe
    50                  55                  60

Ser Ile Gly Pro Met Met Pro Val Leu Ala Gly Thr Tyr Arg Cys Tyr
65                  70                  75                  80

Gly Ser Val Pro His Ser Pro Tyr Gln Leu Ser Ala Pro Ser Asp Pro
            85                  90                  95

Leu Asp Met Val
        100

<210> SEQ ID NO 39
<211> LENGTH: 109
<212> TYPE: PRT
<213> ORGANISM: Homo sapiens

```
<220> FEATURE:
<221> NAME/KEY: Xaa
<222> LOCATION: (3)..(3)
<223> OTHER INFORMATION: Q or R
<220> FEATURE:
<221> NAME/KEY: Xaa
<222> LOCATION: (4)..(4)
<223> OTHER INFORMATION: L or M
<220> FEATURE:
<221> NAME/KEY: Xaa
<222> LOCATION: (9)..(9)
<223> OTHER INFORMATION: S or F
<220> FEATURE:
<221> NAME/KEY: misc_feature
<222> LOCATION: (23)..(23)
<223> OTHER INFORMATION: Xaa can be any naturally occurring amino acid
<220> FEATURE:
<221> NAME/KEY: Xaa
<222> LOCATION: (24)..(24)
<223> OTHER INFORMATION: R or W
<220> FEATURE:
<221> NAME/KEY: Xaa
<222> LOCATION: (32)..(32)
<223> OTHER INFORMATION: A or Y
<220> FEATURE:
<221> NAME/KEY: Xaa
<222> LOCATION: (41)..(41)
<223> OTHER INFORMATION: G or A
<220> FEATURE:
<221> NAME/KEY: Xaa
<222> LOCATION: (47)..(47)
<223> OTHER INFORMATION: L or F
<220> FEATURE:
<221> NAME/KEY: Xaa
<222> LOCATION: (50)..(50)
<223> OTHER INFORMATION: D or Y
<220> FEATURE:
<221> NAME/KEY: Xaa
<222> LOCATION: (55)..(55)
<223> OTHER INFORMATION: E or Q
<220> FEATURE:
<221> NAME/KEY: Xaa
<222> LOCATION: (71)..(71)
<223> OTHER INFORMATION: F or Y
<220> FEATURE:
<221> NAME/KEY: Xaa
<222> LOCATION: (74)..(74)
<223> OTHER INFORMATION: A or T

<400> SEQUENCE: 39

Ala Ile Xaa Xaa Thr Gln Ser Pro Xaa Ser Leu Ser Ala Ser Val Gly
1               5                   10                  15

Asp Arg Val Thr Ile Thr Xaa Xaa Ala Ser Gln Gly Ile Ser Ser Xaa
                20                  25                  30

Leu Ala Trp Tyr Gln Gln Lys Pro Xaa Lys Ala Pro Lys Leu Xaa Ile
            35                  40                  45

Tyr Xaa Ala Ser Ser Leu Xaa Ser Gly Val Pro Ser Arg Phe Ser Gly
    50                  55                  60

Ser Gly Ser Gly Tyr Asp Xaa Thr Leu Xaa Ile Ser Ser Leu Gln Pro
65                  70                  75                  80

Glu Asp Phe Ala Thr Tyr Tyr Cys Gln Gln Tyr Tyr Ser Thr Pro Leu
                85                  90                  95

Thr Phe Gly Gly Gly Thr Lys Val Glu Ile Lys Arg Thr
                100                 105

<210> SEQ ID NO 40
<211> LENGTH: 327
<212> TYPE: DNA
<213> ORGANISM: Homo sapiens
```

-continued

```
<220> FEATURE:
<221> NAME/KEY: n
<222> LOCATION: (8)..(8)
<223> OTHER INFORMATION: a or g
<220> FEATURE:
<221> NAME/KEY: n
<222> LOCATION: (8)..(8)
<223> OTHER INFORMATION: a or g
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: n
<222> LOCATION: (10)..(10)
<223> OTHER INFORMATION: t or a
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: n
<222> LOCATION: (26)..(26)
<223> OTHER INFORMATION: c or t
<220> FEATURE:
<221> NAME/KEY: n
<222> LOCATION: (26)..(26)
<223> OTHER INFORMATION: c or t
<220> FEATURE:
<221> NAME/KEY: misc_feature
<222> LOCATION: (26)..(26)
<223> OTHER INFORMATION: n is a, c, g, or t
<220> FEATURE:
<221> NAME/KEY: n
<222> LOCATION: (70)..(70)
<223> OTHER INFORMATION: c or t
<220> FEATURE:
<221> NAME/KEY: misc_feature
<222> LOCATION: (70)..(70)
<223> OTHER INFORMATION: n is a, c, g, or t
<220> FEATURE:
<221> NAME/KEY: n
<222> LOCATION: (75)..(75)
<223> OTHER INFORMATION: a or c
<220> FEATURE:
<221> NAME/KEY: misc_feature
<222> LOCATION: (75)..(75)
<223> OTHER INFORMATION: n is a, c, g, or t
<220> FEATURE:
<221> NAME/KEY: n
<222> LOCATION: (94)..(94)
<223> OTHER INFORMATION: g or t
<220> FEATURE:
<221> NAME/KEY: misc_feature
<222> LOCATION: (94)..(95)
<223> OTHER INFORMATION: n is a, c, g, or t
<220> FEATURE:
<221> NAME/KEY: n
<222> LOCATION: (95)..(95)
<223> OTHER INFORMATION: c or a
<220> FEATURE:
<221> NAME/KEY: n
<222> LOCATION: (114)..(114)
<223> OTHER INFORMATION: g or a
<220> FEATURE:
<221> NAME/KEY: misc_feature
<222> LOCATION: (114)..(114)
<223> OTHER INFORMATION: n is a, c, g, or t
<220> FEATURE:
<221> NAME/KEY: n
<222> LOCATION: (122)..(122)
<223> OTHER INFORMATION: g or c
<220> FEATURE:
<221> NAME/KEY: misc_feature
<222> LOCATION: (122)..(123)
<223> OTHER INFORMATION: n is a, c, g, or t
```

```
<220> FEATURE:
<221> NAME/KEY: n
<222> LOCATION: (123)..(123)
<223> OTHER INFORMATION: g or a
<220> FEATURE:
<221> NAME/KEY: n
<222> LOCATION: (129)..(129)
<223> OTHER INFORMATION: t or c
<220> FEATURE:
<221> NAME/KEY: misc_feature
<222> LOCATION: (129)..(129)
<223> OTHER INFORMATION: n is a, c, g, or t
<220> FEATURE:
<221> NAME/KEY: n
<222> LOCATION: (139)..(139)
<223> OTHER INFORMATION: c or t
<220> FEATURE:
<221> NAME/KEY: misc_feature
<222> LOCATION: (139)..(139)
<223> OTHER INFORMATION: n is a, c, g, or t
<220> FEATURE:
<221> NAME/KEY: n
<222> LOCATION: (141)..(141)
<223> OTHER INFORMATION: g or c
<220> FEATURE:
<221> NAME/KEY: misc_feature
<222> LOCATION: (141)..(141)
<223> OTHER INFORMATION: n is a, c, g, or t
<220> FEATURE:
<221> NAME/KEY: n
<222> LOCATION: (148)..(148)
<223> OTHER INFORMATION: g or t
<220> FEATURE:
<221> NAME/KEY: misc_feature
<222> LOCATION: (148)..(148)
<223> OTHER INFORMATION: n is a, c, g, or t
<220> FEATURE:
<221> NAME/KEY: n
<222> LOCATION: (153)..(153)
<223> OTHER INFORMATION: c or a
<220> FEATURE:
<221> NAME/KEY: misc_feature
<222> LOCATION: (153)..(153)
<223> OTHER INFORMATION: n is a, c, g, or t
<220> FEATURE:
<221> NAME/KEY: misc_feature
<222> LOCATION: (162)..(163)
<223> OTHER INFORMATION: n is a, c, g, or t
<220> FEATURE:
<221> NAME/KEY: misc_feature
<222> LOCATION: (207)..(207)
<223> OTHER INFORMATION: n is a, c, g, or t
<220> FEATURE:
<221> NAME/KEY: misc_feature
<222> LOCATION: (212)..(212)
<223> OTHER INFORMATION: n is a, c, g, or t
<220> FEATURE:
<221> NAME/KEY: misc_feature
<222> LOCATION: (220)..(220)
<223> OTHER INFORMATION: n is a, c, g, or t

<400> SEQUENCE: 40
gccatccngn tgacccagtc tccatnctcc ctgtctgcat ctgtaggaga cagagtcacc      60
atcacttgcn gggcnagtca gggcattagc agtnntttag cctggtatca gcanaaacca     120
gnnaaagcnc ctaagctcnt natctatnat gcntccagtt tnnaaagtgg ggtcccatca     180
aggttcagcg gcagtggatc tgggacngat tncactctcn ccatcagcag cctgcagcct     240
gaagattttg caacttatta ctgtcaacag tattatagta ccccgctcac tttcggcgga     300
gggaccaagg tggagatcaa acgaact                                         327
```

<210> SEQ ID NO 41
<211> LENGTH: 124
<212> TYPE: PRT
<213> ORGANISM: Homo sapiens

<400> SEQUENCE: 41

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Ser Asn Ser Tyr
            20                  25                  30

Ser Ile Asn Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Ser Ala Asp Glu Ser Thr Arg Thr Val Tyr
65                  70                  75                  80

Met Glu Leu Asn Ser Leu Arg Ser Glu Asp Thr Ala Val Tyr Tyr Cys
                85                  90                  95

Ala Arg Gly Tyr Tyr Asp Ile Phe Lys Asp Tyr Tyr Gly Met Asp
            100                 105                 110

Val Trp Gly Gln Gly Thr Thr Val Thr Val Ser Ser
        115                 120
```

<210> SEQ ID NO 42
<211> LENGTH: 372
<212> TYPE: DNA
<213> ORGANISM: Homo sapiens

<400> SEQUENCE: 42

```
caggtccagc tggtgcagtc tggggctgag gttaagaagc ctgggtcctc ggtgaaggtc    60
tcctgcaagg cttctggagg cacctccaac agctattcta ttaactgggt gcgacaggcc   120
cctggacaag gcttgagtg gatgggaggg atcatcccta tatttggtac agcaaactac   180
gcacagaagt tccagggcag agtcacgatt tccgcggacg aatccacgcg cacagtctac   240
atggagctga acagtctgag atctgaggat acggccgtgt attactgtgc gagaggatat   300
tacgatattt tcaaggacta ctattacggt atggacgtct ggggccaagg gaccacggtc   360
accgtctcct ca                                                       372
```

<210> SEQ ID NO 43
<211> LENGTH: 6
<212> TYPE: PRT
<213> ORGANISM: Artificial Sequence
<220> FEATURE:
<223> OTHER INFORMATION: Antibody sequence

<400> SEQUENCE: 43

```
Val Val Thr Tyr Val Ser
1               5
```

<210> SEQ ID NO 44
<211> LENGTH: 12
<212> TYPE: PRT
<213> ORGANISM: Artificial Sequence
<220> FEATURE:
<223> OTHER INFORMATION: Antibody sequence

<400> SEQUENCE: 44

```
Thr Ala Ser Ser Ser Val Ser Ser Ser Tyr Leu Tyr
1               5                   10
```

```
<210> SEQ ID NO 45
<211> LENGTH: 7
<212> TYPE: PRT
<213> ORGANISM: Artificial Sequence
<220> FEATURE:
<223> OTHER INFORMATION: Antibody sequence

<400> SEQUENCE: 45

Gly Ala Ser Asn Arg Tyr Thr
1               5

<210> SEQ ID NO 46
<211> LENGTH: 7
<212> TYPE: PRT
<213> ORGANISM: Artificial Sequence
<220> FEATURE:
<223> OTHER INFORMATION: Antibody sequence

<400> SEQUENCE: 46

Ser Thr Ser Asn Leu Ala Ser
1               5

<210> SEQ ID NO 47
<211> LENGTH: 9
<212> TYPE: PRT
<213> ORGANISM: Artificial Sequence
<220> FEATURE:
<223> OTHER INFORMATION: Antibody sequence

<400> SEQUENCE: 47

Gly Gln Gly Tyr Ser Tyr Phe Tyr Thr
1               5

<210> SEQ ID NO 48
<211> LENGTH: 9
<212> TYPE: PRT
<213> ORGANISM: Artificial Sequence
<220> FEATURE:
<223> OTHER INFORMATION: Antibody sequence

<400> SEQUENCE: 48

His Gln Tyr His Arg Ser Pro Pro Thr
1               5

<210> SEQ ID NO 49
<211> LENGTH: 10
<212> TYPE: PRT
<213> ORGANISM: Artificial Sequence
<220> FEATURE:
<223> OTHER INFORMATION: Antibody sequence

<400> SEQUENCE: 49

Gly Phe Ser Phe Thr Phe Tyr Gly Val His
1               5                   10

<210> SEQ ID NO 50
<211> LENGTH: 16
<212> TYPE: PRT
<213> ORGANISM: Artificial Sequence
<220> FEATURE:
<223> OTHER INFORMATION: Antibody sequence

<400> SEQUENCE: 50

Val Ile Trp Ser Gly Gly Asn Thr Asp Tyr Asn Ala Ala Phe Ile Ser
1               5                   10                  15
```

<210> SEQ ID NO 51
<211> LENGTH: 13
<212> TYPE: PRT
<213> ORGANISM: Artificial Sequence
<220> FEATURE:
<223> OTHER INFORMATION: Antibody sequence

<400> SEQUENCE: 51

Asn Pro Arg Pro Gly Asn Tyr Pro Tyr Gly Met Asp Tyr
1               5                   10

<210> SEQ ID NO 52
<211> LENGTH: 10
<212> TYPE: PRT
<213> ORGANISM: Artificial Sequence
<220> FEATURE:
<223> OTHER INFORMATION: Antibody sequence

<400> SEQUENCE: 52

Gly Tyr Thr Phe Thr Ser Tyr Trp Met His
1               5                   10

<210> SEQ ID NO 53
<211> LENGTH: 16
<212> TYPE: PRT
<213> ORGANISM: Artificial Sequence
<220> FEATURE:
<223> OTHER INFORMATION: Antibody sequence

<400> SEQUENCE: 53

Thr Ile Tyr Pro Gly Asn Ser Asp Thr Asn Tyr Asn Gln Lys Phe Lys
1               5                   10                  15

<210> SEQ ID NO 54
<211> LENGTH: 12
<212> TYPE: PRT
<213> ORGANISM: Artificial Sequence
<220> FEATURE:
<223> OTHER INFORMATION: Antibody sequence

<400> SEQUENCE: 54

Pro Thr Thr Ala Thr Arg Ser Ser Ala Met Asp Tyr
1               5                   10

<210> SEQ ID NO 55
<211> LENGTH: 127
<212> TYPE: PRT
<213> ORGANISM: Artificial Sequence
<220> FEATURE:
<223> OTHER INFORMATION: Antibody sequence

<400> SEQUENCE: 55

Met Glu Ser Gln Thr Leu Val Phe Ile Ser Ile Leu Leu Trp Leu Tyr
1               5                   10                  15

Gly Ala Asp Gly Asn Ile Val Met Thr Gln Ser Pro Lys Ser Met Ser
                20                  25                  30

Met Ser Val Gly Glu Arg Val Thr Leu Thr Cys Lys Asn Ser Glu Asn
        35                  40                  45

Val Val Thr Tyr Val Ser Trp Tyr Gln Gln Lys Pro Glu Gln Ser Pro
    50                  55                  60

Lys Leu Leu Ile Tyr Gly Ala Ser Asn Arg Tyr Thr Gly Val Pro Asp
65                  70                  75                  80

Arg Phe Thr Gly Ser Gly Ser Ala Thr Asp Phe Thr Leu Thr Ile Ser
                85                  90                  95

Ser Val Gln Ala Glu Asp Leu Ala Asp Tyr His Cys Gly Gln Gly Tyr
            100                 105                 110

Ser Tyr Pro Tyr Thr Phe Gly Gly Thr Lys Leu Asp Ile Lys Arg
            115                 120                 125

<210> SEQ ID NO 56
<211> LENGTH: 131
<212> TYPE: PRT
<213> ORGANISM: Artificial Sequence
<220> FEATURE:
<223> OTHER INFORMATION: Antibody sequence

<400> SEQUENCE: 56

Met Asp Phe Gln Val Gln Ile Phe Ser Phe Leu Leu Ile Ser Ala Ser
1               5                   10                  15

Val Ile Met Ser Arg Gly Gln Ile Val Leu Thr Gln Ser Pro Ala Ser
            20                  25                  30

Met Ser Ala Ser Leu Gly Glu Arg Val Thr Met Thr Cys Thr Ala Ser
        35                  40                  45

Ser Ser Val Ser Ser Ser Tyr Leu Tyr Trp Tyr Gln Gln Lys Pro Gly
    50                  55                  60

Ser Ser Pro Lys Leu Trp Ile Tyr Ser Thr Ser Asn Leu Ala Ser Gly
65                  70                  75                  80

Val Pro Ala Arg Phe Ser Gly Ser Gly Ser Gly Thr Ser Tyr Ser Leu
                85                  90                  95

Thr Ile Ser Ser Met Gln Ala Glu Asp Ala Ala Thr Tyr Tyr Cys His
            100                 105                 110

Gln Tyr His Arg Ser Pro Pro Thr Phe Gly Gly Gly Thr Lys Leu Glu
        115                 120                 125

Ile Lys Arg
    130

<210> SEQ ID NO 57
<211> LENGTH: 140
<212> TYPE: PRT
<213> ORGANISM: Artificial Sequence
<220> FEATURE:
<223> OTHER INFORMATION: Antibody sequence

<400> SEQUENCE: 57

Met Ala Val Leu Gly Leu Leu Phe Cys Leu Val Thr Phe Pro Ser Cys
1               5                   10                  15

Val Leu Ser Gln Val Gln Leu Glu Gln Ser Gly Pro Gly Leu Val Gln
            20                  25                  30

Pro Ser Gln Ser Leu Ser Ile Thr Cys Thr Val Ser Gly Phe Ser Phe
        35                  40                  45

Thr Pro Tyr Gly Val His Trp Val Arg Gln Ser Pro Gly Lys Gly Leu
    50                  55                  60

Glu Trp Leu Gly Val Ile Trp Ser Gly Gly Asn Thr Asp Tyr Asn Ala
65                  70                  75                  80

Ala Phe Ile Ser Arg Leu Ser Ile Asn Lys Asp Asn Ser Lys Ser Gln
                85                  90                  95

Val Phe Phe Lys Met Asn Ser Leu Gln Val Asn Asp Thr Ala Ile Tyr
            100                 105                 110

Tyr Cys Ala Arg Asn Pro Arg Pro Gly Asn Tyr Pro Tyr Gly Met Asp
        115                 120                 125

Tyr Trp Gly Gln Gly Thr Ser Val Thr Val Ser Ser
    130                 135                 140

```
<210> SEQ ID NO 58
<211> LENGTH: 140
<212> TYPE: PRT
<213> ORGANISM: Artificial Sequence
<220> FEATURE:
<223> OTHER INFORMATION: Antibody sequence

<400> SEQUENCE: 58
```

Met Glu Cys Asn Trp Ile Leu Pro Phe Ile Leu Ser Val Thr Ser Gly
1               5                   10                  15

Val Tyr Ser Glu Val Gln Leu Gln Gln Ser Gly Thr Val Leu Ala Arg
            20                  25                  30

Pro Gly Ala Ser Val Lys Met Ser Cys Lys Ala Ser Gly Tyr Thr Phe
        35                  40                  45

Thr Ser Tyr Trp Met His Trp Met Lys Gln Arg Pro Gly Gln Gly Leu
    50                  55                  60

Glu Trp Ile Gly Thr Ile Tyr Pro Gly Asn Ser Asp Thr Asn Tyr Asn
65                  70                  75                  80

Gln Lys Phe Lys Gly Lys Ala Lys Leu Thr Ala Val Thr Ser Thr Asn
                85                  90                  95

Thr Ala Tyr Met Glu Leu Ser Ser Leu Thr Asn Glu Asp Ser Ala Val
            100                 105                 110

Tyr Tyr Cys Ser Arg Pro Thr Thr Ala Thr Arg Ser Ser Ala Met Asp
        115                 120                 125

Tyr Trp Gly Gln Gly Thr Ser Val Thr Val Ser Ser
    130                 135                 140

METHODS FOR TREATMENT OF RECURRENT HEMATOLOGICAL MALIGNANCIES

CROSS-REFERENCE TO RELATED APPLICATIONS

This application is the U.S. national stage (under 35 U.S.C. §371) of International Patent Application PCT/US2011/061840 (published as WO 2012/071411), filed Nov. 22, 2011, which designates the US, which claims priority to provisional application Ser. No. 61/415,973, filed on Nov. 22, 2010, the disclosure of which, including all sequence information, is incorporated by reference herein.

The biological sequence listing file named "44292o118602.txt" having a size of 43,342 bytes that was created May 15, 2013 is hereby incorporated by reference in its entirety.

FIELD OF THE INVENTION

This invention relates to the modulation of NK cell activity for the treatment of hematological malignancies.

BACKGROUND OF THE INVENTION

Natural killer (NK) cells are a subset of large granular lymphocytes that act as cytotoxic immune cells. The cytotoxic activity mediated by NK cells naturally against target cells (e.g., cancer cells, virally infected cells) is generally expressed a being the result of a "balance" of positive and negative signals transmitted respectively by activating and inhibitory cell surface receptors.

NK cells can be identified by any number of known cell surface markers which vary between species (e.g., in humans CD56, CD16, NKp44, NKp46, and NKp30 are often used; in mice NK1.1, Ly49A-W, CD49b are often used). In an active state, NK cells are capable of killing certain autologous, allogeneic, and even xenogeneic tumor cells, virus-infected cells, certain bacteria (e.g., *Salmonella typhi*), and other target cells. NK cells appear to preferentially kill target cells that express little or no Major Histocompatibility Class I ("MHCI" or "MHC-I") molecules on their surface. NK cells also kill target cells to which antibody molecules have attached, a mechanism known as antibody-dependent cellular cytotoxicity (ADCC). In action against target cells, NK cells can release pore-forming proteins called perforins, proteolytic enzymes called granzymes, and cytokines/chemokines (e.g., TNFα, IFNγ, etc.) that directly lead to target cell apoptosis or lysis, or that regulate other immune responses. Upon activation, NK cells also may express Fas ligand (FasL), enabling these cells to induce apoptosis in cells that express Fas.

Sufficient NK cell activity and NK cell count typically are both necessary to mounting an adequate NK cell-mediated immune response. NK cells may be present in normal numbers in an individual, but if not activated these cells will be ineffective in performing vital immune system functions, such as eliminating abnormal cells. Decreased NK cell activity is linked to the development and progression of many diseases. For example, research has demonstrated that low NK cell activity causes greater susceptibility to diseases such as chronic fatigue syndrome (CFS), viral infections, and the development of cancers.

NK cell activity is regulated by NK cell activity-modulating receptors ("NKCAMRs" or simply "AMRs"), which may be specific for various ligands such as MHC-I molecules, MHC-I homologs, or other biological molecules expressed on target cells. NK cells in an individual typically present a number of activating and inhibitory receptors. The activity of NK cells is regulated by a balance of signals transduced through these activating and inhibitory receptors. Each type of NKCAMR is briefly discussed in turn below. Most NKCAMRs appear to belong to one of two classes of proteins: the immunoglobulin (Ig)-like receptor superfamily (IgSF) or the C-type lectin-like receptor (CTLR) super family (see, e.g., Radaev and Sun, Annu. Rev. Biomol. Struct. 2003 32:93-114). However, other forms of NKCAMRs are known.

Antibodies against NKCAMR, such as killer immunoglobulin-like receptors (KIR), have been previously described and there also has been at least some suggestion of combining anti-NK receptor antibodies, such as anti-KIR antibodies, with other anti-cancer agents in the prior art. For example, WO2004056392 describes anti-NKp30 and/or anti-NKp46 antibodies used in admixture with interleukin-2 (IL-2). WO2005009465 describes the combination of a therapeutic antibody (e.g., Rituxan) in combination with a compound that blocks an inhibitory receptor or stimulates an activating receptor of an NK cell (e.g., an anti-KIR mAb, such as the mAb DF200, or an anti-NKp30 mAb) in order to enhance the efficiency of the treatment with therapeutic antibodies in human subjects (see also US 20050037002). WO2008/084106 describes anti-KIR formulations, dosages and dose regimens. WO2005079766 also describes combinations of antibodies (e.g., anti-tissue factor antibodies) including anti-KIR antibodies for use in cancer therapies. WO2005003168 and WO2005003172 describe combinations of a number of anti-KIR antibodies with a variety of agents, including IL-2 and IL-21. WO2005037306 similarly describes combinations of IL-21, IL-21 derivatives, and IL-21 analogues in combination with anti-KIR antibodies.

While NK cells have received a great deal of attention in the scientific literature for their potential contribution to anti-tumor responses mediated by antibodies that bind tumor antigens, few studies have been directed to examining the in vivo efficacy or potentiating NK cell cytotoxicity directly by modulating NK cell receptors. Treatments with NK cell modulating compounds have to date generally been envisaged as potentially restoring the ability of NK cells to kill target cells. Such treatments have not been used in patients without advanced disease, possibly in view of evidence that NK cell immunosurveillance is impaired with significant disease (e.g., tumor burden). For example, in myeloma, aggressive multiple myeloma (MM) parallels with a quantitative decline and functional exhaustion of NK cells. NK cell count also declines and NK cells become hyporesponsive to stimulation in patients with advanced MM.

Consequently, there is a need in the art for methods of using NK cell modulation to provide improved benefit to patients. Compounds that modulate NK cell activity, e.g., anti-+NKCIR antibodies and fragments thereof, may be particularly useful in the treatment of cancer.

SUMMARY OF THE INVENTION

The present invention provides methods for treating an individual having or previously having had a hematological malignancy or pre-malignancy. The methods comprise administering to the individual a therapeutically active amount of a compound that inhibits a NK cell inhibitory receptor (NKCIR). The compound is preferably administered to the individual at a time when the individual has minimal or non-detectable disease. Additionally, the invention contemplates use of a compound that inhibits a NKCIR (Natural Killer Cell Inhibitory Receptor), for preparing a pharmaceutical composition for treating an individual having or previously having had a hematological pre-malignancy or hematological malignancy, for administration to an individual at a time when the individual has minimal or non-detectable disease, said composition comprising a therapeutically active amount of a compound that inhibits a NKCIR (Natural Killer Cell Inhibitory Receptor).

In one embodiment of the invention, the individual has a hematological pre-malignancy. In a particular embodiment, the individual has SMM (smoldering myeloma), MGUS (monoclonal gammopathy of undetermined significance), or MDS (myelodysplastic syndrome).

In another embodiment of the invention, the individual has or previously has had a hematological malignancy or a genetic mutation that correlates to an increased risk of the onset of a hematological malignancy. In a particular embodiment, the individual has or previously has had leukemia, lymphoma, myeloma, or a lymphoid malignancy. In a preferred embodiment, the individual has or previously has had AML (acute myeloid leukemia), MM (multiple myeloma), SMM (smoldering myeloma), CML (chronic myelogenous leukemia), or CLL (chronic lymphocytic leukemia).

In one embodiment, the individual has been treated with a first treatment for the hematological malignancy or hematological pre-malignancy prior to administering the compound. The first treatment may be selected from treatment with a chemotherapeutic agent, an immunomodulatory agent, radiotherapy, surgery, an anti-hormone agent, or an anti-angiogenic agent or a combination of any of the foregoing. Preferably, the individual experienced a partial response or a complete response to treatment with the first treatment. As a result of the first treatment, the individual may be in remission, have a non-detectable disease, is asymptomatic, and/or have low number of abnormal cells.

In one embodiment, the hematological malignancy is a leukemia, namely acute myeloid leukaemia (AML). Preferably, the individual is in remission, is asymptomatic, has a non-detectable disease, and/or has a low number of abnormal cells, optionally following treatment with the first treatment. In a particular embodiment, the individual has total body leukaemia burden below approximately $10^9$ cells and/or less than 5% blasts in the marrow and/or no signs or symptoms of leukemia.

In one embodiment, the hematological malignancy is a myeloma, namely multiple myeloma (MM). Preferably, the individual has experienced a partial or complete response, is in remission, is asymptomatic, has a non-detectable disease, and/or has a low number of abnormal cells, optionally following treatment with the first treatment. In a particular embodiment, the individual has experienced a greater than 25% reduction in the serum protein M level. Preferably, the individual has experienced a greater than 50% reduction in the serum protein M level.

In one embodiment, the hematological malignancy is smoldering multiple myeloma (SMM). Preferably, the individual has experienced a partial or complete response, is in remission, is asymptomatic, has a non-detectable disease, and/or has a low number of abnormal cells, optionally following treatment with the first treatment. In a particular aspect of the invention, the individual has 10% or more plasma cells in the bone marrow but does not meet the criteria for multiple myeloma (MM). In another aspect of the invention, the individual has serum M protein ≥3 g/dL. In yet another aspect of the invention, the individual has 10% or more plasma cells in the bone marrow with no evidence of end-organ damage (CRAB). In a further embodiment, the individual has serum M protein ≥3 g/dL and also has 10% or more plasma cells in the bone marrow, optionally further with no evidence of end-organ damage.

In one embodiment, the hematological malignancy is asymptomatic monoclonal gammopathy of unknown significance (MGUS). In such an embodiment, the individual preferably has less than 10% plasma cells in the bone marrow.

The invention also contemplates methods comprising:
(a) determining whether an individual having or having had a hematological malignancy has minimal or non-detectable disease; and
(b) if the individual has minimal or non-detectable disease, treating the individual with a therapeutically active amount of a compound that inhibits a NKCIR.

Moreover, the invention includes methods comprising:
(a) determining whether an individual has a smoldering multiple myeloma (SMM), an asymptomatic monoclonal gammopathy of unknown significance (MGUS) or a myelodysplastic syndrome (MDS);
(b) if the individual has SMM, MGUS or MDS, treating the individual with a therapeutically active amount of a compound that inhibits a NKCIR.

Furthermore, the invention includes methods, comprising:
(a) treating an individual having a hematological malignancy with a first treatment (e.g., one or more induction therapies and optionally one or more consolidation therapies), optionally wherein the first treatment is a chemotherapeutic agent or an immunomodulatory agent, e.g., an Imid, such that the individual has minimal or non-detectable disease (e.g., disease is in remission and/or the individual experiences a response to the first treatment);
(b) treating the individual having minimal or non-detectable disease with a therapeutically active amount of a compound that inhibits a NKCIR. Optionally, step (a) further includes determining whether an individual having or having had a hematological malignancy has minimal or non-detectable disease.

Additionally, the invention contemplates the use of a compound in preparing a composition containing a moiety that detects whether an individual has or previously had had a hematological malignancy has minimal or non-detectable disease and if the individual has minimal or non-detectable disease, treating the individual with a therapeutically active amount of a compound that inhibits a NKCIR.

The invention also contemplates the use of a compound in preparing a composition containing a moiety that detects whether an individual has a smoldering multiple myeloma (SMM), an asymptomatic monoclonal gammopathy of unknown significance (MGUS) or a myelodysplastic syndrome (MDS), and if the individual SMM, MGUS, or MDS, treating the individual with a therapeutically active amount of a compound that inhibits a NKCIR.

Moreover, the invention includes the use of a compound in preparing a composition for treating an individual having a hematological malignancy, treating the individual with a first treatment, such that the individual has minimal or non-detectable disease, and treating the individual having minimal or on-detectable disease with a therapeutically active amount of a compound that inhibits a NKCIR.

In one embodiment, determining whether an individual having or having had a hematological malignancy has minimal or non-detectable disease, is in remission, has a partial or complete response, and/or has a particular pathology (e.g., SMM, MGUS, AML, CML, MDS, MM, etc.) is made according to standard medical guidelines.

In one embodiment, determining whether an individual having or having had a hematological malignancy has minimal or non-detectable disease, is in remission or has a partial or complete response comprises identifying a population of abnormal cells or abnormal numbers of cells (e.g., percentage of plasma cells in bone marrow). Optionally, said identification is by flow cytometry. Optionally, the method further comprises sorting or isolating the population of abnormal cells.

In one embodiment, determining whether an individual having or having had a hematological malignancy has minimal or non-detectable disease, is in remission and/or has a complete response comprises detecting cytogenetic aberrations (e.g., assessing karyotype).

In one embodiment, detection of minimal disease comprises sorting the population of abnormal cells; and contacting nucleic acid isolated from the sorted cells with one or more nucleic acids that target a genetic rearrangement that correlates to increased likelihood of the onset of a hematological malignancy, wherein the contacting determines the presence of cytogenetic aberrations; thereby detecting the presence of minimal disease. In one embodiment, the genetic marker is a mutation in FLT3 or NpM1 that correlates to poor prognosis for survival in individuals having AML. In another embodiment, the genetic marker is a rearrangement in the Immunoglobulin (Ig) and/or T cell receptor gene.

In one embodiment, determining whether an individual having or having had a hematological malignancy has minimal or non-detectable disease, is in remission and/or has a partial or complete response (e.g., in MM) comprises assessing the levels of serum monoclonal protein (M protein) in the individual.

In one embodiment, determining whether an individual has SMM or MGUS comprises assessing the levels of serum monoclonal protein (M protein) in the individual; optionally wherein the patient is determined to have SMM if the levels of M protein are at least 3 g/dL. In one embodiment, determining whether an individual has SMM or MGUS comprises assessing bone marrow plasma cells in the individual; optionally wherein the patient is determined to have SMM if the individual has at least 10% bone marrow plasma cells.

As discussed above, a patient has a poor disease prognosis, e.g., is at a higher risk of progression, based on one or more predictive factors. In one embodiment, the patient has SMM and is within Group 1, according to the classification in Table 2. In one embodiment, the patient has a poor prognosis based on gene mutations, e.g., the patient has AML and has a mutation in FLT3 or NpM1 associated with a poor prognosis.

In one embodiment, the compound that inhibits a NKCIR is used as a single agent. In another embodiment, the compound that inhibits a NKCIR is administered in combination with at least one other therapeutic agent.

The compound that inhibits a NKCIR may modulate NK cell cytotoxicity as a result of inhibiting said NKCIR. Preferably, the compound that inhibits a NKCIR is an anti-NKCIR antibody or antibody fragment having the ability to block or neutralize NKCIR-mediated NK inhibition and thereby potentiate NK cell activity against otherwise blocked target cells. In one embodiment, the antibody or antibody fragment is an antibody against a killer immunoglobulin-like receptor (KIR) or a fragment thereof. In another embodiment, the antibody or antibody fragment is a chimeric, human, or humanized antibody or antibody fragment. In yet another embodiment, the antibody or antibody fragment comprises an IgG1, IgG2, IgG3, IgG4, IgD, IgA, IgE, or IgM. Preferably, the antibody or antibody fragment comprises an IgG1 or IgG4. In one embodiment, the antibody or antibody fragment comprises a Fc domain that comprises at least one mutation that affects one or more of effector function, half-life, proteolysis, FcR binding, or glycosylation.

In a particular embodiment, the antibody or antibody fragment is an anti-KIR antibody or antibody fragment that binds KIR2DL1 and KIR2DL2/3. Preferably, the anti-KIR antibody or antibody fragment competes with 1-7F9. More preferably, the anti-KIR antibody or antibody fragment is 1-7F9 or a fragment thereof. It is also contemplated that the anti-KIR antibody fragment is a fragment of 1-7F9 that has the same binding properties as 1-7F9. In one aspect, the anti-KIR antibody or antibody fragment comprises VL and VH domains which are at least 90% identical to those of 1-7F9. In another aspect, the anti-KIR antibody or antibody fragment comprises the VL and VH domains of 1-7F9. In yet another aspect, the VL of the anti-KIR antibody or antibody fragment comprises the VL CDRs of 1-7F9. In a further aspect, the VH of the anti-KIR antibody or antibody fragment comprises the VH CDRs of 1-7F9.

In one embodiment, the anti-KIR antibody or antibody fragment comprises a polypeptide whose amino acid sequence has at least 80% sequence identity to 1-7F9, at least 90% sequence identity to 1-7F9, at least 95% sequence identity to 1-7F9, or at least 98% sequence identity to 1-7F9. In another embodiment, the anti-KIR antibody or antibody fragment specifically binds to the same linear or conformational epitope on an intact KIR2DL1 or KIR2DL2/3 as does 1-7F9, and/or competes with 1-7F9 for binding to the same linear or conformation epitope on an intact KIR2DL1 or KIR2DL2/3.

In another embodiment, the antibody of antibody fragment is an antibody against an NKCIR selected from the group consisting of CD94, NKG2 (e.g., NKG2A and NKG2E) and LIR (e.g., LILRB1 to B5), or a fragment thereof.

In one embodiment of the invention, the anti-NKCIR antibody is administered as a pharmaceutically acceptable composition comprising a therapeutically effective amount of the anti-NKCIR antibody. In one aspect, the NKCIR antibody is administered in an amount resulting in substantially complete saturation of the NKCIR on NK cells for a period of at least about 1 week, at least about 2 weeks, or at least about one month.

In one aspect, antibody is dosed in amount and at a frequency that results in substantially complete saturation of the NKCIR on NK cells for a period of at least about 1 week, at least about 2 weeks, or at least about 1 month without a significant "de-saturation" during the treatment period. In one embodiment, a therapeutically active amount of one or more NKCIR antibodies is an amount of such antibody that results in substantially complete NKCIR saturation on NK cells for a period of at least about 1 week, about 2 weeks, or about 1 month, following administration of the antibody, where the antibody is administered several times at a dosing frequency of once about every 2 weeks, once about every month, or once about every 2 months or longer and the subsequent doses are separated by about 2 weeks or about 1 month.

In one aspect, antibody is dosed in amount and at a frequency that results in substantially complete saturation of the NKCIR on NK cells for a period of at least about 1 week, at least about 2 weeks, or at least about 1 month and that permits a significant "de-saturation" during the treatment period. In one embodiment, a therapeutically active amount of one or more NKCIR antibodies is an amount of such antibody that results in substantially complete NKCIR saturation on NK cells for a period of at least about 1 week, about 2 weeks, or about one month, following administration of the antibody, where the antibody is administered several times at a dosing frequency of one about every 2 weeks, about once every month, or about once every two months and subsequent doses are separated by about 2 weeks or about 1 month.

In another embodiment, the anti-NKCIR antibody or antibody fragment is administered in a dosage range of about 0.1 mg/kg to about 3.0 mg/kg, about 0.3 mg/kg to about 3.0 mg/kg, about 0.1 mg/kg to about 1.0 mg/kg, or about 1.0 mg/kg to about 3.0 mg/kg. Preferably, the anti-NKCIR antibody or antibody fragment is administered about once every 2 months.

In another aspect, any one of the various above-described methods may further optionally be modified by application of a chemotherapy treatment with one or more additional anti-cancer agents, e.g., chemotherapy agents.

In another embodiment, pharmaceutical compositions for human therapy are provided that contain an anti-NKCIR antibody or antibody fragment according to the invention and a pharmaceutically acceptable carrier or excipient, which d upon administration to an average human subject (about 45-90 kg in weight) result in a dosage range of about 0.1 mg/kg to about 3.0 mg/kg, about 0.3 mg/kg to about 3.0 mg/kg, about 0.1 mg/kg to about 1.0 mg/kg, or about 1.0 mg/kg to about 3.0 mg/kg. In specific embodiments composition upon administration to an average human subject results in a dosage range of about 0.1-0.3 mg/kg, and more specifically 0.2 mg/kg or about 0.3 mg/kg.

The invention also contemplates methods for treating an individual having a disease and/or for potentiating NK cell activity in an individual in need thereof. The method comprising administering to the individual an anti-NKCIR antibody or antibody fragment in an amount that provides for a dosage of about 0.1 mg/kg to about 0.3 mg/kg in a human patient, and a pharmaceutically acceptable carrier, wherein the anti-NKCIR antibody or antibody fragment is administered no more than once per month. Additionally, the invention contemplates the use of an anti-NKCIR antibody or antibody fragment in an amount that provides for a dosage of about 0.1 mg/kg to about 0.3 mg/kg in a human patient and a pharmaceutically acceptable carrier for the preparation of a pharmaceutical composition for human therapy. In one embodiment, the anti-NKCIR antibody or antibody fragment is administered no more than once every two months. In another embodiment, the anti-NKCIR antibody or antibody fragment is administered between once per month and once every two months. In yet another embodiment, the anti-NKCIR antibody or antibody is provided in a dosage of about 0.1 mg/kg to about 0.2 mg/kg in a human patient.

These aspects are more fully described in, and additional aspects, features, and advantages of the invention will be apparent from, the description of the invention provided herein.

BRIEF DESCRIPTION OF THE FIGURES

FIG. 2 (FIG. 12 of WO2006/003179) provides a comparative alignment of the amino acid sequences of the light chain variable regions, and light chain CDRs of antibodies DF200 and Pan2D (NKVSF1). (A) Alignment of anti-KIR variable light (VL) regions of DF200 (SEQ ID NO:1) and Pan-2D (SEQ ID NO:2). Numbers above amino acid sequences indicate position respective to initiation of translation Met (+1) in the immature (non-secreted) immunoglobulin. (B) Alignment of CDR-L1 sequences. Residue before: Normally Cys. Residues after: Trp. Typically Trp-Tyr-Leu. Length: 10-17 aa. (C) Alignment of CDR-L2 sequences. Residues before: Generally Ile-Tyr. Length: 7 aa. Start: approximately 16 aa after the end of CDR-L1. Start: approximately 24 aa from the beginning of secreted protein. (D) Alignment of CDR-L3 sequences. Residues before: Cys. Residues after: Phe-Gly-XXX-Gly. Length: 7-11 aa. Start: approximately 33 aa after the end of CDR-L2.

FIG. 3 (FIG. 13 of WO2006/003179) provides the heavy chain variable region, and the heavy-chain CDRs of antibody DF200. (A) DF-200 VH region, immature protein. The secreted, mature VH starts at position 20: residue Q. The VH region ends with residue S and thereafter the constant region (not shown) continues. (B) CDR-H1. Residues before: Cys-Xaa-Xaa-Xaa (where "Xaa" signifies any amino acid). Residues after: Trp. Generally Trp-Val or Trp-Ile. Length: 10-14 aa. Start: Approximately 22-26 aa from the beginning of the secreted protein. (C) CDR-H2. Residues before: Leu-Glu Trp-Ile-Gly but other variations possible. Residues after: Lys or Arg/Leu or Ile or Val or Phe or Thr or Ala/Thr or Ser or Ile or Ala. Length: 16-20 aa. Start: Approximately 15 aa after the end of CDR-H1. (D) CDR-H3. Residues before: Cys-Xaa-Xaa (Typically Cys-Ala-Arg). Residues after: Trp-Gly-Xaa-Gly. Length: 3-25 aa. Start: Approximately 33 after the end of CDR-H2.

FIG. 4 (FIG. 14 of WO2006/003179) depicts the nucleotide and amino acid sequences of the VH and VL sequence of human antibody 1-7F9. (A) Translation of HuKIR 1-7F9 mature variable light chain. (B) Nucleotide sequence encoding HuKIR 1-7F9 mature variable light chain. (C) Translation of HuKIR 1-7F9 mature variable heavy chain. (D) Nucleotide sequence encoding HuKIR 1-7F9 mature heavy chain.

FIG. 6 (FIG. 20 of WO2006/003179) shows the binding epitope of 1-7F9 on KIR2DL1, as indicated in the KIR2DL1 sequence. Amino acids within 4.0 Å distance from 1-7F9 are highlighted in grey and black background. Amino acids highlighted by a black background are involved in hydrogen-bonding to 1-7F9. The sequence ID No's listed in FIGS. 2-6 correspond to SEQ ID NO's in the Sequence Listing filed in WO2006/003179 that is contained in the pages that immediately precede the claims of this application.

DESCRIPTION OF THE INVENTION

Figure 1:
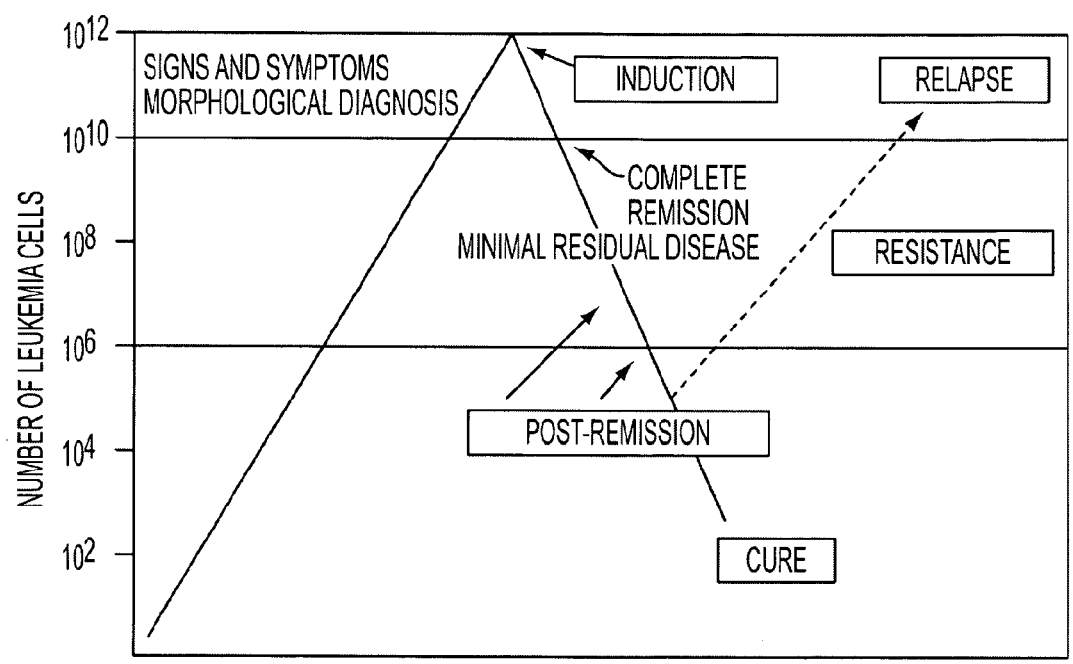
FIG. 1 shows the therapeutic strategy for most patients with AML which is divided into two general phases: induction therapy and post-remission therapy.
Figure 5:
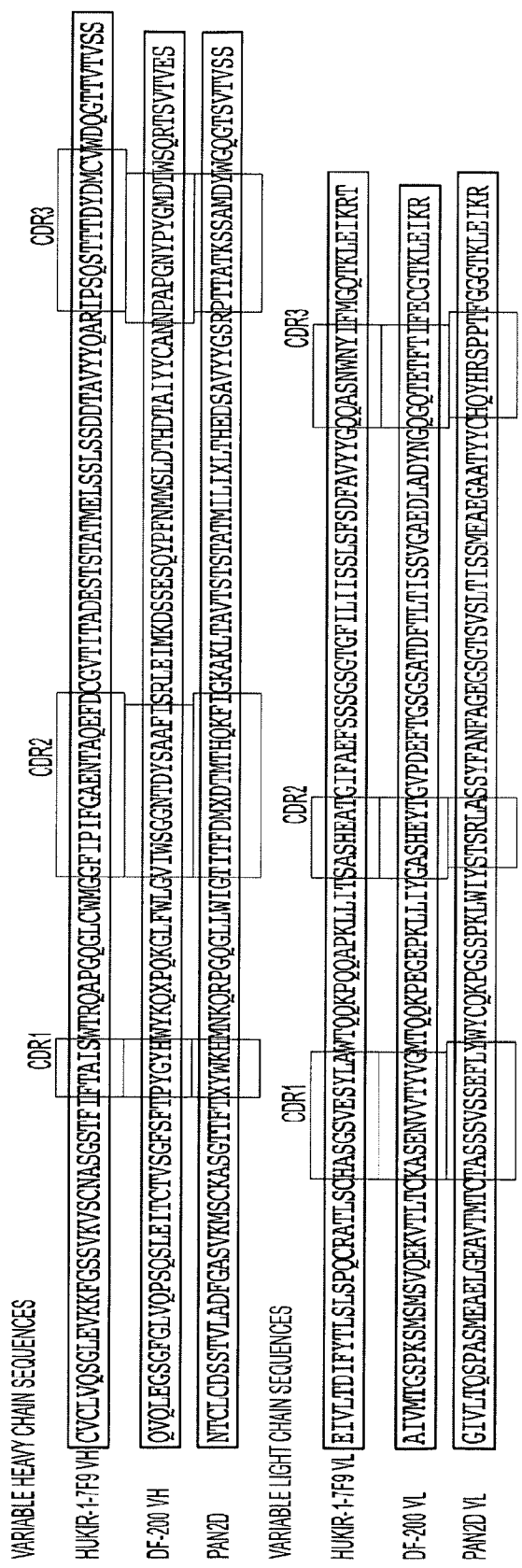
FIG. 5 (FIG. 15 of WO2006/003179) shows the amino acid sequences of the VH and VL sequences of monoclonal antibodies 1-7F9, DF200 (VH sequence: SEQ ID NO:19; VL sequence: SEQ ID NO:21), and Pan2D (NKVSF1; VH sequence: SEQ ID NO:20; VL sequence: SEQ ID NO:22). The CDRs are boxed.

This invention provides methods for treating an individual having or previously having had a hematological malignancy or pre-malignancy. The methods comprise administering to the individual a therapeutically active amount of a compound that inhibits a NK cell inhibitory receptor (NKCIR). The compound is administered to the individual at a time when the individual has minimal or non-detectable disease.

Human clinical trials described herein showed that treatment with a compound that blocks an NK cell inhibitor receptor involved in NK cell cytotoxicity, e.g., anti-NKCIR antibodies, greatly prolonged disease-free survival in patients who had suffered from hematological malignancy but were in remission and/or had minimal or undetectable disease when treated with the compound.

Antibodies

Unless otherwise stated or clearly contradicted by context, the term antibody in the context of this invention refers to an immunoglobulin (Ig) molecule, a fragment of an Ig molecule, or a derivative of either thereof that has the ability to (a) specifically bind to at least one target antigen under typical physiological conditions for significant periods of time and/or (b) modulate a physiological response associated with its target NKCIR, such as modulating KIR-modulated NK cell activity. A significant period of time in this respect means any period suitable for detection of the antibody-antigen complex in a standard immunological assay, such as an enzyme-linked immunosorbent assay (ELISA). Typically, a significant period of time is a period of at least about 30 minutes, at least about 45 minutes, at least about one hour, at least about two hours, at least about four hours, at least about 8 hours, at least about 12 hours, about 24 hours or more, about 48 hours or more, etc.

Immunoglobulins are a class of structurally related proteins comprising heavy chains (e.g., $\alpha$, $\Delta$, $\epsilon$, $\gamma$, and $\mu$ chains) and light chains (e.g., $\kappa$ and $\lambda$ chains). In humans, immunoglobulins may be divided into five major classes (IgA, IgD, IgE, IgG, and IgM) according to which heavy chains are contained in the Ig molecule.

The structure of immunoglobulins is well characterized. See, e.g., Fundamental Immunology (Paul, W., ed., 2nd ed. Raven Press, N.Y. (1989)). IgG molecules, the most common type of immunoglobulin, comprise two pairs of polypeptide chains, one pair of light (L), low molecular weight chains and one pair of heavy (H) chains, all four interconnected by disulfide bonds. Briefly, each heavy chain typically is comprised of a heavy chain variable region (abbreviated herein as HCVR or VH) and a heavy chain constant region. The heavy chain constant region typically is comprised of three domains, CH1, CH2, and CH3. Each light chain typically is comprised of a light chain variable region (abbreviated herein as LCVR or VL) and a light chain constant region. The light chain constant region typically is comprised of one domain, CL. The VH and VL regions can be further subdivided into regions of hypervariability (or hypervariable regions, which can be hypervariable in sequence and/or form of structurally defined loops), also termed complementarity determining regions (CDRs), interspersed with regions that are more conserved, termed framework regions (FR). In full length, naturally produced antibodies, each VH and VL typically is composed of three CDRs and four FRs, arranged from amino-terminus to carboxy-terminus in the following order: FR1, CDR1, FR2, CDR2, FR3, CDR3, FR4 (which also may be referred to as FR L1, CDR L1, etc. or loop L1, L2, L3 in the light chain variable domain and loop H1, H2, and H3 in the heavy chain domain in the case of hypervariable loop regions (see, e.g., Chothia and Lesk J. Mol. Biol. 196:901-917 (1987)). Typically, the numbering of amino acid residues in this region is performed by the method described in Kabat et al., Sequences of Proteins of Immunological Interest, 5th Ed. Public Health Service, National Institutes of Health, Bethesda, Md. (1991) (phrases such as "variable domain residue numbering as in Kabat" and "according to Kabat" herein refer to this numbering system for heavy chain variable domains or light chain variable domains). Using this numbering system, the actual linear amino acid sequence of a peptide may contain fewer or additional amino acids corresponding to a shortening of, or insertion into, a FR or CDR of the variable domain. For example, a heavy chain variable domain may include a single amino acid insert (residue 52a according to Kabat) after residue 52 of CDR H2 and inserted residues (e.g., residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence.

As indicated above, an anti-NKCIR antibody can be in the form of (or comprise) an antibody "fragment" that retains the ability to specifically bind to a NKCIR. Such antibody fragments can be characterized by possessing any one or combination of the aforementioned features associated with full length antibodies, discussed elsewhere herein, to the extent appropriate (e.g., many antibody fragments lack an Fc domain and, accordingly, do not induce or promote antibody-associated complement functions). The antigen-binding function of antibodies can be performed by any number of suitable fragments thereof. Examples of antibody fragments include (i) a Fab fragment, a monovalent fragment consisting essentially of the VL, VH, CL and CH I domains; (ii) F(ab)2 and F(ab')2 fragments, bivalent fragments comprising two Fab fragments linked by a disulfide bridge at the hinge region; (iii) a Fd fragment consisting essentially of the VH and CH1 domains; (iv) a Fv fragment consisting essentially of the VL and VH domains of a single arm of an antibody, (v) a dAb fragment (Ward et al., (1989) Nature 341:544-546), which consists essentially of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain antibodies or single chain Fv (scFv); see e.g., Bird et al. (1988) Science 242:423-426: and Huston et al. (1988) Proc. Natl. Acad. Sci. USA 85:5879-5883). Such single chain antibodies also are encompassed within terms such as antibody fragment and antibody-like peptide/molecule, unless otherwise noted or clearly indicated by context. Other forms of single chain antibodies, such as diabodies also are intended be encompassed by these terms. Diabodies are bivalent, bispecific antibodies in which VH and VL domains are expressed on a single polypeptide chain, but using a linker that typically is too short to allow for pairing between the two domains on the same chain, thereby forcing the domains to pair with complementary domains of another chain and creating two antigen binding sites (see e.g., Holliger, P., et al. (1993) Proc. Natl. Acad. Sci. USA 90:6444-6448; Poljak, R. J., et al. (1994) Structure 2:1121-1123; and Cao et al. (1998), Bioconjugate Chem. 9, 635-644). Although having similar binding properties as full-length antibodies, such antibody fragments collectively and each independently are unique features of the invention, exhibiting different biological and/or physiochemical properties and utilities than antibodies. These and other useful antibody fragments and antibody-like molecules provided by this invention are discussed further herein. It should be generally understood that any suitable antibody fragment can be used as a surrogate for an antibody in inventive compositions and methods described herein, and visa versa, unless otherwise stated or clearly contradicted by context.

In a general sense, the term antibody includes polyclonal antibodies and monoclonal antibodies (mAbs). The term "monoclonal antibody" refers to a composition comprising a homogeneous antibody population having a uniform structure and specificity. Polyclonal antibodies typically are derived from the serum of an animal that has been immunogenically challenged, but they can also be derived by recombinant technology. Anti-KIR antibodies can be considered monoclonal antibodies, regardless of the manner in which they are produced.

An antibody as generated can possess any isotype and the antibody can be isotype switched thereafter using conventional techniques that are well known in the art. Such techniques include the use of direct recombinant techniques (see, e.g., U.S. Pat. No. 4,816,397), cell-cell fusion techniques (see e.g., U.S. Pat. No. 5,916,771), and other suitable techniques known in the art. Thus, for example, the effector function of multispecific multivalent antibodies provided by the invention may be "changed" with respect to the isotype of one or both parent antibodies by isotype switching to, e.g., an IgG1, IgG2, IgG3, IgG4, IgD, IgA, IgE, or IgM antibody for various therapeutic uses.

NK Cell Activity-Modulating Receptors (NKCAMRs)

NK cell activity is regulated by NK cell activity-modulating receptors ("NKCAMRs" or simply "AMRs"), which may be specific for various ligands such as MHC-I molecules, MHC-I homologs, or other biological molecules expressed on target cells. NK cells in an individual typically present a number of activating and inhibitory receptors. The activity of NK cells is regulated by a balance of signals transduced through these activating and inhibitory receptors. Each type of NKCAMR is briefly discussed in turn below.

When somatic cells are either under stress, such in cancer progression or infection, various molecules, such as MICA and MICB, are typically displayed on the surface of the stressed cells and normally displayed MHC-I molecules are "lost" from the cell surface (reduced in number and/or glycosylated such that they are not "seen" as "foreign" by the immune system). NKCAMRs are sensitive to these and other changes in potential NK target cells associated with cellular stress, disease, and disorder.

Most NKCAMRs appear to belong to one of two classes of proteins: the immunoglobulin (Ig)-like receptor superfamily (IgSF) or the C-type lectin-like receptor (CUR) super family (see, e.g., Radaev and Sun, Annu. Rev. Biomol. Struct. 2003 32:93-114). However, other forms of NKCAMRs are known. The structures of a number of NKCAMRs have been elucidated (Id.). To better illustrate the invention, types of well understood NKCAMRs, with reference to particular examples thereof, are described here. However, several additional NKCAMRs are known besides those receptors explicitly described here (see, e.g., Farag et al., Expert Opin. Biol. Ther. 3(2):237-250) and the inventive compositions and methods described herein typically will also be applicable to these and other NKCAMRs.

NK Cell Activating Receptors (NKCARs)

Many NK cell activating receptors (NKCARs) belong to the Ig superfamily (IgSF) (such receptors also may be referred to as Ig-like receptors or "ILRs" herein). Activating ILR NK receptors (AILRs) include, e.g., CD2, CD16, CD69, DNAX accessory molecule-1 (DNAM-1), 2B4, NK1.1; killer immunoglobulin (Ig)-like activating receptors (KARs); ILTs/LIRs; and natural cytotoxicity receptors (NCRs) such as NKp44, NKp46, and NKp30. Several other NKCARs belong to the CLTR superfamily (e.g., NKRP-1, CD69; CD94/NKG2C and CD94/NKG2E heterodimers, NKG2D homodimer, and in mice, activating isoforms of Ly49 (such as Ly49A-D)). Still other NKCARs (e.g., LFA-1 and VLA-4) belong to the integrin protein superfamily and other activating receptors may have even other distinguishable structures. Many NKCARs possess extracellular domains that bind to MHC-I molecules, and cytoplasmic domains that are relatively short and lack the inhibitory (ITIM) signaling motifs characteristic of inhibitory NK receptors. The transmembrane domains of these receptors typically include a charged amino acid residue that facilitates their association with signal transduction-associated molecules such as CD3zeta, FcεRIγ, DAP12, and DAP10 (2B4, for example, appears to be an exception to this general rule), which contain short amino acid sequences termed an Immunoreceptor tyrosine-based activating motif (ITAMs) that propagate NK cell-activating signals. Receptor 2B4 contains 4 so-called Immunoreceptor Tyrosine-based Switch Motif (ITSM) in its cytoplasmic tail; ITSM motifs can also be found in NKCARs CS1/CRACC and NTB-A. The cytoplasmic domains of 2B4 and SLAM contain two or more unique tyrosine-based motifs that resemble motifs presents in activating and inhibitory receptors and can recruit the SH2-domain containing proteins SHP-2 and SAP (SLAM-associated protein).

Stress-induced molecules, such as MIC-A, MIC-B, and ULBPs in humans, and Rae-1 and H-60 in mice, can serve as ligands for NKCARs, such as the NKG2D homodimer. Cellular carbohydrates, pathogenic antigens, and antibodies can also be NKCAR ligands. For example, NKR-P1 may bind to carbohydrate ligands and trigger NK cell activation, particularly against tumor cells which exhibit aberrant glycosylation patterns. Viral hemagglutinins may serve as ligands for natural cytotoxic receptors (NCRs), such as ILR NKCARs NKp30, NKp44, NKp46, and NKp80.

NKCARs can either directly transduce activating signals or can act in connection with adaptor molecules or other receptors (either in the context of a coordinated response between receptors that are sometimes singularly effective or in the context of coreceptor-receptor pairings). For example, NKCAR NCRs typically lack ITAMs and, accordingly, bind to adaptor molecules through a charged residue in their transmembrane domains (e.g., NKp30 associates with the CD3 zeta chain; NKp44 associates with DAP12 and/or KARAP; NKp46 is coupled to the CD3 zeta chain and FcRIγ chain), which are, in turn, able to recruit protein tyrosine kinases (PTKs) in order to propagate NK cell-activating signals. CD16, which is a NKCAR important to NK cell-mediated ADCC and cytokine production, associates with homodimers or heterodimers formed of CD3 zeta and/or gamma chains. NKG2D appears to play a complementary and/or synergistic role with NCRs and NKCARs in NK cell activation. Activation of NK cells against particular targets may require coordinated activation of multiple NKCARs or NCRs, or only action of a single receptor. Other triggering surface molecules including 2B4 and NKp80 appear to function as coreceptors for NK cell activation.

Activating isoforms of human KIRs (e.g., KIR2DS and KIR3DS) and murine Ly-49 proteins (e.g., Ly-49D and Ly-49H) are expressed by some NK cells. These molecules differ from their inhibitory counterparts (discussed below) by lacking inhibitory motifs (ITIMs) in their relatively shorter cytoplasmic domains and possessing a charged transmembrane region that associates with signal-transducing polypeptides, such as disulfide-linked dimers of DAP12.

NKCIRs NK Cell Inhibitory Receptors

ILR (IgSF) NK cell inhibitory receptors (NKCIRs) (I) include a number of different human KIRs, specific for HLA-A, -B, or -C allotypes. KIRs may recognize multiple alleles within a particular allotype, e.g., KIR2DL1 recognizes HLA-Cw2, 4, and 6 allotypes. CTLR superfamily inhibitory receptors include members of the CD94/NKG2 protein family, which comprise receptors formed by lectin-like CD94 with various members of the NKG2 family, such as NKG2A, and recognize the nonclassical class I molecules HLA-E and Qa-1 in humans and mice, respectively, and the murine Ly49 molecules that recognize the classical class I MHC molecules in mice. In even further contrast, NKRP1A, Nkrp1f and Nkrp1d are inhibitory receptors whose ligands are not MHC-related but are CTLR family members expressed on various cell types, such as dendritic cells, macrophages, and lymphocytes.

MHC class I-specific NKCIRs include CTLR Ly-49 receptors (in mice); the IgSF receptors Leukocyte Immunoglobulin-like Receptors (LIRs) (in humans), KIRs (e.g., p58 and p70 Killer-cell Immunoglobulin-like Receptors, in humans), and CTLR CD94/NKG2 receptors (in mice and humans). All MHC-1-specific NKCIRs appear to use a common inhibitory mechanism apparently involving phosphorylation of ITIMs in their cytoplasmic domains in the course of MHC-I binding and recruitment of tyrosine phosphatases (e.g., SHP-1 and SHP-2) to the phosphorylated ITIMs, resulting in the inhibition of proximal protein tyrosine kinases (PTKs) involved in NK activation through NKCARs.

Inhibitory CD94/NKG2 heterodimers formed from CTLR glycoproteins, comprise an ITIM-bearing NKG2 molecule (e.g., NKG2A) and bind to non-classical MHC-I molecules (e.g., HLA-E in humans and Qa-1 in mice).

Leukocyte Immunoglobulin-like Receptors include several members, containing two or four Ig-domains and structurally related to KIR polypeptides. See, e.g., Fanger et al. 1999 J. Leukocyte Biol. 66:231-236. LIR include subfamilies A and B and include, e.g., LIR-1 to LIR-8 (several of which are also referred to ILT polypeptides, including ILT-1, ILT-2, ILT-3, ILT-4, ILT-5, and ILT-6. The polypeptides LIR-1, LIR-2, LIR-3, LIR-5, and LIR-8 all contain two or more ITIM inhibitory signaling domains.

Inhibitory Ly-49 receptors are murine type H membrane disulfide-linked homodimer CTLR glycoproteins, which bind to various MHC-I molecules and deliver typically dominant inhibitory (negative) signals to NK cells. Ly-49A, for example, binds to alpha1/alpha2 domains of MHC-I molecule H-2Dd, whereas Ly-49C binds H-2 Kb. Human NK cells appear to lack homologs of the murine Ly-49 receptors. Instead, human NK cells express KIRs, which are not found in mouse NK cells. Although human KIRs and mouse Ly-49 receptors lack structural homology, they are functionally orthologous: Both types of receptors bind to HLA class I on target cells, resulting in inhibition of NK-mediated cytotoxicity.

Killer-Cell Immunoglobulin-Like Receptors KIR

An important type of NKCIRs is the KIRs. Generally, KIRs are cell surface glycoproteins, comprising one to three extracellular immunoglobulin-like domains, which are expressed by some T cells as well as most human NK cells. A number of KIRs are well characterized (see, e.g., Carrington and Norman, The KIR Gene Cluster, May 28, 2003, available through the National Center for Biotechnology Information (NCBI) web site at http://www.ncbi.nlm.nih.gov/books/bookres.fcgi/mono_003/ch1d1.pdf). Human KIRs include KIR2DL and KIR3DL. KIRs also may be referred to by various other names such as CD158e1, CD158k, CD158z, p58 KIR CD158e1 (p70), CD244, etc. (see, e.g., US Patent Application 20040038894, Radaev et al., Annu. Rev. Biophys. Biomol. Struct., 32:93-114 (2003), Cerweknka et al., Nat. Rev. Immunol. 1:41-49 (2001); Farag et al., Expert Opin. Biol. Ther., 3(2):237-250 (2003); Biassoni et al., J. Cell. Mol. Med., 7(4):376-387 (2003); and Warren et al., British J. Haematology, 121:793-804 (2003), each of which being hereby incorporated into this application in their entirety). The structure of a number of KIRs has been elucidated and reveals remarkable structural similarity between these proteins. See, e.g., Radaev et al., supra.

KIRs can be classified structurally as well as functionally. For example, most KIRs have either two Ig domains (58 kDa KIR2D KIRs), whereas others have three Ig domains (70 kDa KIR3D KIRs), which may sometimes be respectively referred to as p58 and p70 molecules. KIRs vary also in cytoplasmic tail length. Typically, KIRs with a relatively long cytoplasmic tail (L) deliver an inhibitory signal, whereas KIR with a short cytoplasmic tail (S) can activate NK or T cell responses. Nomenclature for KIRs accordingly can be based upon the number of extracellular domains (KIR2D or KIR3D) and whether the cytoplasmic tail is long (KIR2DL or KIR3DL) or short (KIR2DS or KIR3DS). Additional nomenclature information for KIRs is provided in the following Detailed Description of the Invention. Some members of the "KIR family" are NKCARs, or more particularly "KARs" (e.g., KIR2DS2 and KIR2DS4); they typically comprise one or more charged transmembrane residues (e.g., Lys) that associate with an adapter molecule having an immunostimulatory motif (ITAM) (e.g., DAP12). The intracytoplasmic portion of inhibitory KIRs typically comprises one or more ITIMs that recruit phosphatases. Inhibitory KIRs bind to alpha1/alpha2 domains of HLA molecules. Inhibitory KIRs do not appear to typically require adaptor-molecule association for activity. Unless otherwise stated, terms such as "KIR", "KIRs", and the like refer to NKCIR members of the "KIR family" and terms such as "KAR", "KARs", and the like refer to NKCAR members of the "KIR family."

KIRs can bind MHC-I molecules (e.g., certain HLA class I allotypes), typically resulting in the transmission of a negative signal that counteracts, and may override stimulatory, activating signal(s) to the NK cell, thereby preventing the NK cell from killing the associated potential target cell (apparently via ITIM phosphorylation and tyrosine phosphatase (e.g., SH2-domain containing protein tyrosine phosphatases such as SHP-1 and SHP-2) recruitment, leading to PTK (e.g., Syk, TcR and/or ZAP70) dephosphorylation and/or LAT/PLC complex formation inhibition and associated disruption of ITAM cascade(s)). Because viruses often suppress class I MHC expression in cells they infect, such virus-infected cells become susceptible to killing by NK cells. Because cancer cells also often have reduced or no class I MHC expression, these cells, too, can become susceptible to killing by NK cells. Infected cells can also change the proteins bound in the MHC in terms of glycosylation. If this occurs, the MHC-I:protein complex the cell expresses will be altered. If NK-associated KIRs cannot bind to these "foreign" complexes, no inhibitory signal can be generated, and lysis will proceed.

All confirmed inhibitory KIRs appear to interact with different subsets of HLA/MHC antigens depending upon the KIR subtype. In humans, KIRs having two Ig domains (KIR2D) recognize HLA-C allotypes: KIR2DL2 (formerly designated p58.2) and the closely related gene product KIR2DL3 both recognize an epitope shared by group 1 HLA-C allotypes (Cw1, 3, 7, and 8), whereas KIR2DL1 (p58.1) recognizes an epitope shared by the reciprocal group 2 HLA-C allotypes (Cw2, 4, 5, and 6). The specificity of KIR2DL1 appears to be dictated by the presence of a Lys residue at position 80 of group 2 HLA-C alleles. KIR2DL2 and KIR2DL3 recognition appears to be dictated by the presence of an Asn residue at position 80. A substantial majority of HLA-C alleles have either an Asn or a Lys residue at position 80. One KIR with three Ig domains, KIR3DL1 (p70), recognizes an epitope shared by HLA-Bw4 alleles. Finally, a homodimer of molecules with three Ig domains, KIR3DL2 (p140), recognizes HLA-A3 and -A11.

Individual MHC-I-specific NK cell receptors of either type (activating or inhibiting) typically do not interact with all MHC class I molecules, but specifically bind to certain allotypes (proteins encoded by different variants of a single genetic locus). Also, an individual NK cell may express several different inhibitory and/or activating receptors which function independently of each other. For example, in humans the presence or absence of a given KIR is variable from one NK cell to another within a single individual. There also is relatively high level of polymorphism of KIRs in humans, with certain KIR molecules being present in some, but not all individuals. Although KIRs and other MHC-recognizing inhibitory receptors may be co-expressed by NK cells, in any given individual's NK repertoire there are typically cells that express a single KIR; accordingly, the corresponding NK cell activity in this latter type of NK cells is inhibited only by cells expressing a specific MHC-I allele group. In fact, recent estimates of the extent of KIR genotype diversity within the population suggest that <0.24% of unrelated individuals can expect to have identical genotypes. The most common Caucasian haplotype, the "A" haplotype (frequency of ~47-59%), contains only one activating KIR gene (KIR2DS4) and six inhibitory KIR loci (KIR3DL3, -2DL3, -2DL1, -2DL4, -3DL1, and -3DL2). The remaining "B" haplotypes are very diverse and contain 2-5 activating KIR loci (including KIR2DS1, -2DS2, -2DS3, and -2DS5).

It should be noted that KIRs are known by several aliases, as reflected here in Table 1, which includes information obtained from the Hugo Gene Nomenclature Committee web site (http://www.gene.ucl.ac.uk/nomenclature/gene-family/kir.html) and Andre et al., Nature Immunol. 2(8):661 (2001).

TABLE 1

KIR Nomenclature

| KIR | Full name | Aliases | Accession ID |
|---|---|---|---|
| KIR2DL1 | killer cell immunoglobulin-like receptor, two domains, long cytoplasmic tail, 1 | cl-42, nkat1, 47.11, p58.1, CD158a | L41267 |
| KIR2DL2 | killer cell immunoglobulin-like receptor, two domains, long cytoplasmic tail, 2 | cl-43, nkat6, CD158b1, p58.2 | L76669 |
| KIR2DL3 | killer cell immunoglobulin-like receptor, two domains, long cytoplasmic tail, 3 | cl-6, nkat2, nkat2a, nkat2b, p58.3, CD158b2 | L41268 |
| KIR2DL4 | killer cell immunoglobulin-like receptor, two domains, long cytoplasmic tail, 4 | 103AS, 15.212, CD158d, p70 | X97229 |
| KIR2DL5A | killer cell immunoglobulin-like receptor, two domains, long cytoplasmic tail, 5A | KIR2DL5.1, CD158f | AF217485 |
| KIR2DL5B | killer cell immunoglobulin-like receptor, two domains, long cytoplasmic tail, 5B | KIR2DL5.2, KIR2DL5.3, KIR2DL5.4 | AF217486 |
| KIR2DS1 | killer cell immunoglobulin-like receptor, two domains, short cytoplasmic tail, 1 | EB6ActI, EB6ActII, CD158h, p50.1 | X89892 |
| KIR2DS2 | killer cell immunoglobulin-like receptor, two domains, short cytoplasmic tail, 2 | cl-49, nkat5, 183ActI, CD158j, p50.2 | L76667 |
| KIR2DS3 | killer cell immunoglobulin-like receptor, two domains, short cytoplasmic tail, 3 | nkat7 | L76670 |
| KIR2DS4 | killer cell immunoglobulin-like receptor, two domains, short cytoplasmic tail, 4 | cl-39, KKA3, nkat8, CD158i, p50.3 | L76671 |
| KIR2DS5 | killer cell immunoglobulin-like receptor, two domains, short cytoplasmic tail, 5 | nkat9, CD158g | L76672 |
| KIR2DP1 | killer cell immunoglobulin-like receptor, two domains, pseudogene 1 | KIRZ, KIRY, KIR15, KIR2DL6 | AF204908 |
| KIR3DL1 | killer cell immunoglobulin-like receptor, three domains, long cytoplasmic tail, 1 | cl-2, NKB1, cl-11, nkat3, NKB1B, AMB11, KIR, CD158e1 | L41269 |
| KIR3DL2 | killer cell immunoglobulin-like receptor, three domains, long cytoplasmic tail, 2 | cl-5, nkat4, nkat4a, nkat4b, CD158k, p140 | L41270 |
| KIR3DL3 | killer cell immunoglobulin-like receptor, three domains, long cytoplasmic tail, 3 | KIRC1, KIR3DL7, KIR44, CD158z | AF352324 |

TABLE 1-continued

KIR Nomenclature

| KIR | Full name | Aliases | Accession ID |
|---|---|---|---|
| KIR3DS1 | killer cell immunoglobulin-like receptor, three domains, short cytoplasmic tail, 1 | nkat10, CD158e2 | L76661 |
| KIR3DP1 | killer cell immunoglobulin-like receptor, three domains, pseudogene 1 | KIRX, KIR48, KIR2DS6, KIR3DS2P, CD158c | AF204919, AF204915-AF204917 |

Neutralization of NKCIR-Associated NK Cell Inhibition

Anti-NKCIR antibodies also or alternatively can be characterized on the basis of their ability to block or neutralize NK inhibition and thereby potentiate NK cell activity against otherwise blocked target cells. As indicated above, anti-NKCIR antibodies that bind to at least one NKCIR for a sufficient amount of time to neutralize NKCIR-mediated inhibition of NK cell cytotoxicity in NK cells can be used in the context of this invention. Such anti-NKCIR antibodies may be used directly as therapeutic agents in a native form (e.g., without conjugation to a cytotoxic agent). A more particular advantageous feature of the invention is anti-NKCIR antibodies that cross-react with two or more NKCIRs and neutralize the inhibitory activity associated with some or all (typically preferably all) of such associated NKCIRs.

Neutralizing anti-NKCIR antibodies may partially or fully neutralize the NKCIR-mediated inhibition of NK cell cytotoxicity. Neutralization refers to any substantial blocking of otherwise present inhibitory signals. Neutralization can be measured by any suitable method. In one aspect, neutralization of inhibition is reflected in that the neutralizing anti-KIR antibody(ies) cause(s) an least about 20%, preferably at least about 30%, at least about 40%, at least about 50%, at least about 60%, at least about 75% or more (e.g., about 25-100%) increase in NK cell-mediated specific lysis in a particular mixture of NK and NK target cells compared to the amount of specific lysis that typically occurs in a substantially identical setting without the presence of the anti-NKCIR antibody(ies). The percentage increase in this aspect can be determined when considering anti-NKCIR or other antibodies by, e.g., comparison with the results of chromium release toxicity test assays obtained from a mixture of NK target cells and NK cells not blocked their associated NKCIR(s) (100%) and a mixture of NK cells and NK target cells, in which the NK target cells present a ligand for the NKCIR (0%). In the case of anti-KIR antibodies, comparison can be with the results of chromium release toxicity test assays obtained from a mixture of NK target cells and NK cells not blocked their associated KIR(s) (100%) and a mixture of NK cells and NK target cells, in which the NK target cells present the cognate MHC class I molecule for the inhibitory KIR on the NK cells (0%). In an advantageous aspect, the invention provides anti-NKCIR antibodies that induce lysis of cell(s) that would not be effectively lysed without the presence of such anti-NKCIR antibody. Alternatively, neutralization of NKCIR inhibitory activity can be indicated by, e.g., the results of a chromium assay using an NK cell clone or transfectant expressing one or several inhibitory NKCIRs (e.g., KIR, NKG2, NKG2A, and LIR (e.g., LILRB1, LILRB5)) and a target cell expressing only one ligand (e.g., HLA polypeptide or allele, HLA-E, etc.) that is recognized by one of the NKCIRs on the NK cell, where the level of cytotoxicity obtained with the antibody is at least about 20%, such as at least about 30%, at least about 40%, at least about 50%, at least about 60%, at least about 70% or more (e.g., about 25-100%) of the cytotoxicity observed with a known blocking antibody to the ligand of the NKCIR. For example, when testing an anti-KIR antibody, an anti-MHC class I molecule is administered in a substantially identical setting, such as W6/32 anti-MHC class I antibody that is currently available from, e.g., Research Diagnostics, Flanders, N.J., USA and described in, e.g., Shields et al., Tissue Antigens. 1998 May; 51(5):567-70.

Chromium release assays and other methods of assessing NK cell cytolytic activity are known in the art. Conditions suitable for such assays also are well known. A typical chromium release assay is performed by labeling target cells (e.g., Cw3 and/or Cw4 positive cell lines—at about, e.g., 5000 cells per well in a microtitration plate) with $Na_2{}^{51}CrO_4$ (such that $^{51}Cr$ is taken up and retained by viable target cells), washing to remove excess radioactivity, thereafter exposed to NK cells for a period of about 4 hours in the presence or absence of anti-NKCIR antibody(s) at a suitable effector:target ratio (e.g., about 4:1), and measuring for subsequent $^{51}Cr$ levels reflecting target cell death and lysis. An example of such an assay is described in, e.g., Moretta et al., 1993, J Exp Med 178, 597-604. In a similar assay, proliferating target cells can be labeled with $^3H$-thymidine, which is incorporated into the replicating DNA. Upon cytolytic action by NK cells, the DNA of the target cells is rapidly fragmented and retained in a filtrate, while large, unfragmented DNA can be collected on a filter, such that one can measure either the release of these fragments or the retention of $^3H$-thymidine in cellular DNA. Other examples and relevant discussion related to such assays can be found in, e.g., PCT application no. WO2006/072625.

In another aspect, the invention provides anti-NKCIR antibodies characterized by the ability to compete with cross-reactive and/or neutralizing anti-NKCIR antibodies for binding to cognate NKCIRs and/or to bind to the same antigenic determinant region/epitope as such known antibodies. The phrase "competes with" when referring to a particular monoclonal antibody (e.g., 1-7F9, etc.) means that the anti-NKCIR antibody competes with the referenced antibody or other molecule in a binding assay using either recombinant NKCIR molecules or surface expressed NKCIR molecules. For example, if an anti-KIR antibody detectably reduces binding of 1-7F9 to a KIR molecule normally bound by 1-7F9 in a binding assay, the anti-KIR antibody can be said to "compete" with 1-7F9. An anti-KIR antibody that "competes" with 1-7F9 may compete with 1-7F9 for binding to the KIR2DL1 human receptor, the KIR2DL2/3 human receptor, or both KIR2DL1 and KIR2DL2/3 human receptors.

Although often related, describing a protein in terms of competition with a reference binding protein versus the ability of the protein to bind to the same or substantially similar epitope as a reference protein in some cases imply significantly different biological and physiochemical properties. Competition between binding proteins implies that the test anti-NKCIR antibody binds to an epitope that at least partially overlaps with an epitope bound by an anti-NKCIR antibody or is located near enough to such an epitope so that such an anti-KIR antibody competes with known anti-NKCIR antibodies due to steric hindrance. An anti-NKCIR antibody may compete with a reference anti-NKCIR antibody, without binding to the same or similar epitope due to the large size of the antibodies. Such a competing anti-NKCIR antibody can be useful in blocking interactions associated with the same antigenic determining region as the reference anti-NKCIR antibody even though it binds a different antigenic determinant.

In another exemplary aspect, the invention provides an anti-NKCIR antibody that binds to substantially the same antigenic determinant region as an anti-NCKIR antibody, such as 1-7F9, DF200 and/or NKVSF1 (for KIR), or antibody Z199 (for NKG2A, available from Beckman Coulter, CA), etc.

Competition refers to any significant reduction in the propensity for a particular molecule to bind a particular binding partner in the presence of another molecule that binds the binding partner. Typically, competition means an at least about 15% reduction in binding, such as an at least about 20% reduction in binding (e.g., a reduction in binding of about 25% or more, about 30% or more, about 15-35%, etc.) between, e.g., an anti-KIR antibody and at least one KIR in the presence of the competing molecule, e.g., an anti-KIR antibody. In certain situations, such as in cases where epitopes belonging to competing antibodies are closely located in an antigen, competition can be marked by greater than about 40% relative inhibition of receptor (e.g., KIR) binding, at least about 50% inhibition, at least about 55% inhibition, at least about 60% inhibition, at least about 75% inhibition, or a higher level of inhibition, e.g., such as a level of inhibition of about 45-95%.

Assessing competition typically involves an evaluation of relative inhibitory binding using a first amount of a first molecule (e.g., an anti-KIR antibody); a second amount of a second molecule (e.g., a known anti-KIR antibody); and a third amount of a third molecule (e.g., a KIR), wherein the first, second, and third amounts all are sufficient to make a comparison that imparts information about the selectivity and/or specificity of the molecules at issue with respect to the other present molecules. Usually, for ELISA competition assays, about 5-50 µg (e.g., about 10-50 n, about 20-50 µg, about 5-20 µg, about 10-20 µg, etc.) of an anti-KIR antibody, a known anti-KIR antibody, and at least one KIR are used to assess whether competition exists. Conditions also should be suitable for binding of the competing molecules to their putative/known target. Physiological or near-physiological conditions (e.g., temperatures of about 20-40° C., pH of about 7-8, etc.) can typically be suitable for anti-KIR antibody:KIR.

Determination of competition (or relative inhibition of binding) between two or more molecules can be made by use of immunoassays in which the control NKCIR-binding molecule (e.g., 1-7F9) and test anti-NKCIR antibody are admixed (or pre-adsorbed) and applied to a sample containing relevant KIRs, such as both KIR2DL1 and KIR2DL2/3, each of which is known to be bound by DF200. Protocols based upon ELISAs, radioimmunoassays, Western blotting, and the like are suitable for use in such competition studies. Competition ELISAs are typically performed under conditions suitable for binding of the molecules (e.g., physiological conditions, particularly in the case of antibodies that bind conformational/nonlinear epitopes). Competition also can be assessed by, for example, a flow cytometry test, SPR analysis and other techniques found in, e.g., Harlow, et al., Antibodies: A Laboratory Manual, Cold Spring Harbor Laboratory Press, Cold Spring Harbor, N.Y., 1988), Colligan et al., eds., Current Protocols in Immunology, Greene Publishing Assoc. and Wiley Interscience, N.Y., (1992, 1993), Ausubel et al., Eds., Short Protocols in Molecular Biology, ($5^{th}$ edition), John Wiley & Sons (2002), and Muller, Meth. Enzymol. 92:589-601 (1983)).

An antigenic determinant region or epitope can be identified by a number of known techniques. For example, an antigenic determinant region can be identified quickly by "foot printing" assays, such as through a chemical modification of the exposed amines/carboxyls in target NKCIR proteins. One specific example of such a foot-printing technique is the use of hydrogen-deuterium exchange detected by mass spectrometry (HXMS), wherein a hydrogen/deuterium exchange of receptor and ligand protein amide protons, binding, and back exchange occurs, wherein the backbone amide groups participating in protein binding are protected from back exchange and therefore will remain deuterated. Relevant regions can be identified at this point by peptic proteolysis, fast microbore high-performance liquid chromatography separation, and/or electrospray ionization mass spectrometry. See, e.g., Ehring H, Analytical Biochemistry, Vol. 267 (2) pp. 252-259 (1999) and/or Engen, J. R. and Smith, D. L. (2001) Anal. Chem. 73, 256A-265A.

Another example of a suitable epitope identification technique is nuclear magnetic resonance (NMR) epitope mapping, where typically the position of the signals in two-dimensional NMR spectres of the free antigen and the antigen complexed with the antigen-binding peptide, such as an antibody, are compared. The antigen typically is selectively isotopically labeled with $^{15}N$ so that only signals corresponding to the antigen and no signals from the antigen binding peptide are seen in the NMR-spectrum. Antigen signals originating from amino acids involved in the interaction with the antigen binding peptide typically will shift position in the specters of the complex compared to the specters of the free antigen, and the amino acids involved in the binding can be identified that way. See, e.g., Ernst Schering Res Found Workshop. 2004; (44):149-67; Huang et al, Journal of Molecular Biology, Vol. 281 (1) pp. 61-67 (1998); and Saito and Patterson, Methods. 1996 June; 9(3): 516-24.

Epitope mapping/characterization also can be performed using mass spectrometry methods. See, e.g., Downward, J Mass Spectrom. 2000 April; 35(4):493-503 and Kiselar and Downard, Anal Chem. 1999 May 1; 71(9):1792-801.

Protease digestion techniques also can be useful in the context of epitope mapping and identification. Antigenic determinant-relevant regions/sequences can be determined by protease digestion, e.g. by using trypsin in a ratio of about 1:50 to NKCIR in an overnight digestion at 37° C. and pH 7-8, followed by mass spectrometry (MS) analysis for peptide identification. The peptides protected from trypsin cleavage by the anti-NKCIR-binder can subsequently be identified by comparison of samples subjected to trypsin digestion and samples incubated with antibody and then subjected to digestion by e.g., trypsin (thereby revealing a foot print for the binder). Other enzymes like chymotrypsin, pepsin, etc., also or alternatively can be used in similar epitope characterization methods. Moreover, enzymatic digestion can provide a quick method for analyzing whether a potential antigenic determinant sequence is within a region of the NKCIR in the context of an anti-NKCIR polypeptide that is not surface exposed and, accordingly, most likely not relevant in terms of antigenicity. See, e.g., Manca, Ann Ist Super Sanita. 1991; 27(1):15-9 for a discussion of similar techniques.

Various phage display techniques also can be used to identify epitopes. See, e.g., Wang and Yu, Curr Drug Targets. 2004 January; 5(1):1-15; Burton, Immunotechnology. 1995 August; 1(2):87-94; Cortese et al., Immunotechnology. 1995 August; 1(2):87-94; and Irving et al., Curr Opin Chem. Biol. 2001 June; 5(3):314-24. Consensus epitopes also can be identified through modified phage display-related techniques (see, Mumey et al., *J. Comput. Biol.* 10:555-567 and Mumey, *Proceedings of the Sixth Annual International Conference on Computational Molecular Biology (RECOMB-02)*, pp. 233-240 (ACM Press, New York)) for discussion (see also Bailey et al., *Protein Science* (2003), 12:2453-2475; Dromey et al., J. Immunol. 2004 Apr. 1; 172(7):4084-90; Parker et al., Mol Biotechnol. 2002 January; 20(1):49-62; and Czompoly et al., Biochem Biophys Res Commun. 2003 Aug. 8; 307(4):791-6).

Epitope mapping by competitive binding to a KIR with two KIR-binding molecules where one is biotinylated (e.g., a known anti-KIR antibody) or otherwise similarly labeled is another method for identifying relevant antigenic determinant regions.

Other methods potentially helpful in mapping epitopes include crystallography techniques, X-ray diffraction techniques (such as the X-ray diffraction/sequence study techniques developed by Poljak and others in the 1970s-1980s), and the application of Multipin Peptide Synthesis Technology.

Computer-based methods such as sequence analysis and three dimensional structure analysis and docking also can be used to identify antigenic determinants. For example, an epitope also can be determined by molecular modeling using a structure of a NKCIR or portion thereof with docking of the structure of the Fab fragment of an individual mAb. Where necessary, models of NKCIRs can be produced by homology modeling with structure-characterized NKCIRs using programs such as Molecular Operating Environment (MOE), which is available from Chemical Computing Group (Montreal, Quebec, Canada—www.chemcomp.com). These and other mapping methods are discussed in Epitope Mapping A Practical Approach (Westwood and Hay Eds.) 2001 Oxford University Press (see also, Cason, J Virol Methods. 1994 September; 49(2):209-19).

Characteristics of Anti-KIR Antibodies

Advantageous anti-KIR antibodies may be classified based on functional characteristics, particularly with respect to their ability to cross-react or cross-bind more than one KIR, such as more than one type of inhibitory KIR, and/or the ability to effectively neutralize NK inhibitory signals. The invention contemplates treatment using an anti-KIR or a combination of anti-KIR antibodies. Exemplary anti-KIR antibodies include, but are not limited to, an anti-KIR2DL1 antibody and an anti-KIR2DL2 antibody, or an anti-KIR2DL1 antibody and an anti-KIR2DL3 antibody, or an anti-KIR2DL1 antibody and an anti-KIR2DL2 antibody and an anti-KIR2DL3 antibody, or an anti-KIR antibody that binds at least two different human inhibitory KIR receptor gene products and is capable of neutralizing KIR-mediated inhibition of NK cell cytotoxicity in NK cells expressing at least one of the two different human inhibitory KIR receptors, or an anti-KIR2D antibody and an anti-KIR3D antibody.

Anti-KIR antibodies that effectively bind to more than one type of KIR are a particularly advantageous feature of the invention. In a particular exemplary aspect, the invention provides anti-KIR antibodies that bind to at least two inhibitory KIR receptors at the surface of NK cells. In an even more particular illustrative aspect, the invention provides anti-KIR antibodies that bind a common antigenic determinant region of human KIR2DL receptors. In a yet even further specific aspect, the invention provides an anti-KIR antibody that binds to KIR2DL1, KIR2DL2, and KIR2DL3 receptors.

The term "KIR2DL2/3" can be used to refer to either or both of the KIR2DL2 and KIR2DL3 receptors. These two receptors have a very high homology, are allelic forms of the same gene, and are considered by the art to be interchangeable in many respects. Accordingly, KIR2DL2/3 can be considered in certain respects to be a single inhibitory KIR molecule. While anti-KIR antibodies that cross-react with KIR2DL2/3 are within the invention, anti-KIR antibodies that have a KIR-binding profile that only included KIR2DL2 and KIR2DL3 are not considered "cross-reactive."

Because at least one of KIR2DL1 or KID2DL2/3 is present in at least about 90% of the human population, KIR2DL1-KIR2DL2/3 cross-reactive anti-KIR antibodies can promote or enhance NK activity against most of the HLA-C allotype-associated cells, respectively group 2 HLA-C allotypes and group 1 HLA-C allotypes. A composition comprising a single KIR antibodies having such cross-reactivity may be used in treatment and/or diagnosis of most human subjects, thereby eliminating the necessity of genetic profiling of the patient and reducing the amount of different antibodies that need to be administered to a patient to ensure an effective result.

Cross-reacting anti-KIR antibodies can have any suitable composition and can be obtained by a number of suitable techniques. For example, a cross-reactive anti-KIR antibody can comprise a number of KIR ligand and/or anti-KIR antibody sequences that bind to different KIRs, which may be associated by conjugation, multimerization, or (in the case of peptide ligands) by being comprised in a fusion protein. In another aspect, an anti-KIR antibody is provided that comprises anti-KIR antibody sequences from a cross-reacting anti-KIR antibody.

Cross-reacting anti-KIR antibodies, from which KIR-binding sequences can be obtained or derived, are known. An example of such an antibody is described in, e.g., Watzl et al., Tissue Antigens, 56, p. 240 (2000). Another example is antibody NKVSF1 (also referred to as pan2D mAb; recognizing a common epitope of CD158a (KIR2DL1), CD158b (KIR2DL2) and p50.3 (KIR2DS4)) having the variable region and CDR sequences shown in, e.g., FIG. 15, of PCT patent application WO2006/003179 (Innate Pharma; Novo Nordisk; University of Genoa). The monoclonal antibody DF200, which reacts with various members of the KIR family including KIR2DL1 and KIR2DL2/3 is another example of such a cross-reacting antibody. A hybridoma that produces DF200 has been deposited at the CNCM culture collection, as Identification no. "DF200", registration no. CNCM I-3224, registered 10 Jun. 2004, Collection Nationale de Cultures de Microorganismes, Institut Pasteur, 25, Rue du Docteur Roux, F-75724 Paris Cedex 15, France. Several additional monoclonal antibodies can be generated and demonstrated to be cross-reactive anti-KIR antibodies. Yet other examples are antibodies 1-7F9 and 1-4F1, described in WO2006/003179.

A cross-reactive anti-KIR antibody can have any suitable affinity and/or avidity for the two or more KIRs to which it binds. Affinity refers to the strength of binding of an anti-KIR antibody or other antigen-binding protein to an epitope or antigenic determinant. Typically, affinity is measured in terms of a dissociation constant $K_D$, defined as $[Ab] \times [Ag]/[Ab-Ag]$ where $[Ab-Ag]$ is the molar concentration of the antibody-antigen complex, $[Ab]$ is the molar concentration of the unbound antibody and $[Ag]$ is the molar concentration of the unbound antigen. The affinity constant $K_a$ is defined by $1/K_D$. Suitable methods for determining binding peptide specificity and affinity by competitive inhibition, equilibrium dialysis, and the like can be found in, e.g., Harlow, et al., Antibodies: A Laboratory Manual, Cold Spring Harbor Laboratory Press, Cold Spring Harbor, N.Y., 1988); Colligan et al., eds., Current Protocols in Immunology, Greene Publishing Assoc. and Wiley Interscience, N.Y., (1992, 1993), and Muller, Meth. Enzymol. 92:589-601 (1983).

Typically, an anti-KIR antibody provided by the invention has an affinity for at least one KIR in the range of about $10^4$ to about $10^{10}$ $M^{-1}$ (e.g., about $10^7$ to about $10^9$ $M^{-1}$). The term immunoreact herein typically refers to binding of an anti-KIR antibody to a KIR with a dissociation constant $K_D$ lower than about $10^{-4}$ M. For example, in a particular aspect the invention provides anti-KIR antibody that have an average disassociation constant $(K_D)$ of about $7 \times 10^{-9}$ M or more with respect to KIR2DL1 and KIR2DL2/3, as determined by, e.g., surface plasmon resonance (SPR) screening (such as by analysis with a BIAcore™ SPR analytical device). In a more particular exemplary aspect, the invention provides anti-KIR antibodies that have a KD of about $2 \times 10^{-9}$ M (e.g., about $0.1$-$4 \times 10^{-9}$ M) or more for KIR2DL2/3 and about $11 \times 10^{-9}$ M (e.g., about $7$-$15 \times 10^{-9}$ M) or more for KIR2DL1.

Affinity can be determined by any of the methods described elsewhere herein or their known equivalents in the art. An example of one method that can be used to determine affinity is provided in Scatchard analysis of Munson & Pollard, Anal. Biochem. 107:220 (1980). Binding affinity also may be determined by equilibrium methods (e.g., ELISA or radioimmunoassay (RIA)) or kinetics analysis (e.g., BIAcore™ analysis).

Anti-KIR antibodies also or alternatively can be characterized by exhibiting KIR binding with a disassociation constant of less than about 100 nM, less than about 50 nM, less than about 10 nM, about 5 nM or less, about 1 nM or less, about 0.5 nM or less, about 0.1 nM or less, about 0.01 nM or less, or even about 0.001 nM or less.

Avidity refers to the overall strength of the total interactions between a binding protein and antigen (e.g., the total strength of interactions between an anti-KIR antibody and a KIR). Affinity is the strength of the total noncovalent interactions between a single antigen-binding site on an antibody or other binding peptide and a single epitope or antigenic determinant. Avidity typically is governed by three major factors: the intrinsic affinity of the binding protein for the epitope(s) or antigenic determinant(s) to which it binds, the valence of the antibody or binding protein and antigen (e.g., an anti-KIR antibody with a valency of three, four, or more will typically exhibit higher levels of avidity for an antigen than a bivalent antibody and a bivalent antibody can will have a higher avidity for an antigen than a univalent antibody, especially where there are repeated epitopes in the antigen), and/or the geometric arrangement of the interacting components. Avidity typically is measured by the same type of techniques used to assess affinity.

In another aspect, the invention provides an anti-KIR antibody that cross-reacts with KIRs from two or more species. For example, in one aspect, the invention provides an anti-KIR antibody that cross-reacts with KIRs of humans and cynomolgus monkeys. In a particular aspect, the invention provides an anti-KIR antibody that cross-reacts with at least two human KIRs and also binds to NK cells of cynomolgus monkeys. Such an anti-KIR antibody can comprise sequences from or that are derived from antibody NKVSF1, which exhibits such a cross-reactivity profile. Such anti-KIR antibodies can be subjected to toxicity testing and other useful studies in cynomolgus monkeys, if needed.

Antibodies that are cross-reactive with a variety of KIRs can be used in the combination compositions and methods of the invention. Exemplary cross-reactivity profiles of such antibodies include antibodies that cross-react with KIRs 2DL1 plus 2DL2/3, 3DL1 plus 3DL2, 2DL1 (and 2DL2/3) plus 2DS4, and 2DL1 (and 2DL2/3) but not 2DS4.

Thus, for example, the inventive methods or compositions can comprise an anti-KIR antibody that binds KIR2DL1, KIR2DL2, and KIR2DL3 and reduces or blocks inhibition of KIR-mediated NK cell cytotoxicity, as described in, e.g., WO2005003168.

Exemplary anti-KIR antibodies useful in the combination methods and compositions of the invention include anti-KIR antibodies comprising a VL region that corresponds to that of anti-KIR antibody DF200, or consists essentially of such a VL region (by being substantially similar and retaining a similar binding profile and affinity), or a VL sequence/domain that is highly similar (e.g., at least about 90% identical or 95% identical) to the VL sequence of DF200. The VL sequence of DF200 is shown in WO2006/3179. Such anti-KIR antibodies also may alternatively be defined by comprising the set of light variable CDRs of DF200 (also shown in WO2006/3179). Such an antibody typically also will comprise either the VH domain of DF200 or a highly similar sequence (e.g., a sequence having high identity to the DF200 VH domain or otherwise consisting essentially of such a sequence) or at least the heavy variable CDRs of DF200 (shown in WO2006/3179).

As used herein, the term "percent sequence identity" or "sequence identity" refers to the percent identity between two sequences, which is a function of the number of identical positions shared by the sequences, i.e., % homology=# of identical positions/total # of positions×100, taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two amino acid sequences can be determined using the algorithm of E. Myers and W. Miller (Comput. Appl. Biosci., 4:11-17 (1998)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (J. Mol. Biol. 48:444-453 (1970)) algorithm which has been incorporated into the GAP program in the GCG software package (available at www.gcg.com), using either a Blossum 62 matrix or a PAM250 matrix, and a gap weight of 16, 14, 12, 10, 8, 6, or 4 and a length weight of 1, 2, 3, 4, 5, or 6.

In certain instances, the protein sequences of the present disclosure can be further used as a "query sequence" to perform a search against public databases to, for example, identify related sequences. Such searches can be performed using the XBLAST program (version 2.0) of Altschol, et al.

(1990) J. Mol. Biol. 215:403-10. BLAST protein searches can be performed with the XBLAST program, score=50, wordlength=3 to obtain amino acid sequences homologous to the antibodies of the invention. To obtain gapped alignments for comparison purposes, Gapped BLAST can be utilized as described in Altschul et al., (1997) Nucleic Acids Res. 25(17):3389-3402. When utilizing BLAST and Gapped BLAST programs, the default parameters of the respective programs (e.g., XBLAST and NBLAST) can be used. See, www.ncbi.nlm.nih.gov.

In another exemplary aspect, the combination composition or method of the invention includes an anti-KIR antibody comprising VH and VL sequences that correspond to or are highly similar to (e.g., consists essentially of) the VH and VL sequences of antibody 1-7F9 (shown in WO2006/3179) or at least comprises the VL and VH CDRs of 1-7F9.

Competition with Cross-Reactive and/or Neutralizing Anti-KIR Antibodies

In another aspect, the inventive methods or compositions are characterized by comprising an anti-KIR antibody that competes with one of these antibodies or one of the other anti-KIR antibodies described in the references incorporated herein (e.g., 1-7F9).

Antibodies that compete with exemplary anti-KIR antibodies, such as DF200, 1-7F9, and/or NKVSF1, can be identified using known screening assays. A number of such assays are routinely practiced and well known in the art (see, e.g., U.S. Pat. No. 5,660,827, which is specifically incorporated herein by reference). Protocols based on, e.g., ELISAs, radioimmunoassays, Western blotting, and the use of BIA-CORE analysis are suitable for use in such competition studies.

One can, e.g., pre-mix the control antibody (e.g., DF200, NKVSF1, or 1-7F9) with varying amounts of the test antibody (e.g., in ratios of about 1:1, 1:2, 1:10 or about 1:100) for a period of time prior to applying to a KIR antigen sample. Alternatively, the control and varying amounts of test antibody can simply be added separately and admixed during exposure to the KIR antigen sample. As long as one can distinguish bound from free antibodies (e.g., by using separation or washing techniques to eliminate un-bound antibodies) and control anti-body from the test antibody (e.g., by using species specific or isotype specific secondary antibodies or by specifically labeling the control antibody with a detectable label) one will be able to determine if the test antibody reduce the binding of the control antibody to the different KIR2DL antigens, indicating that the test antibody recognizes substantially the same epitope as the control. The binding of the (labeled) control antibody in the presence of a completely irrelevant antibody (that does not bind KIR) can serve as the control high value. The control low value can be obtained by incubating the labeled control antibody with the same but unlabelled control antibody, where competition would occur and reduce binding of the labeled antibody. In a test assay, a significant reduction in labeled antibody reactivity in the presence of a test antibody is indicative of a test antibody that recognizes substantially the same epitope, i.e., one that competes with the labeled control antibody. For example, any test antibody that reduces the binding of control antibody to one or both of KIR2DL1 and KIR2DL3 antigens by at least about 50%, such as at least about 60%, or more preferably at least about 70% (e.g., about 65-100%), at any ratio of control:test antibody between about 1:1 or 1:10 and about 1:100 is considered to be an antibody that competes with the control.

Competition can also be assessed by, for example, flow cytometry. In such a test, cells bearing a given KIR can be incubated first with a control antibody, and then with the test antibody labeled with a fluorochrome or biotin. The antibody is said to compete with control antibody if the binding obtained upon pre-incubation with saturating amount of control antibody is about 80%, preferably about 50%, about 40% or less (e.g., about 30%) of the binding (as measured by mean of fluorescence) obtained by the test antibody without preincubation with control antibody. Alternatively, an antibody is said to compete with the control antibody if the binding obtained with a labeled control antibody (by a fluorochrome or biotin) on cells preincubated with saturating amount of test antibody is about 80%, preferably about 50%, about 40%, or less (e.g., about 30%) of the binding obtained without preincubation with the test antibody.

A simple competition assay in which a test antibody is pre-adsorbed and applied at saturating concentration to a surface onto which either KIR2DL1 or KIR2DL2/3, or both, are immobilized also may be advantageously employed. The surface in the simple competition assay is preferably a BIACORE chip (or other media suitable for surface plasmon resonance analysis). The binding of a control antibody to the KIR-coated surface is measured. This binding to the KIR-containing surface of the control antibody alone is compared with the binding of the control antibody in the presence of a test antibody. A significant reduction in binding to the KIR2DL1 and KIR2DL2/3-containing surface by the control antibody in the presence of a test antibody indicates that the test antibody recognizes substantially the same epitope as the control antibody such that the test antibody "competes" with the control antibody. Any test antibody that reduces the binding of control antibody to both of KIR2DL1 and KIR2DL2/3 antigens by at least about 20% or more, at least about 40%, at least about 50%, at least about 70%, or more, can be considered to be an antibody that competes with the control antibody. Preferably, such test antibody will reduce the binding of the control antibody to each of at least the KIR2DL1, 2, and 3 antigens by at least about 50% (e.g., at least about 60%, at least about 70%, or more). It will be appreciated that the order of control and test antibodies can be reversed; i.e., the control antibody can be first bound to the surface and then the test antibody is brought into contact with the surface thereafter in a competition assay. Preferably, the antibody having higher affinity for KIR2DL1 and KIR2DL2/3 antigens is bound to the KIR2DL1 and KIR2DL2/3-containing surface first, as it will be expected that the decrease in binding seen for the second antibody (assuming the antibodies are competing) will be of greater magnitude. Further examples of such assays are provided in the Examples herein, and in e.g., Saunal and Regenmortel, (1995) J. Immunol. Methods 183: 33-41, the disclosure of which is incorporated herein by reference.

In another aspect, the inventive method or composition is characterized by inclusion of only antibodies that are not cross-reactive with more than one KIR. For example, monoclonal antibodies specific only for KIR2DL1 have been shown to block the interactions between KIR2DL1 and HLA-Cw4 allotypes, as well as similar HLA-C allotypes belonging to the same group as Cw4 (Moretta et al., J Exp Med. 1993; 178(2):597-604; the disclosure of which is incorporated herein by reference). In another example, monoclonal antibodies against KIR2DL2/3 have also been described that block the interactions of KIR2DL2/3 with HLACw3 (or the like) allotypes (Moretta et al., 1993, supra). Optionally, the antibody can be selected from the group consisting of GL183 (KIR2DL2/3/S2-specific, available from Immunotech, France and Beckton Dickinson, USA); EB6 (KIR2DL1/s1-specific, available from Immunotech, France and Beckton Dickinson, USA); AZ138 (KIR3DL1-specific, available from Moretta et al, Univ. Genova, Italy); Q66 (KIR3DL2-specific, available from Immunotech, France); and DX9, Z27 (KIR3DL1-specific, available from Immunotech, France and Beckton Dickinson, USA).

Epitopes

In additional aspects, the invention provides anti-KIR antibodies that are directed to particular antigenic regions and/or epitopes presented on various KIRs. In one exemplary aspect, the invention provides anti-KIR antibodies that specifically bind KIR2DL1 within a region defined by one or more of the amino acid residues selected from 105, 106, 107, 108, 109, 110, 111, 127, 129, 130, 131, 132, 133, 134, 135, 152, 153, 154, 155, 156, 157, 158, 159, 160, 161, 162, 163, 181, and 192. In another embodiment the invention provides anti-KIR antibodies that specifically bind to KIR2DL1 and KIR 2DL2/3 in a region defined by one or more of amino acid residues 105, 106, 107, 108, 109, 110, 111, 127, 129, 130, 131, 132, 133, 134, 135, 152, 153, 154, 155, 156, 157, 158, 159, 160, 161, 162, 163, 181, and 192 thereof.

In a further aspect, the invention provides anti-KIR antibodies that bind to KIR2DL1, but that bind to a mutant of KIR2DL1 in which R131 is Ala with significantly reduced binding affinity relative thereto (about 20% or less, about 30% or less, about 40% or less, about 50% or less, about 60% or less, about 70% or less, etc., of the affinity exhibited for KIR2DL1). In another aspect, the invention provides anti-KIR antibodies that bind to KIR2DL1 but that which bind to a mutant of KIR2DL1 in which R157 is Ala with relatively reduced binding affinity (about 20% or less, about 30% or less, about 40% or less, about 50% or less, about 60% or less, about 70% or less, etc., of the affinity exhibited for KIR2DL1). In another aspect, the invention provides anti-KIR antibodies that bind to KIR2DL1 and which binds a mutant of KIR2DL1 in which R158 is Ala with relatively reduced binding affinity (about 20% or less, about 30% or less, about 40% or less, about 50% or less, about 60% or less, about 70% or less, etc., of the affinity exhibited for KIR2DL1).

In a further aspect, the invention provides anti-KIR antibodies that bind to KIR2DL1 residues 131, 157, and 158.

In an additional aspect, the invention provides anti-KIR antibodies that bind to KIR2DS3(R131W), but not to wild type KIR2DS3. In yet another aspect, the invention provides anti-KIR antibodies that bind to KIR2DL1 and KIR2DL2/3 as well as KIR2DS4. In still another aspect, the invention provides anti-KIR antibodies that bind to both KIR2DL1 and KIR2DL2/3, but not to KIR2DS4.

To illustrate the use of anti-KIR antibody sequences in the composition and construction of anti-KIR antibodies, exemplary anti-KIR antibody sequences and antibody sequence variants will be described here. Amino acid and nucleic acid sequences of variable regions and CDRS of exemplary KIR antibodies DF200 and 1-7F9 are also disclosed in PCT application no. WO2006/003179, the disclosure of which is incorporated herein by reference.

In one exemplary aspect, the invention provides an anti-KIR antibody comprising a CDR-L1 sequence that consists or consists essentially of the sequence Lys Ala Ser Gln Asn Val Val Thr Tyr Val Ser (SEQ ID NO:43). In another aspect, the invention provides an anti-KIR antibody that comprises a CDR-L1 that consists or consists essentially of the sequence Thr Ala Ser Ser Ser Val Ser Ser Ser Tyr Leu Tyr (SEQ ID NO:44).

In another illustrative aspect, the invention provides an anti-KIR antibody that also or alternatively comprises a CDR-L2 sequence that consists or consists essentially of the sequence Gly Ala Ser Asn Arg Tyr Thr (SEQ ID NO:45). In a further aspect, the invention provides an anti-KIR antibody that also or alternatively comprises a CDR-L2 that consists or consists essentially of the sequence Ser Thr Ser Asn Leu Ala Ser (SEQ ID NO:46).

In another demonstrative facet, the invention provides an anti-KIR antibody that also or alternatively comprises a CDR-L3 that consists or consists essentially of the sequence Gly Gln Gly Tyr Ser Tyr Phe Tyr Thr (SEQ ID NO:47). In yet another aspect, the invention provides an anti-KIR antibody that also or alternatively comprises a CDR-L3 that consists or consists essentially of the sequence His Gln Tyr His Arg Ser Pro Pro Thr (SEQ ID NO:48).

As a further exemplary feature, the invention provides an anti-KIR antibody that comprises a CDR-H1 that consists or consists essentially of the sequence Gly Phe Ser Phe Thr Phe Tyr Gly Val His (SEQ ID NO:49).

In still another exemplary aspect, the invention provides an anti-KIR antibody that comprises a CDR-H2 that consists or consists essentially of the sequence Val Ile Trp Ser Gly Gly Asn Thr Asp Tyr Asn Ala Ala Phe Ile Ser (SEQ ID NO:50).

In yet another exemplary aspect, the invention provides an anti-KIR antibody that comprises a CDR-H3 that consists or consists essentially of the sequence Asn Pro Arg Pro Gly Asn Tyr Pro Tyr Gly Met Asp Tyr (SEQ ID NO:51).

In a different aspect, the invention provides an anti-KIR antibody that comprises a CDR-H1 that consists or consists essentially of the sequence Gly Tyr Thr Phe Thr Ser Tyr Trp Met His (SEQ ID NO:52).

In an additional aspect, the invention provides an anti-KIR antibody that comprises a CDR-H2 that consists or consists essentially of the sequence Thr Ile Tyr Pro Gly Asn Ser Asp Thr Asn Tyr Asn Gln Lys Phe Lys Gly (SEQ ID NO:53).

Another aspect of the invention is embodied by an anti-KIR antibody that comprises a CDR-H3 that consists or consists essentially of the sequence Pro Thr Thr Ala Thr Arg Ser Ser Ala Met Asp Tyr (SEQ ID NO:54).

The basic and novel properties of these CDR sequences is the ability to, in combination with other necessary CDR and FR sequences, bind to epitope(s) presented on one or more KIRs. As indicated above, it may be the case that certain residues in such sequences contribute little or nothing to KIR epitope binding. Moreover, it also or alternatively may be the case that such CDR sequences may tolerate one or a few insertions without impacting their epitope binding characteristics substantially (specificity and/or affinity). However, in another aspect of the invention significant changes can be made in such sequences to produce useful variants. Such changes are discussed further below.

These exemplary CDR sequences can be combined with one another, variant CDR sequences described below, or other anti-KIR CDRs (typically from KIR-binding anti-KIR antibodies). In one exemplary aspect, the invention provides an anti-KIR antibody that comprises most or all of the CDR sequences selected from SEQ ID NOS:43, 45, 47, 49, 50, and 51.

In another illustrative aspect, the invention provides an antibody comprising a light variable (VL) sequence consisting essentially of the sequence Met Glu Ser Gln Thr Leu Val Phe Ile Ser Ile Leu Leu Trp Leu Tyr Gly Ala Asp Gly Asn Ile Val Met Thr Gln Ser Pro Lys Ser Met Ser Met Ser Val Gly Glu Arg Val Thr Leu Thr Cys Lys Asn Ser Glu Asn Val Val Thr Tyr Val Ser Trp Tyr Gln Gln Lys Pro Glu Gln Ser Pro Lys Leu Leu Ile Tyr Gly Ala Ser Asn Arg Tyr Thr Gly Val Pro Asp Arg Phe Thr Gly Ser Gly Ser Ala Thr Asp Phe Thr Leu Thr Ile Ser Ser Val Gln Ala Glu Asp Leu Ala Asp Tyr His Cys Gly Gln Gly Tyr Ser Tyr Pro Tyr Thr Phe Gly Gly Thr Lys Leu Asp Ile Lys Arg (SEQ ID NO:55). The basic and novel properties of such a sequence are its contribution to KIR binding. It may be possible that some amino acids can be deleted, add, or substituted in this sequence without substantial impact to such properties.

In an additional exemplary aspect, the invention provides an antibody comprising a VL sequence consisting essentially of the sequence Met Asp Phe Gln Val Gln Ile Phe Ser Phe Leu Leu Ile Ser Ala Ser Val Ile Met Ser Arg Gly Gln Ile Val Leu Thr Gln Ser Pro Ala Ser Met Ser Ala Ser Leu Gly Glu Arg Val Thr Met Thr Cys Thr Ala Ser Ser Ser Val Ser Ser Ser Tyr Leu Tyr Trp Tyr Gln Gln Lys Pro Gly Ser Ser Pro Lys Leu Trp Ile Tyr Ser Thr Ser Asn Leu Ala Ser Gly Val Pro Ala Arg Phe Ser Gly Ser Gly Ser Gly Thr Ser Tyr Ser Leu Thr Ile Ser Ser Met Gln Ala Glu Asp Ala Ala Thr Tyr Tyr Cys His Gln Tyr His Arg Ser Pro Pro Thr Phe Gly Gly Gly Thr Lys Leu Glu Ile Lys Arg (SEQ ID NO:56).

The N-terminal portion of both SEQ ID NO:55 and SEQ ID NO:56 may be cleaved in a suitable host cell if the sequence is presented in an appropriate context (e.g., the first about 23 amino acids of SEQ ID NO:55 may be cleaved after acting as a signal sequence for the VL sequence where it is the entire content of the peptide at issue or represents an exposed N-terminal portion of a peptide). Accordingly, the invention also provides anti-KIR antibodies comprising VL sequences consisting essentially of N-terminal truncated versions of SEQ ID NO:55 and SEQ ID NO:56 (e.g., where about 20 amino acids of the N-terminal portion thereof have been removed).

In another aspect, the invention provides an anti-KIR antibody that also or alternatively comprises a variable heavy (VH) sequence consisting essentially of the sequence Met Ala Val Leu Gly Leu Leu Phe Cys Leu Val Thr Phe Pro Ser Cys Val Leu Ser Gln Val Gln Leu Glu Gln Ser Gly Pro Gly Leu Val Gln Pro Ser Gln Ser Leu Ser Ile Thr Cys Thr Val Ser Gly Phe Ser Phe Thr Pro Tyr Gly Val His Trp Val Arg Gln Ser Pro Gly Lys Gly Leu Glu Trp Leu Gly Val Ile Trp Ser Gly Gly Asn Thr Asp Tyr Asn Ala Ala Phe Ile Ser Arg Leu Ser Ile Asn Lys Asp Asn Ser Lys Ser Gln Val Phe Phe Lys Met Asn Ser Leu Gln Val Asn Asp Thr Ala Ile Tyr Tyr Cys Ala Arg Asn Pro Arg Pro Gly Asn Tyr Pro Tyr Gly Met Asp Tyr Trp Gly Gln Gly Thr Ser Val Thr Val Ser Ser (SEQ ID NO:57). The first 20 amino acid residues of this sequence can act as a signal sequence for a peptide consisting or consisting essentially of this sequence or a protein chain comprising this sequence positioned in an appropriate context. Accordingly, the invention also provides an anti-KIR antibody that comprises a VH sequence that consists essentially of a fragment of SEQ ID NO:57 that lacks the first about 1-20 residues thereof.

In further aspect, the invention provides an anti-KIR antibody that also or alternatively comprises a variable heavy (VH) sequence consisting essentially of the sequence Met Glu Cys Asn Trp Ile Leu Pro Phe Ile Leu Ser Val Thr Ser Gly Val Tyr Ser Glu Val Gln Leu Gln Gln Ser Gly Thr Val Leu Ala Arg Pro Gly Ala Ser Val Lys Met Ser Cys Lys Ala Ser Gly Tyr Thr Phe Thr Ser Tyr Trp Met His Trp Met Lys Gln Arg Pro Gly Gln Gly Leu Glu Trp Ile Gly Thr Ile Tyr Pro Gly Asn Ser Asp Thr Asn Tyr Asn Gln Lys Phe Lys Gly Lys Ala Lys Leu Thr Ala Val Thr Ser Thr Asn Thr Ala Tyr Met Glu Leu Ser Ser Leu Thr Asn Glu Asp Ser Ala Val Tyr Tyr Cys Ser Arg Pro Thr Thr Ala Thr Arg Ser Ser Ala Met Asp Tyr Trp Gly Gln Gly Thr Ser Val Thr Val Ser Ser (SEQ ID NO:58). The first 20 amino acid residues of this sequence can act as a signal sequence for a peptide consisting or consisting essentially of this sequence or a protein chain comprising this sequence positioned in an appropriate context. Accordingly, the invention also provides an anti-KIR antibody that comprises a VH sequence that consists essentially of a fragment of SEQ ID NO:58 that lacks about the first 1-20 residues thereof.

In one aspect, the invention provides an anti-KIR antibody that comprises a VL sequence that consists essentially of SEQ ID NO:55 or an N-terminal truncated portion thereof and a VH sequence that consists essentially of SEQ ID NO:57 or an N-terminal truncated portion thereof.

As already mentioned, suitable sequence variants of antigen-binding antibody sequences, such as anti-KIR antibody sequences, can be incorporated into antibodies of the invention. Variations in most types of antibody sequence may be suitable. Thus, for example, an anti-KIR antibody can comprise variant constant sequences and/or variant framework sequences.

In one aspect, the invention provides an anti-KIR antibody that comprises one or more variant CDR sequences (i.e., a CDR sequence that differs from similar wild-type CDR sequence by one or more amino acid insertions, deletions, additions, and/or substitutions that impact the biological and/or physiochemical properties of the sequence with respect to its wild-type relative sequence). See e.g., techniques disclosed in PCT application no. WO2006/072625. CDR, VH, and VL sequence variants can exhibit any suitable level of identity to one or more "parent" CDR, VH, and VL sequences, respectively, such as the CDR, VH, and VL sequences of anti-KIR mAb DF200 and/or anti-KIR mAb NKVSF1. Typically, a variant sequence that binds to an essentially identical antigenic determinant region as a parent will retain at least about 40% amino acid sequence identity to the parent sequence, such as about 50% or more, about 60% or more, about 70% or more, about 75% or more, about 80% or more, about 85% or more, about 90% or more, or at least about 95% (e.g., about 45-99%, about 55-99%, or about 65-99%) identity to the parent sequence. However, in some cases, particularly with respect to CDR sequences targeted to an essentially identical epitope, variants with even lower levels of identity can be suitable.

CDR, VH, and VL sequence variants that bind to different antigenic determinant regions or a different set (or "profile") of antigenic determinant regions also can be generated by any of the techniques described elsewhere herein (rational design, mutagenesis, directed evolution, etc.). In such instances, significantly lower levels of amino acid sequence identity to a parent sequence can be expected. For example, in the context of a CDR-L1, CDR-H1, CDR-H2, or CDR H3 variant having a different epitope binding profile from a parent sequence, as little as about 20-30% amino acid sequence identity to a parent CDR sequence may be exhibited in variants that contribute to binding of NKCAMRs, such as KIRs.

PCT application no. WO2006/072625 further provides variants of anti-KIR antibody sequences, including specific formulae for CDR and variable region sequences, the disclosures of which are incorporated herein by reference.

Typically, variants differ from "parent" sequences mostly through conservative substitutions; e.g., at least about 35%, about 50% or more, about 60% or more, about 70% or more, about 75% or more, about 80% or more, about 85% or more, about 90% or more, about 95% or more (e.g., about 65-99%) of the substitutions in the variant are conservative amino acid residue replacements. In the context of this invention, conservative substitutions can be defined by substitutions within the classes of amino acids reflected in one or more of tables 4, 5 and 6 of PCT patent application no. WO2006/072625 (Novo Nordisk AS and Innate Pharma SA). PCT application no. WO2006/072625, incorporated herein by reference, also describes additional conservative substitutions groupings; making substantial changes in function by selecting substitutions that are less conservative; principles useful in the design and selection of peptide variants; conservation in terms of hydropathic/hydrophilic properties; maintaining a structure of the variant peptide substantially similar to the structure of the parent peptide, including methods for assessing similarity of peptides in terms of conservative substitutions, hydropathic properties, weight conservation, secondary structure comparisons or similarity score, as determined by use of a BLAST program; other points of variation/divergence between a variant and a parent can be acceptable; advantageous sequence changes in CDRs; sequence variations that result in an altered glycosylation; hypervariable region insertions and to generate a variant antibody and more generally, CDR variants.

Identity in the context of amino acid sequences of the invention can be determined by any suitable technique, typically by a Needleman-Wunsch alignment analysis (see Needleman and Wunsch, *J. Mol. Biol.* (1970) 48:443-453), such as is provided via analysis with ALIGN 2.0 using the BLOSUM50 scoring matrix with an initial gap penalty of −12 and an extension penalty of −2 (see Myers and Miller, CABIOS (1989) 4:11-17 for discussion of the global alignment techniques incorporated in the ALIGN program). A copy of the ALIGN 2.0 program is available, e.g., through the San Diego Supercomputer (SDSC) Biology Workbench. Because Needleman-Wunsch alignment provides an overall or global identity measurement between two sequences, it should be recognized that target sequences which may be portions or subsequences of larger peptide sequences may be used in a manner analogous to complete sequences or, alternatively, local alignment values can be used to assess relationships between subsequences, as determined by, e.g., a Smith-Waterman alignment (*J. Mol. Biol.* (1981) 147:195-197), which can be obtained through available programs (other local alignment methods that may be suitable for analyzing identity include programs that apply heuristic local alignment algorithms such as FastA and BLAST programs). Further related methods for assessing identity are described in, e.g., International Patent Application WO 03/048185. The Gotoh algorithm, which seeks to improve upon the Needleman-Wunsch algorithm, alternatively can be used for global sequence alignments. See, e.g., Gotoh, J. Mol. Biol. 162:705-708 (1982).

Production of Antibodies

Monoclonal antibodies in particular may be made using the hybridoma method first described by Kohler et al., Nature, 256:495 (1975), or by other well-known, subsequently-developed methods (see, e.g., Goding, Monoclonal Antibodies: Principles and Practice, pp. 59-103 (Academic Press, 1986)). Hybridomas and other fusion cells may be formed by chemical fusion, electrical fusion, or any other suitable technique, with any suitable type of myelomas, heteromyelomas, phoblastoid cells, plasmacytomas or similar immortalized cell and any suitable type of antibody-expressing cell(s).

Transformed immortalized B cells also can be used to efficiently produce antibodies. Transformed B cells can be produced by standard techniques, such as transformation with an Epstein Barr Virus, or a transforming gene. (See, e.g., "Continuously Proliferating Human Cell Lines Synthesizing Antibody of Predetermined Specificity," Zurawaki, V. R. et al, in Monoclonal Antibodies, ed. by Kennett R. H. et al, Plenum Press, N.Y. 1980, pp 19-33.). Thus, stable and continuous and/or immortalized anti-NKCIR antibody-expressing cells and cell lines are another feature of the invention. A step of a method for producing anti-NKCIR antibodies can include, for example, a step of producing immortalized B cells producing an anti-AMR antibody and/or anti-STM antibody which are fused to appropriate partners to produce anti-NKCIR antibody (s) or which are sequenced and such sequences used to produce a recombinant anti-NKCIR antibody.

Cell lines available as hosts for recombinant protein expression are well known in the art and include many immortalized cell lines available from the American Type Culture Collection (ATCC). These include, inter alia, Chinese hamster ovary (CHO) cells, NSO, SP2 cells, HeLa cells, baby hamster kidney (BHK) cells, monkey kidney cells (COS), human hepatocellular carcinoma cells (e.g., Hep G2), A549 cells, and a number of other cell lines. Other cell lines that may be used are insect cell lines, such as Sf9 cells. When nucleic acids (or nucleic acid-containing vectors) encoding antibody genes are introduced into mammalian host cells, antibodies can be produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods. Antibodies may also be recovered from host cell lysates when directly expressed without a secretory signal.

The purification of antibodies from cell cultures, cell lysates, and transgenic animals or biological materials obtained therefrom (e.g., from the ascites fluid of a transgenic animal producing antibodies) can be achieved by application of any number of suitable techniques known in the art including, e.g., immunoaffinity column purification; sulfate precipitation; chromatofocusing; preparative SDS-PAGE, and the like.

Anti-NKCIR antibodies also can be produced in bacterial cells and eukaryotic unicellular microorganisms, such as yeast. Bacterial cell produced antibodies lack normal glycosylation and accordingly may be deficient in terms of ADCC functions and other aspects of the immune response that may otherwise be associated with essentially identical antibodies produced in mammalian cells and/or animals.

Suitable methods for purifying, screening and selection of antibodies can be used, including those described in WO 2006/072625. Screening and selection of anti-NKCIR antibodies can be accomplished by any suitable technique or combination of techniques. For example, a variety of immunoassay formats may be used to select antibodies that selectively bind with a particular protein, variant, or fragment. For example, solid-phase ELISA immunoassays are routinely used to select antibodies selectively immunoreactive with a protein, protein variant, or fragment thereof. See Harlow and Lane, supra. The binding affinity of a monoclonal antibody can, for example, be determined by the Scatchard analysis of Munson et al., Anal. Biochem., 107: 220 (1980).

Anti-NKCIR antibodies typically are screened for the ability to modulate NK cell activity, such as by inhibiting NKCIR-mediated signals, promoting activation of NK cells through NKCAR-mediated signals. A number of NK cell assays have been developed that can be useful in such contexts including, for example, flow cytometric screening methods. See, e.g., McGinnes et al., J Immunol Methods 80 1984 70-85. Methods relevant to culturing NK cells, assessing NK cells, and the like are known in the art. See, e.g., Campbell and Colonna, Natural Killer Cell Protocols (Methods in Molecular Biology Series vol. 121) (2000).

In the context of anti-NKCIR antibodies, NK cell neutralizing activity can be demonstrated by the capacity of an anti-NKCIR Antibody to reconstitute lysis of target cells by NKCIR-positive NK cells. Anti-NKCIR antibody-associated NK cell modulation (e.g., KIR inhibition) can also be assessed by various cell based cytotoxicity assays. Redirected killing is one experimental system for determining the capacity of a NK-cell receptor to induce cytotoxicity. NK cells coated with antibody specific for a candidate receptor are assessed for their ability to kill target cells that express an Fc receptor to which the antibody binds. In another variant, the NK cell activity modulation associated with an anti-KIR antibody can be assessed in a cytokine-release assay. Other biological activities associated with various anti-NKCIR antibodies also can be used to evaluate anti-NKCIR antibodies. For example, anti-NKCIR antibodies can be evaluated for their ability to induce, promote, and/or enhance antibody-dependent cellular cytotoxicity (ADCC) induced by $IgG_{2a}$, $IgG_3$, and some $IgG_1$ subclass antibodies that mediate ADCC. The ability to induce ADCC can be assessed using a chromium release assay.

Anti-NKCIR antibodies typically are used in and provided in an at least substantially pure form. A substantially pure molecule is a molecule that is the predominant species in the composition wherein it is found with respect to the class of molecules to which it belongs (e.g., a substantially pure antibody is the predominant protein species in the composition wherein it is found. A substantially pure species makes up at least about 50% of the type of molecule in the composition and typically will make up at least about 70%, at least about 80%, at least about 85%, at least about 90%, at least about 95%, or greater percentage of the species in the composition by weight. Commonly, a composition comprising an anti-NKCIR antibody will exhibit at least about 98%, 98%, or 99% homogeneity for the anti-NKCIR antibody in the context of all present peptide species in the composition or at least with respect to substantially active peptide species in the context of proposed use. For example, a peptide stabilizer/buffer such as an albumin may be intentionally included in a final pharmaceutical formulation, without impeding the activity of the anti-NKCIR antibodies, and, accordingly, may be excluded from such purity calculations. The presence of impurities that do not interfere with the fundamental activity also may be acceptable in the context of a substantially pure composition. Purity can be measured by methods appropriate for the given compound (e.g., chromatographic methods; agarose and/or polyacrylamide gel electrophoresis; HPLC analysis; etc.).

An isolated molecule refers to a molecule that is not associated with significant levels (e.g., more than about 1%, more than about 2%, more than about 3%, or more than about 5%) of any extraneous and undesirable biological molecules, such as non-anti-NKCIR antibody biological molecules contained within a cell, cell culture, chemical media, or animal in which the anti-NKCIR antibody was produced. An isolated molecule also refers to any molecule that has passed through such a stage of purity due to human intervention (whether automatic, manual, or both) for a significant amount of time (e.g., at least about 10 minutes, at least about 20 minutes, at least about one hour, or longer). In many of the various compositions provided by the invention, such as in a composition comprising one or more pharmaceutically acceptable carriers, an anti-NKCIR antibody can be present in relatively small amounts in terms of numbers of total molecular species in the composition (e.g., in the case of a composition comprising a large amount of a pharmaceutically acceptable carrier, stabilizer, and/or preservative). In some cases additional peptides, such as BSA, can be included in such a composition with a previously purified anti-NKCIR antibody. However, provided that such additional constituents of the composition are acceptable for the intended application of the anti-NKCIR antibody, such a composition can still be described as comprising an isolated anti-NKCIR antibody. In other words, the term "isolated" is not meant to exclude artificial or synthetic mixtures with other compounds or materials, such as may form part of a pharmaceutically acceptable preparation.

Pharmaceutically Acceptable Carriers

An anti-NKCIR antibody can be combined with one or more carriers (diluents, excipients, and the like) and/or adjuvants appropriate for one or more intended routes of administration to provide compositions that are pharmaceutically acceptable.

Anti-NKCIR antibodies may be, for example, admixed with lactose, sucrose, powders (e.g., starch powder), cellulose esters of alkanoic acids, stearic acid, talc, magnesium stearate, magnesium oxide, sodium and calcium salts of phosphoric and sulphuric acids, acacia, gelatin, sodium alginate, polyvinylpyrrolidine, and/or polyvinyl alcohol, and optionally further tableted or encapsulated for conventional administration. Alternatively, an anti-NKCIR antibody may be dissolved in saline, water, polyethylene glycol, propylene glycol, carboxymethyl cellulose colloidal solutions, ethanol, corn oil, peanut oil, cottonseed oil, sesame oil, tragacanth gum, and/or various buffers. Other carriers, adjuvants, and modes of administration are well known in the pharmaceutical arts. A carrier or diluent may include time delay material, such as glyceryl monostearate or glyceryl distearate alone or with a wax, or other functionally similar materials.

Pharmaceutically acceptable carriers generally include any and all suitable solvents, dispersion media, coatings, antibacterial and antifungal agents, isotonic and absorption delaying agents, and the like that are physiologically compatible with an anti-NKCIR antibody. Examples of pharmaceutically acceptable carriers include water, saline, phosphate buffered saline, dextrose, glycerol, ethanol, and the like, as well as combinations of any thereof. In many cases, it can be desirable to include isotonic agents, for example, sugars, polyalcohols such as mannitol, sorbitol, or sodium chloride in such a composition. Pharmaceutically acceptable substances such as wetting agents or minor amounts of auxiliary substances such as wetting agents or emulsifying agents, preservatives or buffers, which desirably can enhance the shelf life or effectiveness of the anti-KIR antibody, related composition, or combination. Suitability for carriers and other components of pharmaceutical compositions is determined based on the lack of significant negative impact on the desired biological properties of the antibody.

Anti-NKCIR antibody compositions, related compositions, and combinations according to the invention may be in a variety of suitable forms. Such forms include, for example, liquid, semi-solid and solid dosage forms, such as liquid solutions (e.g., injectable and infusible solutions), dispersions or suspensions, emulsions, microemulsions, tablets, pills, powders, liposomes, dendrimers and other nanoparticles (see, e.g., Baek et al., Methods Enzymol. 2003; 362:240-9; Nigavekar et al., Pharm Res. 2004 March; 21(3):

476-83), microparticles, and suppositories. Formulations and salts are further described in PCT application no. WO2006/072625.

Typically, compositions in the form of injectable or infusible solutions, such as compositions similar to those used for passive immunization of humans with other antibodies, are used for delivery of anti-NKCIR antibodies of the invention. A typical mode for delivery of anti-NKCIR antibody compositions is by parenteral administration (e.g., intravenous, subcutaneous, intraperitoneal, and/or intramuscular administration). In one aspect, an anti-NKCIR antibody is administered to a human patient by intravenous infusion or injection.

A composition for pharmaceutical use also can include various diluents, fillers, salts, buffers, detergents (e.g., a nonionic detergent, such as Tween-80), stabilizers (e.g., sugars or protein-free amino acids), preservatives, tissue fixatives, solubilizers, and/or other materials suitable for inclusion in a composition for pharmaceutical use. Examples of suitable components also are described in, e.g., Berge et al., J. Pharm. Sci., 6661), 1-19 (1977); Wang and Hanson, J. Parenteral. Sci. Tech: 42, S4-S6 (1988); U.S. Pat. Nos. 6,165,779 and 6,225,289; and other documents cited herein. Such a pharmaceutical composition also can include preservatives, antioxidants, or other additives known to those of skill in the art. Additional pharmaceutically acceptable carriers are known in the art (see e.g. references in WO2006/072625.

Treatment of Hematological Malignancies

The invention provides therapeutic methods for treating individuals having or having had a hematological malignancy or a hematological pre-malignancy. The treatment involves anti-NKCIR antibodies, anti-NKCIR antibody compositions, and/or related compositions, which are administered to an individual having minimal or non-detectable disease. The invention also provides preferred therapeutic regimens for administering the anti-NKCIR antibodies for such treatment of hematological malignancies, including leukemias (e.g., AML, CML, MDS) and myelomas (e.g., MM, SMM), and hematological pre-malignancies, such as MDS, SMM and MGUS.

The term "treatment" herein refers to the delivery of an effective amount of such a formulation with the purpose of preventing any symptoms or disease state to develop or with the purpose of preventing or postponing progression, easing, ameliorating, or eradicating such symptoms or disease states already developed. The term "treatment" is thus meant to include treatment of minimal or non-detectable disease in an individual, who (i) experienced a partial response or complete response after a first treatment, (ii) is in remission, (iii) suffered from a detectable disease (e.g., AML, MM, MDS), or (iv) has a pre-malignancy. Thus, the treatments contemplated include treatment of an individual having SMM or MGUS, but not yet having MM. Additionally, the treatments include treatment of an individual having MDS, but not having AML. The term "treatment" includes induction therapy and consolidation therapy.

The term "non-detectable disease" as used herein refers to a disease state in an individual where the biological and/or medical markers of the disease have fallen below the cytologically detectable level. For example, a patient having leukemia is said to have a "non-detectable disease" when the patient has a total body leukemia burden below the cytologically detectable level, i.e., approximately $10^9$ cells. By way of further example, a patient having myeloma is said to have a "non-detectable disease" when there is a substantial absence of bone marrow or blood findings of multiple myeloma and/or there is no evidence of serum and urine M protein components. The biological and/or medical markers of disease may be assessed using standard procedures. For example, serum and urine M protein levels may be assess using electrophoresis and/or immunofixation.

As used herein, the term "remission" refers to the partial or complete disappearance of the clinical and subjective characteristics of a chronic or malignant disease.

The terms "hematological pre-malignancy" and/or "hematological pre-malignancies" as used herein refer to pre-cancerous cells. These pre-cancerous cells are not yet malignant, but are posed to become malignant. Pre-cancerous cells may look different then normal cells, but they have not yet invaded surrounding tissue. Exemplary pre-malignancies include, but are not limited to, MDS, SMM, and MGUS.

The term "hematological malignancies" herein includes lymphoma, leukemia, myeloma or lymphoid malignancies, as well as cancers of the spleen and the lymph nodes. Exemplary lymphomas include both B cell lymphoma and T cell lymphoma. Non-limiting examples of B cell lymphomas include low grade/NHL follicular cell lymphoma (FCC), mantle cell lymphoma (MCL), diffuse large cell lymphoma (DLCL), small lymphocytic (SL) NHL, intermediate grade/follicular NHL, intermediate grade diffuse NHL, high grade immunoblastic NHL, high grade lymphoblastic NHL, high grade small non-cleaved cell NHL, bulky disease NHL, Waldenstrom's Macroglobulinemia, lymphoplasmacytoid lymphoma (LPL), mantle cell lymphoma (MCL), follicular lymphoma (FL), diffuse large cell lymphoma (DLCL), Burkitt's lymphoma (BL), AIDS-related lymphomas, monocytic B cell lymphoma, angioimmunoblastic lymphoadenopathy, small lymphocytic, follicular, diffuse large cell, diffuse small cleaved cell, large cell immunoblastic lymphoblastoma, small, non-cleaved, Burkitt's and non-Burkitt's, follicular, predominantly large cell; follicular, predominantly small cleaved cell; and follicular, mixed small cleaved and large cell lymphomas. Non-limiting examples of T cell lymphomas include extranodal T cell lymphoma, cutaneous T cell lymphomas, anaplastic large cell lymphoma, and angioimmunoblastic T cell lymphoma. Hematological malignancies also include leukemia, such as, but not limited to, secondary leukemia, chronic lymphocytic leukemia (CLL), acute myelogenous leukemia (AML), chronic myelogenous leukemia (CML), B-cell prolymphocytic leukemia (B-PLL), acute lymphoblastic leukemia (ALL) and myelodysplasia (MDS). Hematological malignancies further include myelomas, such as, but not limited to, multiple myeloma (MM) and smoldering multiple myeloma (SMM). Other hematological and/or B cell- or T-cell-associated cancers are encompassed by the term hematological malignancy. For example, hematological malignancies also include cancers of additional hematopoietic cells, including dendritic cells, platelets, erythrocytes, natural killer cells, and polymorphonuclear leukocytes, e.g., basophils, eosinophils, neutrophils and monocytes.

It should be clear to those of skill in the art that these pre-malignancies and malignancies will often have different names due to changing systems of classification, and that patients having lymphomas classified under different names may also benefit from the combined therapeutic regimens of the present invention.

In one exemplary aspect, the invention provides a method of reducing a hematological malignancy's progression in a mammalian host, such as a human patient, having a detectable level of cancer cells comprising administering an anti-NKCIR antibody, an anti-NKCIR antibody composition, or a related composition (e.g., a nucleic acid encoding an anti-NKCIR antibody), in an amount sufficient to detectably reduce the progression of the hematological malignancies in the host.

Disease or cancer progression can be defined by standard criteria for the particular type of disease. Progression is optionally determined by assessing the selective clonal expansion of initiated cells. Methods for detecting cancers and cancer progression can be achieved by any suitable technique, several examples of which are known in the art. Examples of suitable techniques include PCR and RT-PCR (e.g., of cancer cell associated genes or "markers"), biopsy, imaging techniques, karyotyping and other chromosomal analysis, immunoassay/immunocytochemical detection techniques, histological and/or histopathologic assays, cell kinetic studies and cell cycle analysis, flow cytometry, and physical examination techniques (e.g., for physical symptoms). Exemplary methods for detecting cancer and cancer progression include detecting cytogenetic aberrations, e.g., neoplastic genetic markers, by isolating a population of abnormal cells, isolating nucleic acid from the abnormal cells, and contacting the isolated nucleic acid with one or more oligonucleotides that target a genetic rearrangement. The contact detects the presence of a cytogenetic aberration, such as Immunoglobulin (Ig) and/or T cell receptor gene rearrangements.

Delivering anti-NKCIR antibodies to a subject (either by direct administration or expression from a nucleic acid therein, such as from a pox viral gene transfer vector comprising anti-NKCIR antibody-encoding nucleic acid sequence(s)) and practicing the other methods of the invention can be used to reduce, treat, prevent, or otherwise ameliorate any suitable aspect of cancer progression. The methods of the invention can be particularly useful in the reduction and/or amelioration of tumor growth (e.g., percentage of plasma cells in bone marrow, number of tumor cells in circulation), and any parameter or symptom associated therewith (e.g., M protein levels). Methods that reduce, prevent, or otherwise ameliorate such aspects of cancer progression, independently and collectively, are advantageous features of the invention.

A reduction of cancer progression can include, e.g., any detectable decrease in (1) the rate of normal cells transforming to neoplastic cells (or any aspect thereof), (2) the rate of proliferation of pre-neoplastic (e.g., SMM or MGUS) or neoplastic cells, (3) the number of cells exhibiting a pre-neoplastic and/or neoplastic phenotype, (4) the physical area of a cell media (e.g., a cell culture, tissue, or organ (e.g., an organ in a mammalian host)) comprising pre-neoplastic and/or neoplastic cells, (5) the probability that normal cells and/or preoplastic cells will transform to neoplastic cells, (6) the probability that cancer cells will progress to the next aspect of cancer progression (e.g., a reduction in metastatic potential), or (7) any combination thereof. Such changes can be detected using any of the above-described techniques or suitable counterparts thereof known in the art, which typically are applied at a suitable time prior to the administration of a therapeutic regimen so as to assess its effectiveness.

In another aspect, the invention provides a method of reducing the risk of cancer progression, reducing the risk of further cancer progression in a cell population that has undergone initiation, and/or providing a therapeutic regimen for reducing cancer progression in a human patient, which comprises administering to the patient one or more first treatments (e.g., induction therapy, such as a chemotherapeutic agent) in an amount and regimen sufficient to achieve a partial or complete response, and administering an amount of an Anti-NKCIR antibody or related composition (or applying a combination administration method) to the patient. The anti-NKCIR antibody is administered while the patient's response to the first treatment remains ongoing, e.g., when the patient is in remission or has minimal disease.

The anti-NKCIR compounds may be administered as a monotherapeutic agent or in combination with other therapeutic agents. The term "monotherapeutic agent", as used herein, refers to the medicament comprising the anti-NKCIR compound as being free of any other pharmaceutically active agents and/or no additional pharmaceutically active agents are used to treat the individual for the particular disease condition. Alternatively, in some embodiments of the invention, administration of the anti-NKCIR antibody or antibody fragment may be combined with other therapeutic agents. For example, a number of therapeutic agents are available for the treatment of cancers. The antibody compositions and methods of the present invention may be combined with any other methods generally employed in the treatment of the particular disease, particularly a tumor, cancer disease, or other disease or disorder that the patient exhibits. So long as a particular therapeutic approach is not known to be detrimental to the patient's condition in itself, and does not significantly counteract the activity of the antibody in a pharmaceutical composition of this invention, its combination with the present invention is contemplated.

In connection with cancer treatment, the pharmaceutical compositions of the present invention may be used in combination with classical approaches, such as surgery, radiotherapy, chemotherapy, and the like. The invention therefore provides combined therapies in which a pharmaceutical composition of this invention is used simultaneously with, be fore, or after surgery; or is administered to patients with, before, or after conventional chemotherapeutic, radiotherapeutic or anti-angiogenic agents, or targeted immunotoxins or coaguligands. Other anti-cancer agents may be given prior to, at the same time as, or following, administration of an anti-KIR antibody composition of this invention. In some situations, it may even be desirable to extend the time period for treatment significantly, where several days (e.g., 2, 3, 4, 5, 6 or 7), several weeks (e.g., 2, 3, 4, 5, 6, 7 or 8) or even several months (e.g., 1, 2, 3, 4, 5, 6, 7 or 8) lapse between the respective administration of the anti-cancer agent or anti-cancer treatment and the administration of an antibody composition of this invention. This might be advantageous in circumstances where the anti-cancer treatment was intended to substantially destroy the tumor, such as surgery or chemotherapy, and administration of an antibody composition of this invention was intended to prevent micrometastasis or tumor re-growth. It also is envisioned that more than one administration of either an anti-KIR antibody-based composition of this invention or the anti-cancer agent will be utilized. These agents may be administered interchangeably, on alternate days or weeks; or a cycle of treatment with an anti-KIR antibody composition of this invention, followed by a cycle of anticancer agent therapy. In any event, to achieve tumor regression using a combined therapy, all that is required is to deliver both agents in a combined amount effective to exert an antitumor effect, irrespective of the times for administration.

To practice combined anti-cancer therapy, one would simply administer to a patient an antibody composition of this invention in combination with another anti-cancer agent in a manner effective to result in their advantageous combined anti-cancer actions within the patient. When one or more agents are used in combination with an antibody-containing composition of this invention in a therapeutic regimen, there is no requirement for the combined results to be additive of the effects observed when each treatment is conducted separately. Although at least additive effects are generally desirable, any increased anti-cancer effect above one of the single therapies would be of benefit. Also, there is no particular requirement for the combined treatment to exhibit synergistic effects, although this is possible and advantageous.

The combined administration includes co-administration of separate formulations or a single pharmaceutical formulation, and consecutive administration of the anti-NKCIR antibody or antibody fragment and first treatment in either order. Preferably, all administered active agents simultaneously exert their biological activities.

Depending on the patient and the stage of the cancer, the first treatment may involve one or more of the following agents and/or therapies: surgery, radiotherapy, immunomodulatory agents, chemotherapeutic agents, hormone therapy, and anti-angiogenic agents. It may also be desirable to combine administration of the anti-NKCIR antibody or antibody fragments with administration of another antibody, e.g., an antibody directed against another tumor antigen associated with the particular cancer. For example, the anti-NKCIR antibody or antibody fragments may be administered in combination with Rituxan.

In terms of surgery, any surgical intervention may be practiced in combination with the present invention.

In connection with radiotherapy, any mechanism for inducing DNA damage locally within cancer cells is contemplated, such as gamma-irradiation, X-rays, UV irradiation, microwaves and even electronic emissions and the like. The directed delivery of radioisotopes to cancer cells is also contemplated, and this may be used in connection with a targeting antibody or other targeting means.

In other aspects, immunomodulatory agents or regimens may be administered in combination with or as part of the antibody compositions of the present invention. Preferred examples of immunomodulatory agents include cytokines. Various cytokines may be employed in such combined approaches. Examples of cytokines useful in the combinations contemplated by this invention include IL-alpha, IL-1 beta, IL-2, IL-3, IL-4, IL-5, IL-6, IL-7, IL-8, IL-9, IL-10, IL-11, IL-12, IL-13, IL-15, IL-21, TGF-beta, GM-CSF, M-CSF, G-CSF, TNF-alpha, TNF-beta, LAF, TCGF, BCGF, TRF, BAF, BDG, MP, LIF, OSM, TMF, PDGF, IFN-alpha, IFN-beta, IFN-gamma. Cytokines used in the combination treatment or compositions of this invention are administered according to standard regimens, consistent with clinical indications, such as the condition of the patient and relative toxicity of the cytokine. Other immunomodulatory compounds that may be administered in combination with, or, as part of, the antibody compositions of the present invention include antibodies that bind specifically to other inhibitory receptors on lymphocytes, including without limitation antibodies such as anti-CTLA4 antibodies, or anti-CD94JNKG2A antibodies (see, for example, U.S. published patent application 20030095965). Variants and derivatives of these molecules that are known in the art also or alternatively can be used in such methods, and incorporated into compositions of the invention, as appropriate.

In certain embodiments, the anti-KIR antibody-comprising therapeutic compositions of the present invention may be administered in combination with or may further comprise a chemotherapeutic or hormonal therapy agent. A variety of hormonal therapy and chemotherapeutic agents may be used in the combined treatment methods disclosed herein.

Exemplary chemotherapeutic agents include, but are not limited to, acetogenins (e.g., bullatacin and bullatacinone), adriamycin, alkylating agents, alkyl sulfonates, aziridines (e.g., benzodopa, carboquone, meturedopa, and uredopa), bisphosphonates (e.g., clodronate, etidronate, NE-58095, zoledronic acid/zoledronate, alendronate, pamidronate, tiludronate, and risedronate); dactinomycin, delta-9-tetrahydrocannabinol (dronabinol), ethylenimines and methylamelamines (e.g., altretamine, triethylenemelamine, trietylenephosphoramide, triethiylenethiophosphoramide and trimethylolomelamine), beta-lapachone; lapachol; colchicines; betulinic acid; camptothecin (e.g., topotecan, irinotecan, acetylcamptothecin, scopolectin, and 9-aminocamptothecin); bryostatin; callystatin; CC-1065 (e.g., adozelesin, carzelesin and bizelesin synthetic analogues); podophyllotoxin; podophyllinic acid; teniposide; cryptophycins (e.g., cryptophycin 1 and cryptophycin 8); dolastatin; duocarmycin (e.g., KW-2189 and CB1-TM1); eleutherobin; pancratistatin; a sarcodictyin; spongistatin; nitrogen mustards (e.g., chlorambucil, chlornaphazine, cholophosphamide, estramustine, ifosfamide, mechlorethamine, mechlorethamine oxide hydrochloride, melphalan, novembichin, phenesterine, prednimustine, trofosfamide, and uracil mustard); nitrosureas (e.g., carmustine, chlorozotocin, fotemustine, lomustine, nimustine, and ranimnustine); antibiotics such as the enediyne antibiotics (e.g., calicheamicin); dynemicin; esperamicin; neocarzinostatin chromophore and chromoprotein enediyne antibiotics (e.g., aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, and zorubicin); anti-metabolites (e.g., methotrexate and 5-fluorouracil (5-FU)); folic acid analogues (e.g., denopterin, methotrexate, pteropterin, trimetrexate); purine analogs (e.g., fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, and floxuridine); androgens (e.g., calusterone, dromostanolone propionate, epitiostanol, mepitiostane, and testolactone); antiadrenals (e.g., aminoglutethimide, mitotane, and trilostane); folic acid replenisher (e.g., frolinic acid); aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids (e.g., maytansine and ansamitocins); mitoguazone; mitoxantrone; mopidanmol; nitraerine; pentostatin; phenamet; pirarubiin; losoxantrone; 2-ethylhydrazide; procarbazine; polysaccharide K; razoxane; rhizoxin; sizofuan; spirogermanium; tenuazonic acid; triaziquone; 2,2',2'''-trichlorotriethylamine; trichothecenes (e.g., T-2 toxin, verracurin A, roridin A and anguidine); urethan; vindesine; dacarbazine; mannomustine; mitobronitol; mitolactol; pipobroman; gacytosine; arabinoside ("Ara-C"); thiotepa; taxoids (e.g., taxol, taxotere, paclitaxel, and doxetaxel); chloranbucil; gemcitabine; 6-thioguanine; mercaptopurine; methotrexate; platinum analogs (e.g., cisplatin and carboplatin); vinblastine; platinum; etoposide (VP-16); ifosfamide; mitoxantrone; vincristine; oxaliplatin; leucovovin; vinorelbine; novantrone; edatrexate; daunomycin; aminopterin; ibanronate; topoisomerase inhibitor RFS 2000; difluoromethylornithine (DMFO); retinoids (e.g., retinoic acid); capecitabine; and pharmaceutically acceptable salts, acids or derivatives of any of the above.

As will be understood by those of ordinary skill in the art, the appropriate doses of chemotherapeutic agents used in combination with the NKCIR inhibitory agent, e.g., anti-KIR antibody, will approximate those already employed in clinical therapies involving administration of the chemotherapeutic alone or in combination with other chemotherapeutics. Variation in dosage will likely occur depending on the condition being treated. The physician administering treatment will be able to determine the appropriate dose for the individual subject.

Anti-hormonal agents act to regulate, reduce, block, or inhibit the effects of hormones that can promote the growth of cancer. As mentioned above, the NKCIR inhibitory agents, e.g., anti-KIR antibodies, of the present invention may be used in combination with anti-hormonal agents. Exemplary anti-hormonal agents include, but are not limited to, LHRH agonists (e.g., leuprorelin, goserelin, triptorelin, and buserelin); anti-estrogens and selective estrogen modulators (SERMs) (e.g., tamoxifen, raloxifene, droloxifene, 4-hydroxytamoxifen, trioxifene, keoxifene, LY117018, onapristone, and toremifene); estrogen receptor downregulators (ERDs); anti-androgens (e.g., flutamide, nilutamide, cyproterone and bicalutamide); aromatase inhibitors (e.g., anastrozole, exemestane, letrozole, 4(5)-imidazoles, aminoglutethimide, megestrol acetate, formestanie, vorozole, and fadrozole); and progestagens (e.g., medroxy, chlormadinone and megestrol).

The present NKCIR inhibitory agents, e.g., anti-KIR antibodies, of this invention may be used in combination with any one or more anti-angiogenic therapies or may further comprise anti-angiogenic agents. Non-limiting examples of anti-angiogenic agents include neutralizing antibodies, antisense RNA, siRNA, RNAi, RNA aptamers and ribozymes, particularly those that inhibit expression of genes in signalling pathways implicated in aberrant cell proliferation, such as, for example, PKC-alpha, Raf, H-Ras, EGF-R, VEGF or VEGF-R.

The dosing regimen and dosages of these aforementioned chemotherapeutic drugs that are therapeutically effective will depend on the particular cancer being treated, the extent of the disease and other factors familiar to the physician of skill in the art and can be determined by the physician.

In a further aspect, the invention provides a method of promoting remission of a cancer in a mammalian host, such as a human patient, comprising administering a composition comprising an anti-NKCIR antibody, such as an anti-KIR antibody, to the host, so as to promote cancer remission in the host.

In an even further aspect, the invention provides a method for reducing the risk of developing a cancerous condition, reducing the time to onset of a cancerous condition, reducing the severity of a cancer diagnosed in the early stages, and/or reducing the affected area of a cancer upon development thereof in a mammalian host, comprising administering to a host a prophylactically effective amount of an anti-NKCIR antibody or related composition of the invention so as to achieve the desired physiological effect(s). Preferably the host has MDS, SMM or MGUS, and the cancerous condition is MM, wherein the anti-NKCIR antibody reduces the risk of developing MM and/or reduces the time to onset of MM.

NK cell count and activation markers are markedly increased in patients with SMM. Typically, the individual having SMM will not have been treated with a first treatment prior to treatment with the compound, e.g., an antibody that binds a NKCIR; however, the invention also envisages SMM patients having had a prior treatment with a non-NKCIR agent.

Without being bound by theory, it is believed that the inventive methods are most efficacious when used in an individual having minimal disease, as compared to a patient having a high tumor burden, as the methods are not particularly suitable for restoring NK cell function in individuals with signs and symptoms of disease. Consequently, in some embodiments involving pathologies other than pre-malignant conditions, such as SMM or MGUS, the patient is preferentially treated with a first treatment, such that the individual has minimal or non-detectable disease. For example, treatment with an induction therapy and optionally a consolidation therapy may result in disease remission or a complete response, enhancing the efficacy of the inventive methods.

In a further aspect, the invention provides a method of increasing the likelihood of survival over a relevant period in a human patient diagnosed with cancer. In another aspect, the invention provides a method for improving the quality of life of a cancer patient comprising administering to the patient a composition of the invention in an amount effective to improve the quality of life thereof. In a further aspect, inventive methods described herein can be applied to significantly reduce the number of cancer cells in a vertebrate host, such that, for example, the total number of tumor cells is reduced. In a related sense, the invention provides a method for killing preneoplastic and/or neoplastic cells in a vertebrate, such as a human cancer patient. Optionally, the cancer is a hematological malignancy selected from the group consisting of AML, CML, MM, SMM and MGUS.

In another aspect, the invention provides a use of a compound that inhibits a NKCIR for the preparation of a pharmaceutical composition for treating an individual having or previously having had a hematological pre-malignancy or hematological malignancy. In one embodiment of this use, the individual has minimal or non-detectable disease. In another embodiment, the individual has a hematological pre-malignancy. In a further embodiment, the individual has SMM (smoldering myeloma), MGUS (monoclonal gammopathy of undetermined significance), or MDS (Myelodysplastic Syndrome).

The invention also provides a compound that inhibits a NKCIR for use in treating an individual having or previously having had a hematological pre-malignancy or hematological malignancy.

Acute Myeloid Leukaemia (AML)

Acute myeloid leukaemia (AML) is, one of the most common types of leukaemia among adults in the United States and Europe, Approximately 11,930 new cases of AML are estimated to be diagnosed in the US in 2006, accounting for less than 1% of all cancers and 34% of all leukemias. The incidence of AML is low below the age of 40 but increases progressively with age, from approximately 1 per 100,000 at age 40 to more than 15 per 100,000 at age 75 and older. The median patient age for presentation of AML is 65 to 70 years. Successful treatment is far less common in elderly patients with AML than in younger patients. For elderly patients, 55-65 years or older, the median time from treatment (induction chemotherapy) to death is 5 to 10 months. Although complete remission rates are about 50%, the remissions are usually transient, and rarely last more than 12 months. The probability of remaining in remission 3 years after induction chemotherapy is less than 10%.

Age-associated differences in outcomes are related to co-morbidities and prognostic factors. Many elderly patients are unable to tolerate standard treatment with cytotoxic agents and their complications. Patients with age-related chronic cardiac, pulmonary, hepatic, or renal disorders are at greater risk of acute toxicity from chemotherapy.

Abnormal karyotypic features are common in AML. The importance of karyotype in defining the pathophysiology, natural history, and response to therapy in acute leukaemia is a key concept. The cytogenetic aberrations most often associated with treatment failure in young patients with AML (e.g. abnormalities of chromosome 5 or 7 or complex karyotypes) are considerably more common in the elderly, occurring in 32% to 57% of patients. In contrast, "favorable" cytogenetic abnormalities, such as t(8;21), t(15;17), or inv (16), are more common in younger patients and are responsible in part for their better disease-free survival. Certain biomarkers of disease progression that are commonly used in AML include the mutations in FLT3 and/or NPM1 mutations—the two most important prognostic biomarkers for karyotype normal AML. FLT3 is generally the single most important prognostic factor in AML. Approximately 25-35% of AML patients have a FLT3 mutation. Patients with FLT3 mutations have a worse outcome and response to standard chemotherapy.

Current Treatment of AML

The therapeutic strategy for most patients with AML has been divided into two general phases: induction therapy and post-remission therapy, shown in FIG. 1.

Induction Therapy

The first goal of therapy in AML is to induce complete remission (CR). Adult AML in remission is defined as a normal peripheral blood cell count and normocellular bone marrow with less than 5% blasts in the marrow and no signs or symptoms of the disease. In addition, there are no signs or symptoms of central nervous system leukaemia or other extramedullary infiltration.

Induction therapy aims to reduce the total body leukaemia burden to below the cytologically detectable level of approximately $10^9$ cells. A prerequisite for the achievement of complete remission is the attainment of marrow aplasia lasting typically 1 or 2 weeks after induction chemotherapy. However, at the time of complete remission, patients still have a significant however barely detectable leukemic burden remaining (minimal residual disease), requiring some form of post-remission therapy.

For more than 20 years, standard induction chemotherapy has included an anthracycline and cytarabine. The most common regimen combines 3 days of daunorubicin with 7 days of continuous infusion of cytarabine (3+7 regimen). In most prospective studies using this regimen, CR is achieved in 65% to 75% of patients younger than 60 years and in approximately 50% of those older than 60 years. The reduced likelihood of obtaining CR among older patients is the result of an increased risk of resistant disease as well as an increased risk of death from complications of pancytopenia. Other factors associated with the lower rate of CR after induction therapy includes the presence of adverse cytogenetics, preceding hematologic disorders, and poor performance status at diagnosis.

Given the relatively low response rate to standard therapy in elderly patients, dose-intensification induction therapy regimens have been attempted. To date, however, no induction regimen has been proven superior to the 3+7 regimen with respect to remission or mortality rates.

Post-Remission Therapy

Post-remission therapy aims at further reducing the residual leukemic cell number, which may be as high as $10^8$ to $10^9$ cells at initial CR. This may be achieved by either cytotoxic chemotherapy, causing significant myelosuppression, or by replacement of a patient's stem cells through allogeneic transplantation.

In elderly patients, representing the largest proportion of the AML population, chemotherapy with curative intent does not constitute a treatment option with a favourable risk-benefit profile, however consolidation chemotherapy is normally offered to elderly patients. Intensified consolidation or maintenance chemotherapy regimens for elderly AML patients have been tested in clinical trials, but have not proven beneficial. This is mainly due to chemotherapy-related toxicities in combination with age-related patient comorbidities. Therefore, patients who suffer from significant decreases in their performance status or significant organ toxicity in correlation to induction chemotherapy will not be candidates for intensified post-remission therapy.

Treatment of AML with Anti-NKCIR Compounds

Anti-NKCIR compounds can be administered advantageously as post-remission therapy. For example, patients having achieved a CR to prior therapy, e.g. following induction therapy and optionally consolidation therapy, can be treated with anti-NKCIR antibodies according to the doses and dosing schemes disclosed herein. In embodiment, the patient has a poor prognostic (e.g. is in a group having high risk of progression), for example the patient has a FLT3 or NpM1 mutation associated with poor prognostic. Anti-NKCIR treatment may be as monotherapeutic agent treatment or in combination with other agents used in the treatment of the disease. Preferably, however, anti-NKCIR antibodies will be administered without concomitant use of chemotherapeutic agents that have a negative effect on NK cell activity.

Smoldering Multiple Myeloma (SMM)

Smoldering Multiple Myeloma is defined since 2003 by using international consensus criteria (International Myeloma Working Group. Criteria for the classification of monoclonal gammopathies, multiple myeloma and related disorders: a report from the International Myeloma Working Group. Br J Haematol 2003; 121: 749-57):

a serum monoclonal protein of 3 g/dL or higher, and/or 10% or more plasma cells in the bone marrow, but no evidence of related organ or tissue impairment (no end organ damage including bone lesions) as well as related symptoms.

The Mayo Clinic group has refined these criteria to clarify that patients with only serum free chains should be excluded and that the plasma cells need to be clonal (Kyle R A, Rajkumar S V. Criteria for diagnosis, staging, risk stratification and response assessment of multiple myeloma. Leukemia 2009; 23: 3-9).

Current Treatment of SMM

No therapy of SMM is currently available. Current management of this medical condition is limited to a close follow-up enabling to diagnose early progression to an active MM deserving to be treated. Patients should be followed every 3 months during the first year in order to establish the pattern of evolution. A less frequent follow-up could be considered in non evolving patients with a stable M protein and, a low risk of progression, according to Kyle's prognostic criteria (Bladé J et al. J Clin Oncol 2010 28: 690-97).

SMM prevalence increases with age, the median age of the patients at diagnosis ranges from 65 to 70 years. SMM accounts for approximately 15% of all cases with newly diagnosed MM. Given the estimated incidence of MM in the US, among 20,000 new cases/year, no more than 3,000 new cases of SMM would be diagnosed in the US each year. However, most of SMM are currently not diagnosed, virtually all MM being likely preceded by SMM, as discussed below.

Convergent evidence suggest that NK cell is involved in MM immunosurveillance, including ex vivo data showed that activated NK cells are cytotoxic against malignant cells derived from MM. At an early stage of the disease myeloma cells widely express the above mentioned activating NK ligands (MICA and B, ULBP) and down-regulate the inhibitory HLA class-1 ligand (Carbone E et al. Blood 2005; 105: 251-58). Also, progression of low tumor burden to aggressive MM parallels with a quantitative decline and functional exhaustion of NK cells. NK cell count and activation markers are markedly increased in patients with MGUS as well as smoldering or early MM. In contrast NK cell count declines and NK cell become hyporesponsive to stimulation in patients with advanced MM (Carbone et al 2005; Sawanobori M et al. Acta Haematol 1997; 98: 150-54.

Two recent studies suggest that all MM are preceded by an asymptomatic monoclonal gammopathy of unknown significance (MGUS) characterized by both a serum M protein <3 g/dl and bone marrow plasma cell <10%. However, only half of the patients with MGUS progresses and, in this case, increase in the M protein is gradual, leading likely to SMM before overt MM. Patho-physiology of these plasma cell proliferations and mechanisms involved in the progression from MGUS to SMM and SMM to symptomatic MM are fare to be fully understood. However, the 2 main steps of a several hit pathogenic process have been well characterized:

The initially limited transformation of clonal plasma cells, which results from acquired genetic events. Plasma cells of MGUS, SMM have genetic and phenotypic profiles similar to myelomatous cells, distinguishing them clearly from their normal counterpart.

The gradual progression of MGUS to SMM and SMM to MM which seems to be linked not only to genetic events occurring in the neoplastic plasma cells, but also to an accumulation of changes in the bone marrow microenvironment.

Natural history was well described in a cohort of 276 patients with SMM followed by Kyle et al. group, concluding:

The cumulative probability of progression to symptomatic and incurable malignancies was 73% at 5 years. Most of the patients developed a MM, while only 2% progressed to a primary amyloidosis (AL).

The overall risk of progression in SMM was greatly influenced by the time since diagnosis. It was approximately 10% per year in the first 5 years but only 3% per year in the next 5 years with a decrease to 1% per year thereafter. The median time to progression (TTP) has ranged between 2 and 3 years.

The risk of progression was significantly affected by the level of monoclonal protein, the proportion of bone marrow plasma cells, or both. As shown, below, there were substantial differences, in the median time of progression between the 3 prognostic groups created by using these 2 variables. In the high risk group, 87% progressed to overt malignancies at 15 years, and median time of progression was as short as 2 years. In contrast, in the low risk group, only 39% of the persons progressed with a median time of 19 years.

TABLE 2

| Time to progression | Number of patients (n %) | Median years | Progression at 15 years (%) |
| --- | --- | --- | --- |
| Group 1<br>Serum M spike ≥3 g/dl<br>BMPC ≥10% | 106 (38%) | 2 | 87 |
| Group 2<br>Serum M spike <3 g/dl<br>BMPC ≥10% | 143 (52%) | 8 | 70 |
| Group 3<br>Serum M spike ≥3 g/dl<br>BMPC <10% | 27 (10%) | 19 | 39 |
| Total population<br>P < 0.001 n multivariate analysis | 276 (100%) | 5 | 73 |

Table 2 shows the Probability of progression to Active Multiple myeloma (from Kyle R A et al. N Engl J Med 2007; 356: 2582-90)

Other factors of progression have been identified in additional studies and are mentioned in the below table. Recent data especially highlight the importance of 2 immunological predictors, which may improve the prognostication of SMM:

An abnormal free light chain ratio (FLC), at breakpoints lower than 0.126 or higher than 8, appeared to be an independent risk factor. As shown by working in the same Mayo cohort, incorporation of FLC resulted in an improved classification with a more balanced distribution of patients, as compared to the initial classification which only took into account levels of serum M protein and percentage of bone marrow plasma cell.

An aberrant phenotype of bone marrow plasma cells BMPC, and, as also shown in older studies, a so called immunoparesis, defined as decrease in one or two of the uninvolved Ig isotypes. Based on these 2 parameters, a scoring system was proposed with accumulative progression of SMM to MM of 4%, 46% and 72%, when none, one or two factors, respectively, were present. However, characterization of BMPC phenotype by flow cytometry remains cumbersome, and potentially difficult to reproduce from one team to the other.

Finally, patients with a so called evolving SMM, i.e. a progressive increase in the serum M protein value have a shorter time to progression to symptomatic MM than patients with a stable M protein (median 1.3 versus 3.9 years).

Table 3 shows the main factors of progression. Treatment with anti-NKCIR antibodies may be:

TABLE 3

Main factors of progression
Predictors of SMM progression

Before the IMWG consensus criteria

M protein levels
BMPC percentage
Light chain proteinuria (>50 mg/24 h)
IgA isotype
MRI abnormalities of the spine
Labeling index of bone marrow plasma cell (BMPC)

Using IMWG consensus criteria

M protein levels
BMPC percentage
Abnormal free light chain ratio

TABLE 3-continued

Main factors of progression
Predictors of SMM progression

Percentage of phenotypically abnormal
BMPC
Imunoparesis
Evolution pattern

Treatment of SMM with Anti-NKCIR Compounds

Anti-NKCIR compounds can be administered advantageously to patients having SMM or MGUS e.g. as defined by standard International Myeloma Working Group definitions. In embodiment, the patient has a poor prognostic (e.g., is in a group having high risk of progression), for example the patient has a mutation associated with poor prognostic or is in Group 1 according to the grouping in Table 2. Optionally, the patients having one or more defined risk factors of progression to MM can be treated, for example patients falling within Groups 1, 2 or 3 can be identified or selected based on probability of progression to active multiple myeloma (see, e.g. criteria of Kyle R A et al. N Engl J Med 2007; 356: 2582-90) and treated with an anti-NKCIR compound. Patients can be treated with anti-NKCIR antibodies according to the doses and dosing schemes disclosed herein. Anti-NKCIR treatment may be as monotherapeutic agent treatment or in combination with other agents used in the treatment of the disease. Preferably, however, anti-NKCIR antibodies will be administered in without concomitant use of chemotherapeutic agents that have a negative effect on NK cell activity.

Multiple Myeloma (MM)

Multiple myeloma is the second most frequent hematological cancer (19,900 new cases in the US in 2007, and a comparable number in Western Europe). MM results from the malignant proliferation of plasma cells which produces in most but not all the cases a clonal immunoglobulin, the so called M-protein. MM is characterized by skeletal destruction, hypocalcaemia, bone marrow and renal failure. Accurate consensual criteria are used internationally to define MM Kyle and Rajkumar, 2009.

Current Treatment of MM

Historical treatments consist of cytoreductive therapies, the so called "induction" by high doses corticosteroids and conventional anti mitotic chemotherapies including alkylating agents or the less potent (but less myelotoxic) combination of adriamycin and vincristine.

The most potent treatments were followed, after induction, of an "intensification" step (also called high dose chemotherapy), usually by the administration of high doses of the melphalan alkylator (200 mg/m2). Their myelotoxicity requires a hematological rescue by transplantation of autologous hematopoietic cells, which shortens the aplastic phase. Haematopoietic cells are usually mobilized from bone marrow towards peripheral blood by GCSF and/or cyclophosphamide administered at the end of the induction phase. Intensification is however only acceptable, for safety reason, in patients <65 years old without major co-morbidity.

Such intensified treatments enabled with historical induction treatments to achieve VGPR and PR in no more than 10-20% of the patients. Without intensification, and thus in patients >65 years old, complete response (CR) and very good partial response (VGPR) were rarely achieved. Five large randomised studies enabled to demonstrate the superiority of intensified based regimens, as compared to chemotherapies, in terms of response, progression free survival, and in 3 cases of overall survival (reviewed in Attal et al., 2007.

Two new classes of immunomodulating drugs, "Imids", e.g., thalidomide and lenalidomid, and proteasome inhibitors, e.g., bortezomib, emerged within the last years and are mainly used as part of combined therapies with corticosteroids or cytotoxic chemotherapies. Both drug classes combine at least 2 effects: a cytoreduction and a modulation of plasma cell microenvironment. Combination of these new drugs with steroids and conventional chemotherapies, including high dose chemotherapies, enabled to improve dramatically the response rate and especially the rate of VGPR or CR. However, molecular remission with an undetectable minimal residual disease appears, when it can be documented, to be very rare, achieved in less than 10% of the patients in these conditions, patients who achieve CR ineluctably relapse after a few years.

First relapse responds at least in 50% of the cases to treatment, but second or subsequent relapses become ultimately refractory to any available treatment. Thus, the disease remains incurable, except, in the few young patients who are successfully transplanted with allogenic hematopoietic cells. The toxicity of the procedure limits however drastically its indications.

Current treatments remain limited to symptomatic patients. The benefit of any treatment on progression or survival of the asymptomatic patients has not yet been demonstrated. Indications of treatments are consensually defined:

In patients >65 years old or with major co-morbidity, the historical treatment consisted of a dual induction therapy: melphalan+prednisone (MP). Several studies showed that a combination of MP with any of the 3 new agents (thalidomide, bortezomib or lenalidomid) is superior to standard MP. Other combinations are currently tested including lenalidomid+dexamethasone (Dex), and lenalidomid+bortezomib+Dex. which may even lead to better results. In patients <65 years old and without major co-morbidity, treatment begins as previously by an induction, enabling to reduce tumour burden before stem cell harvesting and intensification with add back of the autologous hematopoietic cells. Consolidation by the repetition of cytoreductive chemotherapies combining Imids and Protease Inhibitors after autologous HCT has just begun to be explored.

Assessment of Disease Response

International uniform response criteria of the IMWG (International MM Working Group), as published in Leukemia in 2006 by a panel of leaders in the field should now be used in all trials.

Responses can be assessed by various methods, including molecular remission (for instance defined as <1 malignant cell/10,000 BM cells), typically involving detecting and quantify the minimal residual disease of patients in CR using real time PCR from bone marrow samples with allelic specific oligonucleotides. Multiparametric flow cytometry is also used. Other methods include quantifying free light chains can be quantified in serum, and immunological assessment of bone marrow.

Complete and partial responses to induction, consolidation (including intensification) therapies can be assessed according to standard guidelines (e.g., IMWG guidelines). Patients with a CR, PR or VGPR may be treated with the anti-NKCIR antibodies of the invention.

Treatment of MM with Anti-NKCIR Compounds

Anti-NKCIR compounds can be administered advantageously as post-induction (and/or consolidation and/or intensification) therapy following treatment using chemotherapy and/or treatment with an immunomodulator (e.g. Imid or proteosome inhibitor), in patients that have experienced a partial or complete response to such induction and/or optionally consolidation therapy and thus have minimal disease. Patients having achieved response or remission following therapy, e.g. following induction therapy and optionally consolidation therapy, can be treated with anti-NKCIR antibodies according to the doses and dosing schemes disclosed herein. Anti-NKCIR treatment may be as monotherapeutic agent treatment or in combination with other agents used in the treatment of the disease. Preferably, however, anti-NKCIR antibodies will be administered in without concomitant use of chemotherapeutic agents that have a negative effect on NK cell activity.

Dosing and Dosage Regimens of Anti-NKCIR Antibodies

In one aspect, the methods of treatment the invention provides comprise administering to an individual a composition comprising an anti-NKCIR antibody in a therapeutically effective amount. A therapeutically effective amount may be for example a dosage of about 0.0003 mg (antibody)/kg (patient weight) to about 3 mg/kg (e.g., about 0.003 mg/kg to about 3 mg/kg, such as about 0.015 to about 3 mg/kg, e.g., any of about 0.075 mg to about 3 mg/kg, about 0.3 mg/kg to about 3 mg/kg, and about 1 mg/kg to about 3 mg/kg, or any of about 0.0003 mg/kg, about 0.003 mg/kg, about 0.015 mg/kg, about 0.075 mg/kg, about 0.3 mg/kg, about 1 mg/kg, and about 3 mg/kg). Doses and formulations of anti-KIR antibodies are described in PCT application No. WO2008/084106, the disclosure of which is incorporated herein by reference. In one embodiment, the method comprises repeating the administration at least once, for example with a dosing frequency in the range of 3 times per day to once per 2 months. The dose may also be administered, e.g., at least 3 times, at least 6 times, or at least 10 times. In one embodiment, the antibody is administered intravenously. In another embodiment, binding of the antibody to an inhibitory KIR on the surface of an NK cell potentiates the cytotoxic activity of the NK cell. In yet another embodiment, the antibody is a cross-reactive anti-KIR antibody. For example, the antibody may be antibody 1-7F9 in a formulation as described in PCT application no. WO2008/084106.

In one preferred embodiment, the dose is selected to provide substantially complete saturation in human patients. As used herein, the term "substantially complete saturation" refers to at least 90% occupancy of the targeted NKCIR, and preferably at least 95% receptor occupancy. The method optionally includes assessing the patient for NK cell potentiation and/or anti-tumor activity (which may be performed by use of any suitable technique, several of which being known in the art, including, e.g., NKCIR occupancy level, CD107a marker, etc., as described herein). The formulation is typically administered by i.v. administration over a suitable period of time, such as about 1 hour.

For example, an anti-NKCIR antibody can be administered at a dose and a dosing frequency achieving at least about 90%, preferably at least about 95% NKCIR occupancy on NK cells in plasma for at least about one, two, three or six months, thereby having sustained saturation for an extended period of time (e.g., at least 3 months, 6 months). In separate embodiments, the dose is in the range from about 0.1 to about 3 mg/kg, from about 0.3 to about 3 mg/kg, from about 0.1 to about 1 mg/kg and from about 1 to about 3 mg/kg, further preferably wherein the antibody is an anti-KIR antibody, further preferably wherein the antibody is 1-7F9. The dosing frequency may be in the range of once per day to once per 2 months, from about once per week to about once per 2 months; or about once per month. Alternatively, the dosing frequency can be selected from about three times, about twice, and about once per day; about five times, about four times, about three times, and about twice per week; and about once every two, four, and six weeks.

In one preferred embodiment, a dose of anti-NKCIR antibody resulting in substantially complete receptor saturation (e.g., at least about 90% or 95% receptor occupancy) is administered from about 2 times per week to about once per month, or from about once per month to about once per 2 months. The dose can be, e.g., administered at least 3 times, at least 6 times, or more. For example, the method may comprise administering an anti-NKCIR antibody at a dose and a dosing frequency achieving at least about 90% or 95% NKCIR occupancy on NK cells for at least about two weeks, one month, 6 months, 9 months or 12 months.

In one preferred embodiment, a regimen results in sustained substantially complete receptor saturation. A dose of anti-NKCIR antibody resulting in substantially complete receptor saturation for a period of at least about 1 week, 2 weeks or 1 month is administered. When the dose results in substantially complete receptor saturation (e.g., at least about 90% or 95% receptor occupancy) for about one week, the dose may be administered for example between once per week and once every two weeks; when the dose results in substantially complete receptor saturation for about two weeks, the dose may be administered for example between once every two weeks and once per month. When the dose results in substantially complete receptor saturation for about two weeks to about one month, the dose may be administered for example about once per month. In each regimen, the dose can be, e.g., administered at least 3 times, at least 6 times, or more. For example, the method may comprise administering an anti-NKCIR antibody at a dose and a dosing frequency achieving at least about 95% KIR occupancy on NK cells for at least about 6 months, 9 months or 12 months.

In another preferred embodiment, a regimen results in intermittent substantially complete receptor saturation. A dose of anti-NKCIR antibody resulting in substantially complete receptor saturation (e.g. at least about 90% or 95% receptor occupancy) for a period of at least about 1 week, 2 weeks or 1 month is administered. When the dose results in substantially complete receptor saturation for about one to two weeks, the dose may be administered for example about once per month or once per period of at least two months (e.g., once every two months). When the dose results in substantially complete receptor saturation for about two weeks to about one month, the dose may be administered for example about once per period of at least two months (e.g., once every two months). In separate embodiments, the dose is in the range from about 0.1 to about 0.3 mg/kg, administered about once per month; in one embodiment, the dose is in the range of about 0.1 to about 3 mg/kg, preferably 1 to about 3 mg/kg, administered about once every about two months (or once per period of more than two months, that is, less than once per two month period), further preferably wherein the antibody is an anti-KIR antibody, further preferably wherein the antibody is 1-7F9. The treatment can be repeated such that the treatment regimen results in intermittent substantially complete receptor saturation for a period of at least 6 months, 9 months or 12 months.

The antibody is typically administered intravenously, but other suitable administration modes are known, and also described in, e.g., WO2008/084106.

While anti-KIR antibody 1-7F9 or its S241P variant is a preferred antibody for modulating NK cell activity and/or treatment of disease, other anti-NKCIR and anti-KIR antibodies may also be used in the methods according to the invention. Such antibodies should, however, have similar $K_D$ values, similar clearance in a patient, and a similar volume of distribution, as anti-KIR antibody 1-7F9, where "similar" means within about 50%, preferably within about 30% of the corresponding anti-KIR antibody 1-7F9 parameter. Anti-KIR antibody 1-7F9 has a high affinity $K_D$ of about 4 ng/ml, and low affinity $K_D$ of about 20 ng/ml for doses up to 0.015 mg/kg; a clearance of about 0.5 ml/h/kg, and a volume of distribution of about 115 ml/kg (see WO2008/084106). An exemplary anti-NKCIR antibody useful in one or more methods of the invention may have the following properties: (a) reduces or blocks the signalling of an inhibitory NKCIR on NK cells; (b) a high affinity $K_D$ from about 2 to about 6 ng/ml; (c) a low affinity $K_D$ from about 10 to about 30 ng/ml; (d) a clearance of from about 0.25 to about 0.75 ml/h/kg, (e) a volume of distribution of from about 50 ml/kg to about 175 ml/kg. Anti-NKCIR antibodies' receptor occupancy can be determined using assays as described in the present invention adapted to the particular NKCIR bound by the antibody (see, e.g., Example 2). Anti-NKCIR antibodies' pharmacokinetic properties can be determined using assays as described in the present invention adapted to the particular anti-NKCIR antibody (see, e.g., Example 1).

EXAMPLES

Example 1—Pharmacokinetics in Patients

Plasma concentrations of anti-KIR antibody 1-7F9 are determined by ELISA as briefly described below.

The plates are coated with KIR2DL3 coating solution (100 µl/well) and incubated overnight at about +4° C. The plates are then washed 3 times with wash buffer using an automated plate washer (4000/well). Blocking buffer is added (200 µl per well) and plates are incubated for approximately 2 hours on a plate shaker at room temperature. After this, the plates are once again washed 3 times with wash buffer (400 µl/well).

Standards, quality controls and samples are added to the plates (100 µl/well) before incubation for approximately 2 hours on the plate shaker at room temperature. Before adding mouse anti-human IgG4:peroxidase working solution (100 µl/well) the plates are washed another 3 times (as above). The plates are then again incubated for approximately 2 hours on a plate shaker at room temperature, after which they are washed once again.

TMB is added to the plates (100 µl/well), which are then incubated for approximately 30 minutes on a plate shaker at room temperature. The enzymatic reaction is terminated with addition of stop solution (50 µl/well). Absorbances are read at 450 nm (reference filter 650 nm). The lower limit of quantification for this study is 5.000 ng/mL and the upper limit of quantification for this study is 110.0 ng/mL.

Example 2—KIR Occupancy Assay

Receptor occupancy is evaluated on human whole blood samples by four-color fluorescence analysis. Briefly, free and bound KIR2D receptor levels are assessed on T and NK lymphocytes in EDTA anti-coagulated peripheral blood. Free site assay will assess unbound KIR2D by staining with PE-conjugated 1-7F9, which binds to the KIR2D molecule. Bound site assay will assess KIR2D receptors occupied by 1-7F9 by staining with a PE-conjugated mouse anti-human IgG4 monoclonal antibody that recognizes the 1-7F9 bound to the KIR2D receptors. The Free and Bound Assays will allow for assessment of both percentage positive staining as well as the fluorescence intensity [MESF] for 1-7F9-PE or anti-hIgG4-PE. The following combinations of conjugated antibodies are used in the following two assays:

Free Site Assay: CD3/1-7F9/CD45/CD56
Bound Assay: CD3/hIgG4/CD45/CD56

Samples are analyzed on a Becton Dickinson FACScalibur using the Becton Dickinson Cellquest software. T cells are defined as CD45+CD3+ lymphocytes and NK cells are defined as CD45+CD3−CD56+ cells.

Example 3—Clinical AML Study

A single dose escalation trial was conducted in elderly AML patients (>60 years), who are in first complete remission following induction and consolidation chemotherapy, and not eligible for bone-marrow transplantation. A standard 3+3 design is applied, and a total of 7 dose levels were explored: Doses range from 0.0003 mg/kg to 3 mg/kg. Following dosing, the patients were monitored for safety, PK and KIR occupancy until KIR occupancy was no longer detectable.

An extension trial was also conducted. AML patients who had completed the dose-escalation trial and who were still in complete remission could participate in the extension trial, in which the patients were dosed up to 6 times on a monthly basis. The patients are dosed with the same dose as they received in the previous trial.

Patients, Materials and Methods

In both trials, elderly AML patients (>60 years of age) in their first complete remission (CR) and not eligible for transplantation were eligible for the studies. AML was according to WHO Criteria. (Brunning R D, Matutes E, Harris N L et al.: Acute myeloid leukaemia: Introduction. In Jaffe E S, Harris N L, Stein H, et al. Eds.: Pathology and Genetics of Tumors of Haematopoietic and Lymphoid Tissues. Lyon, France: IARC Press, 2001. World Health Organization Classification of Tumors, 3, pp 77-80). Remission was morphological complete remission (CR) defined according to NCI criteria (Cheson et al. *JCO*, Vol 21, no. 24, pp 4642-4649 (2003)), or CRi with incomplete platelet count recovery only after 1 or 2 cycles of induction chemotherapy, and at least 1, and maximally 6 cycles of consolidation chemotherapy.

At screening in the dose-escalation trial, the time since last dose of chemotherapy was at least 30 days and no more than 120 days. Other eligibility criteria included (but were not limited to) expression of KIR2DL1 and 2/3 on NK-cells, ECOG (Oken, M. M., et al. Toxicity And Response Criteria Of The Eastern Cooperative Oncology Group. Am J Clin Oncol 5:649-655, 1982) status 0-2 and recovery from all toxicities from previous treatment.

For the extension trial, completion of the dose-escalation trial with an acceptable safety profile was an additional eligibility criterion.

Additional criteria included absolute neutrophil count >1×10⁹/L, Platelets >80×10⁹/L, less than 5% blasts in bone-marrow, no Auer rods, no symptoms of disease, recovery from acute toxicities of all previous anti-leukemic therapies, KIR-expression on patient NK-cells (ability to bind anti-KIR antibody 1-7F9), no major relevant organ dysfunction as judged by the Investigator, and clinical laboratory values as follows: (a) A Serum creatinine ≤2 mg/dL, (b) Total bilirubin ≤1.5× the upper limit of normal and (c) AST≤3× the upper limit of normal.

Study Design

The dose-escalation trial is a multi-centre, open-label, single dose-escalation safety and tolerability trial. Seven dose levels are planned to be explored; 0.0003 mg/kg, 0.003 mg/kg, 0.015 mg/kg, 0.075 mg/kg, 0.3 mg/kg, 1 mg/kg and 3 mg/kg. A general (3+3) design is chosen for this trial. Each patient is allocated to one dose, and is monitored for safety, pharmacokinetics and pharmacodynamics until there is no detectable KIR-occupancy on the patients NK-cells. Safety, PK and KIR-occupancy are analysed on an on-going basis, and the data obtained during the first 4 weeks post dosing from each dose group generally forms the foundation of the dose-escalation decision.

The extension trial is designed as a repeated dosing, multi-centre, open-label, safety and tolerability. The dose given to the individual patient is the same as the patient received in the single dose trial. The patient can receive 6 administrations at 4 week interval i.e. 6 dosing cycles with a maximal to duration of 6 months. Each dosing cycle consists of a dosing visit and a safety monitoring visit. Following the last dosing, the patient is monitored for safety until there is no detectable KIR-occupancy on the patients NK-cells. The duration of this safety follow-up period likely depends on the dose received, and is expected to be maximally 24 weeks post the last dosing.

Safety (i.e. any observed toxicity) to anti-KIR antibody 1-7F9 administration is assessed using the US National Cancer Institute Common Terminology Criteria for Adverse Events (CTCAE) version 3.0. Pharmacokinetic endpoints, KIR-occupancy, markers of NK- and T-cell activation, WT-1 tumour marker, progression-free survival and overall survival is also evaluated.

Results of AML Study

Receptor saturation was evaluated in the dose escalation trial among the patients receiving each dose level of 0.0003 mg/kg, 0.003 mg/kg, 0.015 mg/kg, 0.075 mg/kg, 0.3 mg/kg, 1 mg/kg and 3 mg/kg. In summary, dose 0.0003 mg/kg resulted in partial KIR saturation (50% occupancy) for a period of about 2 hours; dose 0.003 mg/kg resulted in full KIR saturation (90% occupancy) for a period of less than 24 hours; dose 0.015 mg/kg resulted in full KIR saturation for a period of less than 7 days; dose 0.075 mg/kg resulted in full KIR saturation for a period of almost 7 days; dose 0.3 mg/kg resulted in full KIR saturation for a period of greater than 7 days and less than 14 days; dose 1 mg/kg resulted in full KIR saturation for a period of less than 3 weeks (between about 2 weeks and 3 weeks); dose 3 mg/kg resulted in full KIR saturation for a period of more than 4 weeks.

Patients treated at dose levels of 0.0003 mg/kg, 0.003 mg/kg, 0.015 mg/kg, 0.075 mg/kg, 0.3 mg/kg, 1 mg/kg and 3 mg/kg were evaluated for disease free survival (DFS) from the time of beginning of treatment. Results are shown in Table 4. Patients receiving dose levels of 1 mg/kg and 3 mg/kg experienced significantly greater DFS than patients at lower doses. Additionally, there was an even stronger suggestion of a dose relationship when time to relapse was calculated from the time of initiation of IPH21 therapy, with a median of 11 weeks (range 3 to 112 weeks) at lower doses vs. 43 weeks (range 36 to 71 weeks) at higher doses Receptor saturation, including continued saturation for prolonger periods of time therefore appears not to induce significant hyporeactivity or deficiencies in NK cell education and appears to be more effective than repeated stimulation with doses that produce do not produce receptor saturation. Additionally, DFS for patients receiving 1 mg/kg and 3 mg/kg (73 weeks and ongoing for patients remaining free of disease) appears to be much higher than expected for patients not receiving treatment. Consequently, modulation of NK cells with anti-KIR antibody has a significant beneficial effect when administered to patients in remission. The effect if particularly high when antibody is dosed to achieve complete receptor saturation of at least 2 weeks and in particular with continued complete receptor saturation, during the course of repeated cycles of dosing (here 6 administrations of the 1 mg/kg and 3 mg/kg dose levels that result in about one-month saturation, administered once per month).

TABLE 4

|  |  | DFS = Relapse-CR (weeks) | PFS = Relapse-IPH21 (weeks) | Delay CR-IPH2101 (weeks) |
|---|---|---|---|---|
| All the pts (21) | Median | 51 | 35 | 20 |
|  | Mean | 67 | 47 | 21 |
| Group = 0.3 (15) | Median | 42 | 10 | 19 |
|  | Mean | 55 | 36 | 20 |
| Group 1-3 mg (6) | Median | 92 | 55 | 26 |
|  | Mean | 97 | 73 | 24 |

Example 4—Clinical Study in Smoldering Multiple Myeloma

A two-arm trial using two different doses of anti-KIR antibody 1-7F9 resulting in continued or intermittent saturation is conducted in patients having SMM. A first group A is treated with: 0.2 mg/kg, leading to a full (>90%) but transient saturation over at least about 7 days after each injection, and a group B receives 2 mg/kg, leading to a full and sustained saturation between two consecutive injections. The patents are dosed up to 6 times on a monthly basis and examined for safety and criteria of efficacy, including criteria indicating progression of disease toward MM.

Patients, Materials and Methods

Patients eligible for the study have SMM of any risk level according to a definition derived of the International Myeloma Working Group definition (Br J Haematol 2003; 121: 749): Serum M protein ≥3 g/dl, AND/OR Bone Marrow plasma cells ≥10% with no evidence of end-organ damage (CRAB):
 (C) Absence of hypercalcemia: Ca <10.5 mg/dl
 (R) Absence of renal failure: creatinine <2 mg/dl (177 μmol/l) or calculated creatinine clearance (according to MDRD) >50 ml/min
 (A) Absence of anemia: Hb >11 g/dl
 (B) Absence of lytic bone lesion on standard skeletal survey (MRI could be used if clinically indicated).

Patients also must have measurable disease defined as a disease with a serum M protein ≥1 g/dl, and no evidence of fatigue, recurrent infections or any clinical suspicion of MM.

Study Design

Two doses are assessed, with patients assigned by randomization:
 In group A: 0.2 mg/kg, leading to a full (>90%) but transient saturation over at least 7 days after each injection.
 In group B: 2 mg/kg, leading to a full and sustained saturation between two consecutive injections.

In both groups, anti-KIR antibody 1-7F9 is administered every 4 weeks by intravenous route over 1 hour for 6 times. The same dose will be used during the entire study in all the patients. Anti-KIR antibody 1-7F9 will be administered every 4 weeks for 6 cycles. A patient whose disease achieves at least minimal response to study treatment after 6 cycles, will be treated with an additional period of treatment of 6 cycles. Patients will be followed in study up to 12 or 18 months i.e. 6 months after the completion of the treatment (or longer if KIR saturation was still >30% 6 months after treatment completion).

Evaluation Criteria

Responses is classified according to the IMWG uniform response criteria (Durie B G M et al; Leukemia 2006; 20: 1467) modified in order to include minimal response as derived from the EBMT criteria (Blade et al; Br J Haematol 1998; 102: 115. Definition of minimal response is derived from EBMT criteria (Blade et al; Br J Haematol 1998; 102: 115) and required both: (a) a 25-49% reduction, in the level of the serum protein and (b) a 50-89% reduction in 24 h urinary protein M excretion which still exceeds 200 mg/24 h.

Immunofixation and bone marrow examination is performed in all patients whose serum and urine electrophoresis becomes negative; serum free light chains are measured at baseline and in all patients whose disease achieve CR criteria and immunophenotyping of bone marrow is performed in all patients whose disease achieve CR criteria. M protein is quantified using dosimetry on serum and urine protein electrophoresis. When urine samples are missing, response will be evaluated on serum level only.

Additionally, DOR (Response duration), PFS (Progression Free Survival) and Time to progression (TPP) will be documented during the study period.

Example 5—Clinical Study in Multiple Myeloma Following Response to First-Line Therapy An open label, randomised two independent arms, multi-centre study, with a Gehan's one-stage phase II design is conducted to evaluate the response on M-protein levels in serum to two different dose regimen of a human monoclonal anti-KIR antibody 1-7F9. Patients will receive 4 injections of 1-7F9, at the dose of either 0.2 mg/kg or 2 mg/kg (according to their randomisation) administered over one hour infusion at four weeks intervals.

Patients, Materials and Methods

Eligible for the study are patients with MM who initially required a systemic therapy and received a first line treatment, conventional doses of chemotherapies or high dose chemotherapy and an autologous transplantation of hematopoietic cells, followed or not by a consolidation treatment.

Patients may have residual disease or responses to prior treatment. Residual disease is disease having (a) quantifiable serum M-protein of ≥3 g/l, except for spike in the beta globulin area in which case serum M-protein is considered quantifiable if ≥10 g/l; or (b) serum M-protein is <3 g/l, measurable involved Free Light Chains ≥100 mg/l and an abnormal Free light chains ratio (<0.26 or >1.65).

For patients which responses are partial (PR and VGPR) and in plateau, partial response should meet the IMWG uniform response criteria: a ≥50% reduction from value of serum M-protein before the first line chemotherapy treatment and a reduction in 24 h urinary M-protein by ≥90% or to <200 mg/24 h. Very good partial response are defined according to the IMWG uniform response criteria with 90% or greater reduction in serum M-protein plus urine M-protein level <100 mg/24 h. Plateau phase for patients with serum M-protein ≥3 g/l: stable levels of M-protein in serum during at least 2 months, and for patients with serum M-protein <3 g/l: stable levels of Free Light Chains in serum.

Patients further have an ECOG (Eastern Cooperative Oncology Group) performance status of 0, 1 or 2.

Study Design

One infusion of antibody 1-7F9 is administered every 4 weeks at the dose of either 0.2 mg/kg or 2 mg/kg, according to the randomisation group, by intravenous route over 1 hour, for 4 cycles. Patients responding at 4 months (decrease in serum M-protein) will be allowed to receive an additional period of treatment of 4 monthly administrations. The same dose will be used during the whole study in all the patients of one arm.

The first dose, 0.2 mg/kg, is expected to lead to complete receptor saturation for nor more than about 1 week.

The second dose, 2 mg/kg is slightly above the dose saturating the receptors for a period of at least 1 month.

Evaluation Criteria

Efficacy is evaluated based on levels of M-protein quantified using dosimetry in serum and 24 h urine electrophoresis, and levels of free Light Chains, quantified using nephelometry with a binding site Freelite assay. Survival endpoints, including TTP (time to progression), PFS (progression free survival), DOR (duration of response), and OS (overall survival) are evaluated.

Results

Of the first 7 patients in each arm treated with of 0.2 mg/kg or 2 mg/kg for 4 doses, one response to treatment was observed in the 2 mg/kg treatment arm (sustained receptor saturation), as assessed by decrease in M-protein (M protein which decreased from 25%, confirmed at 2 consecutive visits).

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law), regardless of any separately provided incorporation of particular documents made elsewhere herein.

The use of the terms "a" and "an" and "the" and similar referents in the context of describing the invention are to be construed to cover both the singular and the plural, unless otherwise indicated herein or clearly contradicted by context.

Unless otherwise stated, all exact values provided herein are representative of corresponding approximate values (e.g., all exact exemplary values provided with respect to a particular factor or measurement can be considered to also provide a corresponding approximate measurement, modified by "about," where appropriate).

The description herein of any aspect or embodiment of the invention using terms such as "comprising", "having," "including," or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

We claim:

1. A method for treating acute myeloid leukemia (AML) or multiple myeloma (MM) in an individual who has been previously treated for AML or MM, wherein the previous treatment was a conventional therapy, and who has been identified as having a genetic aberration that correlates with a poor prognosis for survival selected from the group consisting of a genetic mutation in FLT3 and/or NpM1; a rearrangement in an immunoglobulin (Ig) gene and/or T cell receptor gene; abnormalities of chromosome 5 or chromosome 7; and a complex karyotype, said method comprising (1) obtaining a sample from said individual previously treated for AML or MM and assaying said sample in order to determine whether said individual has said genetic aberration, and (2) administering to said individual who has been determined to have said genetic aberration, at a time when the individual has minimal or non-detectable disease, a therapeutically active amount of a monoclonal anti-Killer Immunoglobulin-like Receptor (KIR) antibody or antigen-binding fragment which binds to KIR2DL1 and KIR2DL2/3 and has the ability to block or neutralize KIR2DL1- and KIR2DL2/3-mediated NK cell inhibition and thereby potentiate NK cell-mediated cytotoxicity, wherein said administration enhances said individual's likelihood of survival, and wherein said anti-KIR antibody or antigen-binding fragment is administered (a) in an amount resulting in substantially complete saturation of KIR2DL1 and KIR2DL2/3 on NK cells for a period of at least about 1 week, at least about 2 weeks, or at least about 1 month; and (b) at a dosing frequency of once about every 2 weeks, once about every 1 month or once about every 2 months or longer.

2. The method of claim 1, wherein the treated individual experienced a partial response or complete response, is in remission, is asymptomatic, has a low number of abnormal cells and/or has a non-detectable disease based on one or more of the following: (i) a total body leukemia burden below approximately $10^9$ cells and/or less than 5% blasts in the marrow and/or no signs or symptoms of leukemia; (ii) a greater than 25% reduction in the serum protein M level; (iii) a greater than 50% reduction in the serum protein M level; (iv) 10% or more plasma cells in the bone marrow, but does not meet the criteria for multiple myeloma (MM); (v) serum M proteins levels greater than or equal to 3 g/dL; (vi) 10% or more plasma cells in the bone marrow with no evidence of end-organ damage; (vii) serum M protein levels greater than or equal to 3 g/dL and has 10% or more plasma cells in the bone marrow; (viii) serum M protein levels greater than or equal to 3 g/dL and has 10% or more plasma cells in the bone marrow and no evidence of end-organ damage; and (ix) less than 10% plasma cells in the bone marrow.

3. The method of claim 1, wherein the anti-KIR antibody or antigen-binding fragment is administered as a pharmaceutically acceptable composition comprising a therapeutically effective amount of the anti-KIR antibody or antigen-binding fragment.

4. The method of claim 1, wherein the anti-KIR antibody or antigen-binding fragment is administered in a dosage range of about 0.1 mg/kg to about 3.0 mg/kg, about 0.3 mg/kg to about 3.0 mg/kg, about 0.1 mg/kg to about 1.0 mg/kg, about 1.0 mg/kg to about 3.0 mg/kg, or about 0.2 mg/kg or about 0.3 mg/kg.

5. The method of claim 1, wherein step (1) comprises obtaining a sample from said individual who has been previously treated for AML or MM and identifying in said sample a population of abnormal cells, sorting the population of abnormal cells, and contacting nucleic acid isolated from the sorted population of abnormal cells with one or more nucleic acids that target said genetic aberration that correlates with a poor prognosis for survival.

6. The method of claim 1, wherein step (1) comprises: obtaining a cell sample from the individual who has previously been treated for AML, identifying a population of abnormal cells in the sample, sorting the population of abnormal cells, and contacting nucleic acid isolated from the sorted population of abnormal cells with one or more nucleic acids that target the genetic aberration that correlates with a poor prognosis for survival in AML selected from the group consisting of a genetic mutation in FLT3 and/or NpM1; a rearrangement in the Ig gene and/or T cell receptor gene; abnormalities of chromosome 5 or chromosome 7; and a complex karyotype.

7. The method of claim 1, wherein step (1) comprises obtaining a cell sample from said individual who has been previously treated for AML or MM and identifying whether said sample includes cells comprising a genetic mutation in FLT3 or NpM1 that correlates with a poor prognosis for survival.

8. The method of claim 1, wherein the conventional treatment is chemotherapy, an immunomodulatory agent, radiotherapy, surgery, an anti-hormone agent, an anti-angiogenic agent, or a combination of any of the foregoing.

9. The method of claim 1, wherein the treated individual has no detectable AML or MM disease.

10. The method of claim 1, wherein the individual is at least 60 years old.

* * * * *